(12) United States Patent
Kulagowski et al.

(10) Patent No.: US 6,225,320 B1
(45) Date of Patent: May 1, 2001

(54) SPIRO-AZACYCLIC DERIVATIVES AND THEIR USE AS THERAPEUTIC AGENTS

(75) Inventors: Janusz Jozef Kulagowski, Sawbridgeworth; Piotr Antoni Raubo, Bishops Stortford; Christopher John Swain, Duxford; Christopher George Thomson, Sawbridgeworth, all of (GB)

(73) Assignee: Merck Sharp & Dohme Ltd., Hertfordshire (GB)

( * ) Notice: Subject to any disclaimer, the term of this patent is extended or adjusted under 35 U.S.C. 154(b) by 0 days.

(21) Appl. No.: 09/424,108

(22) PCT Filed: May 27, 1998

(86) PCT No.: PCT/GB98/01541

§ 371 Date: Nov. 18, 1999

§ 102(e) Date: Nov. 18, 1999

(87) PCT Pub. No.: WO98/54187

PCT Pub. Date: Dec. 3, 1998

(30) Foreign Application Priority Data

May 29, 1997 (GB) .................................. 9711114

(51) Int. Cl.[7] ..................... C07D 221/20; C07D 405/02; A61K 31/5585; A61K 31/559
(52) U.S. Cl. .............................................. 514/278; 546/16
(58) Field of Search ................................ 546/16; 514/278

(56) References Cited

FOREIGN PATENT DOCUMENTS

94/17045 * 8/1994 (WO).
WO 94/17045 8/1994 (WO).
97/19084 * 8/1994 (WO).
94/20500 * 9/1994 (WO).
WO 94/20500 9/1994 (WO).
WO 96/20197 7/1996 (WO).
WO 97/19084 5/1997 (WO).
WO 98/13369 4/1998 (WO).

* cited by examiner

*Primary Examiner*—Alan L. Rotman
*Assistant Examiner*—Rita Desai
(74) *Attorney, Agent, or Firm*—J. Eric Thies; David L. Rose

(57) ABSTRACT

Substituted spiro-azacyclic derivatives of structural formula I are tachykinin receptor antagonists of use, for example, in the treatment of pain, inflammation, migraine, emesis and posttherpetic neuralgia

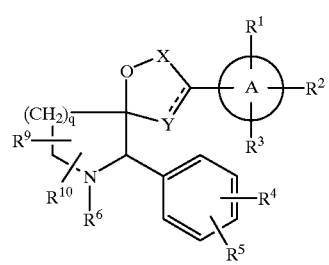

(I)

Wherein A is a pyridyl, X is —CH2—, Y is —CH2— or —CH= and q is 2.

19 Claims, No Drawings

SPIRO-AZACYCLIC DERIVATIVES AND THEIR USE AS THERAPEUTIC AGENTS

CROSS REFERENCE TO RELATED APPLICATIONS

This application claims priority under 35 U.S.C. 371 from PCT/GB98/01541, filed May 27, 1998, which claims priority from Great Britain Application No. 9711114.0, filed May 29, 1997.

This invention relates to a class of azacyclic compounds which are useful as tachykinin antagonists. More particularly, the compounds of the invention are spiro-substituted azacyclic derivatives.

International (PCT) patent specification no. WO 94/20500 (published Sep. 15, 1994) discloses spiroazacyclic derivatives as substance P antagonists. In particular, WO 94/20500 relates to spirocyclic piperidine derivatives containing a 1,8-diazaspiro[5.5]undecane core.

We have now found a further class of non-peptides which are potent antagonists of tachykinins, especially of substance P.

The present invention provides compounds of the formula (I):

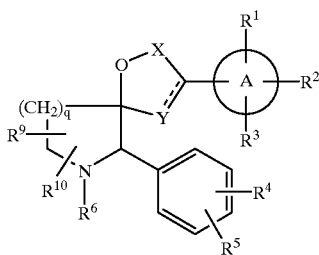

(I)

wherein
ring A represents a 6-membered aromatic heterocyclic group containing one, two or three nitrogen atoms;
X represents —$CH_2$— or —$CH_2CH_2$—;
Y represents —$CH_2$—, —$CH_2CH_2$—, —CH= or —$CH_2$CH=, with the proviso that the sum total of carbon atoms in X and Y is 2 or 3;
$R^1$ represents hydrogen, hydroxy, $C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, benzyloxy, cyano, halogen, $NR^aR_b$, $SR^a$, $SOR^a$, $SO_2R^a$ or $OSO_2R^a$, where $R^a$ and $R^b$ each independently represent hydrogen, $C_{1-4}$alkyl or fluoro$C_{1-4}$alkyl;
$R^2$ represents hydrogen, halogen, $C_{1-6}$alkyl or $C_{1-6}$alkoxy;
or when $R^2$ is adjacent to $R^1$, they may be joined together such that there is formed a 5- or 6-membered saturated or unsaturated ring containing one or two atoms selected from nitrogen, oxygen and sulphur, which ring is optionally substituted by a group selected from $C_{1-4}$alkyl, $CF_3$, =O or =S;
$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR^{14}$, $NR^aSO_2R^{14}$, or $C_{1-4}$alkyl substitued by cyano or $CO_2R^a$ where $R^a$ and $R^b$ are as previously defined;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, CN, $SR^a$, $SOR^a$, $SO_2R^a$, $COR^a$, $CO_2R^a$, phenyl, —$(CH_2)_rNR^aR^b$, —$(CH_2)_rNR^aCOR^b$, —$(CH_2)_rCONR^aR^b$, or $CH_2C(O)R^a$, where $R^a$ and $R^b$ are each independently hydrogen or $C_{1-4}$alkyl and r is zero, 1, or 2;
$R^4$ represents hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;
$R^5$ represents hydrogen, halogen, $C_{1-6}$alkyl, $CF_3$ or $C_{1-6}$alkoxy substituted by $C_{1-4}$alkoxy;
$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, C(NOH)$NR^aR^b$, CONHphenyl ($C_{1-4}$alkyl), $COCO_2R^a$, $CONHNR^aR^b$, C(S)$NR^aR^b$, $CONR^aC_{1-6}$alkyl$R^{12}$, $CONR^{13}C_{2-6}$alkenyl, $CONR^{13}C_{2-6}$alkynyl, $COCONR^aR^b$, $CONR^aC(NR^b)$$NR^aR^b$, $CONR^a$heteroaryl, and phenyl optionally substituted by one, two or three substituents selected from $C_{1-6}$alkyl, $C_{1-6}$alkoxy, halogen and trifluoromethyl);
or $R^6$ represents a group of the formula —$CH_2C\equiv CCH_2NR^7R^8$ where $R^7$ and $R^8$ are as defined below;
or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula $ZNR^7R^8$ where
Z is $C_{1-6}$alkylene or $C_{3-6}$cycloalkyl;
$R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;
$R^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;
or $R^7$, $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or $NR^c$ moiety where $R^c$ is $C_{1-4}$alkyl optionally substituted by hydroxy or $C_{1-4}$alkoxy;
or $R^7$, $R^8$ and the nitrogen atom to which they are attached form a non-aromatic azabicyclic ring system of 6 to 12 ring atoms;
or Z, $R^7$ and the nitrogen atom to which they are attached form a heteroaliphatic ring to 4 to 7 ring atoms which may optionally contain an oxygen ring atom;
$R^9$ and $R^{10}$ each independently represent hydrogen, halogen, $C_{1-6}$alkyl, $CH_2OR^d$, oxo, $CO_2R^a$ or $CONR^aR^b$ where $R^a$ and $R^b$ are as previously defined and $R^d$ represents hydrogen, $C_{1-6}$alkyl or phenyl;

$R^{12}$ represents $OR^a$, $CONR^aR^b$ or heteroaryl;

$R^{13}$ represents H or $C_{1-6}$alkyl;

$R^{14}$ represents $C_{1-6}$alkyl, $C_{1-6}$alkoxy, fluoro$C_{1-6}$alkyl or phenyl;

q is 1 or 2; and when Y is —CH= or —CH$_2$CH=, the broken line represents a double bond;

and pharmaceutically acceptable salts thereof.

Preferably, $R^1$ is attached to a carbon atom in ring A that is adjacent to the point of attachment of ring A to the remainder of the molecule.

Preferably $R^3$ is attached to a carbon atom in ring A that is two atoms away from the point of attachment of ring A to the remainder of the molecule and, where a susbtituents $R^1$ is present, $R^3$ is preferably not adjacent to $R^1$.

$R^2$, where present, is attached to any available carbon atom.

Suitable aromatic heterocyclic groups represented by ring A include pyridine, pyridazine, pyrimidine, pyrazine and 1,3,5-triazine.

Preferred compounds of the present invention are those wherein the ring A is a 6-membered aromatic heterocyclic group containing one or two nitrogen atoms, especially a pyridyl group.

Particularly preferred compounds of the present invention are those wherein the ring A is a 2,3,5- or 2,3,6-trisubstituted pyridine ring.

A preferred class of compound of formula (I) is that wherein $R^1$ is hydrogen, $C_{1-6}$alkyl, $C_{1-6}$alkoxy, fluoro$C_{1-6}$alkoxy, $C_{3-7}$cycloalkoxy, halogen or $NR^aR^b$; in particular a hydrogen atom or a methyl, trifluoromethyl, methoxy, ethoxy, isopropoxy, trifluoromethoxy, 2,2,2-trifluoroethoxy, cyclopropoxy or cyclobutoxy group; and especially a hydrogen atom or a methoxy or cyclopropoxy group.

Another preferred class of compound of formula (I) is that wherein $R^2$ is a hydrogen atom.

Also preferred is the class of compound of formula (I) in which $R^3$ is halogen, $C_{1-6}$alkyl, fluoro$C_{1-6}$alkyl, $C_{1-6}$alkoxy, fluoro$C_{1-6}$alkoxy, cyano or a 5-membered aromatic heterocyclic group as previously defined.

Particularly preferred is the class of compound of formula (I) in which $R^3$ is halogen or fluoro$C_{1-6}$alkoxy, especially fluorine, trifluoromethoxy or 2,2,2-trifluoroethoxy, or a 5-membered aromatic heterocyclic group as previously defined.

A further preferred class of compound of formula (I) is that wherein $R^4$ is a hydrogen atom or a fluorine atom.

Another preferred class of compound of formula (I) is that in which $R^5$ is a hydrogen atom.

Also preferred is the class of compound of formula (I) in which $R^9$ and $R^{10}$ are both hydrogen atoms.

A further preferred class of compound of formula (I) is that wherein $R^6$ is a hydrogen atom.

Also preferred is the class of compound of formula (I) in which $R^6$ is a $C_{1-6}$alkyl group, in particular $CH_2$, $CH(CH_3)$ and $CH_2CH_2$ and especially $CH_2$, substituted by a 5-membered heterocyclic ring containing 2 or 3 nitrogen atoms as previously defined.

In particular, the 5-membered ring is a heterocyclic ring selected from:

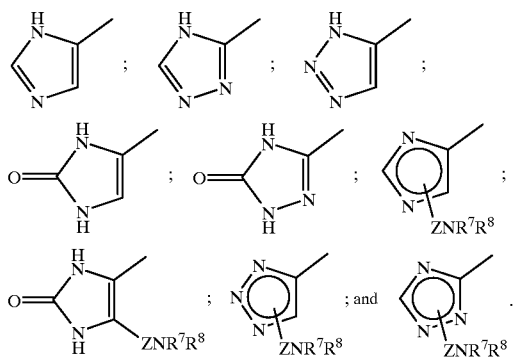

Particularly preferred heterocyclic rings are selected from:

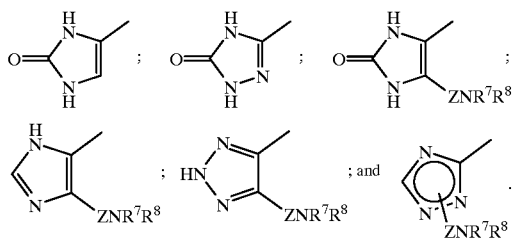

Certain particularly apt compounds of the present invention include those wherein $R^3$ is a group selected from pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each heteroaryl group being optionally substituted as previously defined.

Preferred compounds of the present invention are those wherein $R^3$ is a group selected from furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole and tetrazole, each heteroaryl group being optionally substituted as previously defined.

Particularly preferred compounds of the present invention are those wherein $R^3$ is a group selected from furan, pyridine, pyrimidine, 1,2,3-triazole, 1,2,4-triazole and tetrazole, each heteroaryl group being optionally substituted as previously defined.

An especially preferred class of compound of formula (I) is that wherein $R^3$ is the group

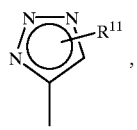

where $R^{11}$ is hydrogen, halogen, $C_{1-6}$alkyl, $C_{1-6}$alkoxy, $CF_3$, $OCF_3$, $NO_2$, $CN$, $SR^a$, $SOR^a$, $SO_2R^a$, $COR^a$, $CO_2R^a$, $(CH_2)_rCONR^aR^b$, $(CH_2)_rNR^aR^b$ or $(CH_2)_rNR^aCOR^b$, where $R^a$ and $R^b$ are hydrogen or $C_{1-4}$alkyl, and r is zero, 1 or 2.

Another especially preferred class of compound of formula (1) is that wherein $R^3$ is the group

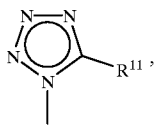

wherein $R^{11}$ is as previously defined.

Another especially preferred class of compound of formula (I) is that wherein $R^3$ is the group

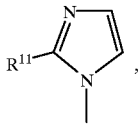

wherein $R^{11}$ is as previously defined.

$R^{11}$ is preferably hydrogen, $C_{1-4}$alkyl, especially methyl, $CF_3$, $(CH_2)_rCONR^aR^b$, $SOR^a$ or $SO_2R^a$ where $R^a$, $R^b$ and r are as previously defined. Most especially, $R^{11}$ is $CF_3$.

Preferably X is $-CH_2-$.

Preferably Y is $-CH_2-$ or $-CH=$, especially $-CH_2-$.

Preferably q is 2.

One favoured group of compounds of the present invention are of the formula (Ia) and pharmaceutically acceptable salts thereof:

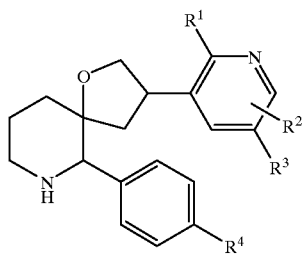

(Ia)

wherein $R^1$, $R^2$, $R^3$ and $R_4$ are as defined in relation to formula (I).

Another favoured group of compounds of the present invention are of the formula (Ib) and pharmaceutically acceptable salts thereof:

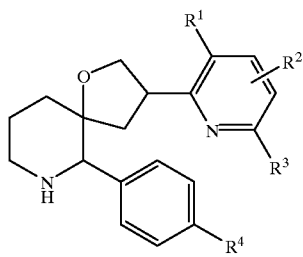

(Ib)

wherein $R^1$, $R^2$, $R^3$ and $R^4$ are as defined in relation to formula (I).

A further favoured group of compounds of the present invention are of the formula (Ic) and pharmaceutically acceptable salts thereof:

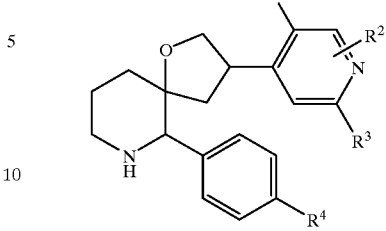

(Ic)

wherein $R^1$, $R^2$, $R^3$ and $R^4$ are as defined in relation to formula (I).

With respect to compounds of the formula (I), Z (where present), may be a linear, branched or cyclic group. Favourably Z contains 1 to 4 carbon atoms and most favourably 1 or 2 carbon atoms. A particularly favourable group Z is $CH_2$.

With respect to compounds of the formula (I), $R^7$ may aptly be a $C_{1-4}$alkyl group or a $C_{2-4}$alkyl group substituted by a hydroxyl or $C_{1-2}$alkoxy group, $R^8$ may aptly be a $C_{1-4}$alkyl group or a $C_{2-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.3.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^8$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

In the group $ZNR^7R^8$, Z is preferably $CH_2$ or $CH_2CH_2$, and especially $CH_2$.

The group $NR^7R^8$ preferably represents amino, methylamino, dimethylamino, diethylamino, azetidinyl, pyrrolidino and morpholino.

In particular, $NR^7R^8$ is preferably dimethylamino, azetidinyl or pyrrolidino, especially dimethylamino.

As used herein, the group $NR^aR^b$ preferably represents an amino, methylamino or dimethylamino group, especially dimethylamino.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl cyclopentyl or cyclohexyl. A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the terms "fluoroC$_{1-6}$alkyl" and "fluoroC$_{1-6}$alkoxy" means a C$_{1-6}$alkyl or C$_{1-6}$alkoxy group in which one or more (in particular, 1 to 3) hydrogen atoms have been replaced by fluorine atoms. Similarly, the term "fluoroC$_{1-4}$alkyl" means a C$_{1-4}$alkyl group in which one or more (in particular 1 to 3) hydrogen atoms have been replaced by fluorine atoms. Particularly preferred are fluoroC$_{1-3}$alkyl and fluoroC$_{1-3}$alkoxy groups, for example, CF$_3$, CH$_2$CH$_2$F, CH$_2$CHF$_2$, CH$_2$CF$_3$, OCF$_3$, OCH$_2$CH$_2$F, OCH$_2$CHF$_2$ or OCH$_2$CF$_3$, and most especially CF$_3$, OCF$_3$ and OCH$_2$CF$_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy. A suitably cycloalkylalkoxy group may be, for example, cyclopropylmethoxy.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the term "heteroaryl" as a group or part of a group means a 5- or 6-membered heteroaromatic ring containing 1 to 4 heteroatoms selected from N, O and S. Particular examples of such groups include pyrrolyl, furanyl, thienyl, pyridyl, pyrazolyl, imidazolyl oxazolyl, isoxazolyl, thiazolyl, isothiazolyl, pyrazinyl, pyrimidinyl, pyridazinyl, triazolyl, oxadiazolyl, thiadiazolyl, triazinyl, and tetrazolyl.

When used herein the term "halogen" means fluorine, chlorine, bromine and iodine. The most apt halogens are fluorine and chlorine of which fluorine is preferred, unless otherwise stated.

Specific compounds within the scope of this invention include:

(5R,6S)-3-(3-methoxy-6-N-methyltrifluoromethanesulfonamidopyridin-2-yl)-6-phenyl-1-oxa-7H-azaspirol[4.5]dec-3-ene;
(3S,5R,6S)-3-(3-methoxy-6-N-methyltrifluoromethanesulfonamidopyridin-2-yl)-6-phenyl-1-oxa-7H-azaspiro[4.5]decane;
(5R,6S)-3-(3-methoxy-6-(5-trifluoromethyl-1,2,3,4-tetrazol-1-yl)-pyridin-2-yl)-6-phenyl-1-oxa-7H-azaspiro[4.5]dec-3-ene;
(3S,5R,6S)-3-(3-methoxy-6-(5-trifluoromethyl-1,2,3,4-tetrazol-1-yl)-pyridin-2-yl-6-phenyl-1-oxa-7H-azaspiro[4.5]decane;
(5R,6S)-3-(3-methoxy-6-(2-trifluoromethylimidazol-1-yl)pyridin-2-yl)-6-phenyl-1oxa-7H-azaspiro[4.5]dec-3-ene;
(3S,5R,6S)-3-(3-methoxy-6-(2-trifluoromethylimidazol-1-yl)pyridin-2-yl)-6-phenyl-1-oxa-7H-azaspiro[4.5]decane;
(3S,5R,6S)-3-(3-methoxy-6-dimethylaminopyridin-2-yl)-6-phenyl-1-oxa-7H-azaspiro[4.5]decane;
(5R,6S)-3-(2-methoxy-5-trifluoromethylpyridin-3-yl)-6-phenyl1-oxa-7H-azaspiro[4.5]dec-3-ene;
(3S,5R,6S)-3-(2-methoxy-5-trifluoromethylpyridin-3-yl)-6-phenyl-1-oxa-7H-azaspiro[4.5]decane;
(5R,6S)-3-(2-dimethylamino-5-trifluoromethylpyridin-3-yl)-6-phenyl-1-oxa-7H-azaspiro[4.5]dec-3-ene;
(3S,5R,6S-3-(2-dimethylamino-5-trifluoromethylpyridin-3-yl)-6-phenyl-1-oxa-7H-azaspiro[4.5]decane;
(3S,5R,6S)-3-(2-(2,2,2-trifluoroethoxy)-5-trifluoromethylpyridin-3-yl)-6-phenyl-1-oxa-7H-azaspiro[4.5]decane;
(5R,6S)-3-(2-(2,2,2-trifluoroethoxy)-5-(2-trifluoromethylimidazol-1-yl)pyridin-3-yl)-6-phenyl-1-oxa-7H-azaspiro[4.5]dec-3-ene;
(3S,5R,6S)-3-(2-(2,2,2-trifluoroethoxy)-5-(2-trifluoromethylimidazol-1-yl)pyridin-3-yl)-6-phenyl-1-oxa-7H-azaspiro[4.5]decane;
(3S,5R,6S)-3-(2-methoxy-5-(2-trifluoromethylimidazol-1-yl)pyridin-3-yl)-6-phenyl-1-oxa-7H-azaspiro[4.5]decane;
(3S,5R,6S)-3-(2-isopropoxy-5-trifluoromethylpyridin-3-yl)-6-phenyl-1-oxa-7H-azaspiro[4.5]decane;
(3S,5R,6S)-3-(2-ethoxy-5-trifluoromethylpyridin-3-yl)-6-phenyl-1-oxa-7H-azaspiro[4.5]decane;
(3S,5R,6S)-3-(2-(2-methoxyethoxy)-5-trifluoromethylpyridin-3-yl)-6-phenyl-1-oxa-7H-azaspiro[4.5]decane;
(3R,5R,6S)-3-(2-isopropoxy-5-trifluoromethylpyridin-3-yl)-6-phenyl-1-oxa-7H-azaspiro[4.5]decane;
(3R,5R,6S)-3-(2-ethoxy-5-trifluoromethylpyridin-3-yl)-6-phenyl-1-oxa-7H-azaspiro[4.5]decane;
(3R,5R,6S)-3-(2-(2,2,2-trifluoroethoxy)-5-trifluoromethylpyridin-3-yl)-6-phenyl-1oxa-7H-azaspiro[4.5]decane;

and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The compounds of the formula (I), (Ia), (Ib) and (Ic) will have the preferred stereochemistry of the 5- and 6-positions that is possessed by the compound of Example 1 (i.e. 5-(R) and 6-(S)). Thus for example as shown in formula (Id)

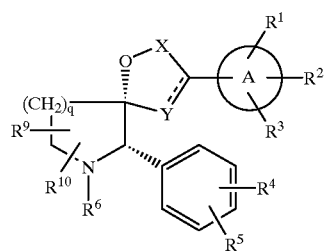

(Id)

According to yet further preference, the compounds of the formula (I), (Ia), (Ib), (Ic) and (Id) will have the stereochemistry of the 3-, 5- and 6-positions that is as shown in formula (Ie) (i.e. 3-(R), 5-(R), 6-(S))

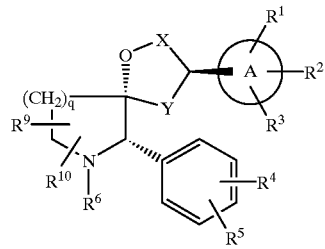

(Ie)

It will be appreciated that the preferred definitions of the various substituents recited herein may be taken alone or in combination, and apply to the generic formula for compounds of the present invention as well as to the preferred classes of compound represented by formulae (Ia), (Ib), (Ic), (Id) and (Ie).

The present invention further provides pharmaceutical compositions comprising one or more compounds of formula (I) in association with a pharmaceutically acceptable carrier or excipient.

Preferably the compositions according to the ivention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 μm, particularly 0.1 and 0.5 μm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, dental pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and broncho-spasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or domperidone, or GABA$_B$ receptor agonists such as baclofen. Additionally, a compound of formula (I) either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712 Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.*, (1993) 250, R5-R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and headache including migraine, acute or chronic tension headache, cluster headache, temporomandibular pain and maxillary sinus pain.

The compounds of formula (I) are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning walling, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antinflammatory agent such as a bradykinin receptor antagonist.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof Suitable classes of anti-anxiety agent include benzodiazepines and 5-HT$_{1A}$ agonists or antagonists, especially 5-HT$_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-HT$_{1A}$ receptor agonists or antagonists include, in particular, the 5-HT$_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of formula (I) and an anorectic agent for the manufacture of a medicament for the treatment or prevention of eating disorders.

The present invention also provides a method for the treatment or prevention of eating disorders, which method comprises administration to a patient in need of such treatment an amount of a compound of formula (I) and an amount of an anorectic agent, such that together they give effective relief.

In a further aspect of the present invention, there is provided a pharmaceutical composition comprising a compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of formula (I) and an anorectic agent as a combined preparation for simultaneous, separate or sequential use in the treatment or prevention of eating disorders.

In a further embodiment of the present invention there is provided the use of a compound of formula (I) and an anorectic agent for the manufacture of a medicament for the treatment or prevention of obesity.

The present invention also provides a method for the treatment or prevention of obesity, which method comprises administration to a patient in need of such treatment an amount of a compound of formula (I) and an amount of an anorectic agent, such that together they give effective relief.

In an alternative embodiment of the present invention there is provided the use of a compound of formula (I) and an anorectic agent for the manufacture of a medicament for the treatment or prevention of bulimia nervosa.

The present invention also provides a method for the treatment or prevention of bulimia nervosa, which method comprises administration to a patient in need of such treatment an amount of a compound of formula (I) and an amount of an anorectic agent, such that together they give effective relief.

In a further embodiment of the present invention there is provided the use of a compound of formula (I) and an anorectic agent for the manufacture of a medicament for the treatment or prevention of compulsive eating disorders.

The present invention also provides a method for the treatment or prevention of compulsive eating disorders, which method comprises administration to a patient in need of such treatment an amount of a compound of formula (I) and an amount of an anorectic agent, such that together they give effective relief.

In an alternative embodiment of the present invention there is provided the use of a compound of formula (I) and an anorectic agent for the manufacture of a medicament for reducing the total body fat mass in an obese mammal, especially a human.

The present invention also provides a method for reducing the total body fat mass in an obese mammal, especially a human, which method comprises administration to a patient in need of such treatment an amount of a compound of formula (I) and an amount of an anorectic agent, such that together they give effective relief.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

Particularly preferred anorectic agents include amphetamine and derivatives thereof such as amphetamine, benzphetamine, chlorphentermine, clobenzorex, cloforex, clotermine, dexfenfluramine, dextroamphetamine, diethylpropion, N-ethylamphetamine, fenfluramine, fenproporex, furfurylmethylamphetamine, levamfetamine, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention accordingly provides the use of a compound of formula (I) and an SSRI for the manufacture of a medicament for the treatment or prevention of obesity.

The present invention also provides a method for the treatment or prevention of obesity, which method comprises administration to a patient in need of such treatment an amount of a compound of formula (I) and an amount of an SSRI, such that together they give effective relief.

In a further aspect of the present invention, there is provided a pharmaceutical composition for the treatment or prevention of obesity comprising a compound of formula (I) and an SSRI, together with at least one pharmaceutically acceptable carrier or excipient It will be appreciated that the compound of formula (I) and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of formula (I) and an SSRI as a combined preparation for simultaneous, separate or sequential use in the treatment or prevention of obesity.

In an alternative embodiment of the present invention, there is provided the use of a compound of formula (I) and an SSRI for the manufacture of a medicament for reducing the total body fat mass in an obese mammal, especially a human.

The present invention also provides a method for reducing the total body fat mass in an obese mammal, especially a human, which method comprises administration to the mammal an amount of a compound of formula (I) and an amount of an SSRI, such that together they give effective relief.

In a further aspect of the present invention, there is provided a pharmaceutical composition for reducing the total body fat mass in an obese mammal, especially a human, comprising a compound of formula (I) and an SSRI, together with at least one pharmaceutically acceptable carrier or excipient.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared (kg/m$^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycycstic ovarian disease, cardiovascular diseases, osteoarthritis, dermatological disorders, hypertension, insulin resistance, hypercholesterolemia, hypertriglyceridemia, and cholelithiasis.

Thus, in one aspect, this invention relates to the inhibition and/or complete suppression of lipogenesis in obese mammals, i.e., the excessive accumulation of lipids in fat cells, which is one of the major features of human and animal obesity, as well as loss of total body weight. In another aspect, the invention ameliorates the conditions that are a consequence of the disease, such as preventing or arresting the progression of polycystic ovarian disease so that the patient is no longer infertile, and increasing the insulin sensitivity and/or decreasing or eliminating the need or usage of insulin in a diabetic patient, e.g., one with adult-onset diabetes or Type II diabetes.

"Mammals" include animals of economic importance such as bovine, ovine, and porcine animals, especially those that produce meat, as well as domestic animals, sports animals, zoo animals, and humans, the latter being preferred.

It will be appreciated that when using any combination described herein, both the compound of formula (I) and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), the compounds according to the invention in which X is —CH$_2$— and Y is —CH$_2$— or —CH$_2$CH$_2$—, may be prepared by the reduction of a compound of formula (I) in which the broken line represents a double bond, hereinafter referred to as a compound of formula (II)

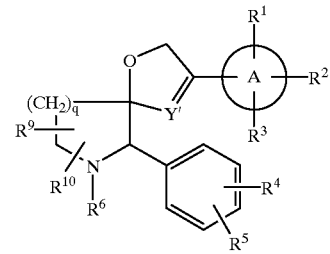

(II)

wherein ring A, R$^1$, R$^2$, R$^3$, R$^4$, R$^5$, R$^6$, R$^9$, R$^{10}$ and q are as defined in relation to formula (I) and Y' is —CH= or —CH$_2$CH=.

Suitable reducing conditions include: catalytic hydrogenation using a metal catalyst such as palladium or platinum or hydroxides or oxides thereof, preferably in a suitable solvent such as alcohol, e.g. methanol or ethanol, or an ester, e.g. ethyl acetate, or an organic acid e.g. acetic acid, or a mixture thereof.

According to another general process (B), compounds of formula (I) may be prepared by the interconversion of a corresponding compound of formula (I) in which $R^6$ is H, hereinafter referred to as formula (III)

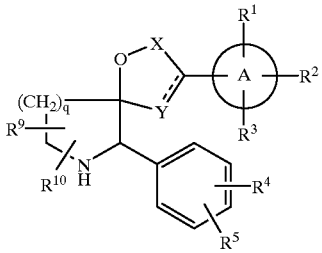
(III)

wherein ring A, $R^1$, $R^2$, $R^3$, $R^4$, $R^5$, $R^9$, $R^{10}$, X, Y, q and the broken line are as defined in relation to formula (I) by reaction with a compound of formula (IV):

(IV)

where $R^{6a}$ is a group of the formula $R^6$ as defined in relation to formula (I) (other than H) or a precursor therefor and LG is a leaving group such as an alkyl- or arylsulphonyloxy group (e.g. mesylate or tosylate) or a halogen atom (e.g. bromine, chlorine or iodine); and, if $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid acceptor such as potassium carbonate.

According to another general process (C), compounds of formula (I) may be prepared by a coupling reaction between a compound of formula (V) and (VI)

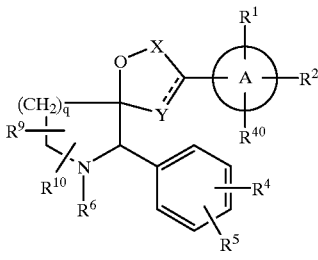
(V)

$R^{41}-R^3$ (VI)

wherein one of $R^{40}$ and $R^{41}$ is $B(OH)_2$ or $Sn(alkyl)_3$ or a derivative thereof, and the other is a leaving group such as a halogen atom e.g. bromine or iodine, or $-OSO_2CF_3$. Where one of $R^{40}$ and $R^{41}$ is $B(OH)_2$, the reaction is conveniently effected in the presence of a palladium (0) catalyst such as tetrakis(triphenylphosphine)palladium (0) in a suitable solvent such as an ether, for example, dimethoxyethane at an elevated temperature. Where one of $R^{40}$ and $R^{41}$ is $Sn(alkyl)_3$, the reaction is conveniently effected in the presence of palladium (II) catalyst such as bis(triphenylphosphine) palladium (II) chloride, in a suitable solvent such as an aromatic hydrocarbon, for example, toluene, at an elevated temperature.

According to another general process (D), compounds of formula (I) may be prepared from a compound of formula (VII)

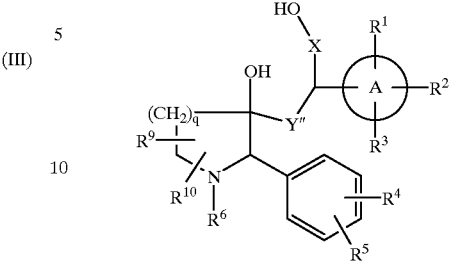
(VII)

wherein Y" is $-CH_2-$ or $-CH_2CH_2-$, by an acid catalysed intramolecular cyclisation reaction, or by a dehydration reaction.

Suitable acids of use in the intramolecular cyclisation reaction include mineral acids such as hydrochloric acid. The reaction is conveniently effected in a suitable organic solvent, such as an alcohol, e.g. methanol at an elevated temperature, for example, at the reflux temperature of the chosen solvent.

Suitable dehydrating reagents of use in the reaction include, for example, methanesulphonyl chloride or benzenesulphonyl chloride in pyridine or triethylamine. The reaction is conveniently effected at a temperature between 0° C. and 100° C., preferably at between room temperature and 80° C., using a suitable organic solvent such as dichloromethane, where necessary.

Intermediates of formula (VII) are particularly preferred for controlling the stereochemistry of the 3-position in compounds of formula (I).

According to another general process (E), compounds of formula (I) wherein X is $-CH_2-$ and Y is $-CH_2CH=$ (i.e. compounds of formula (II), above), may be prepared by the reaction of a compound of formula (VIII)

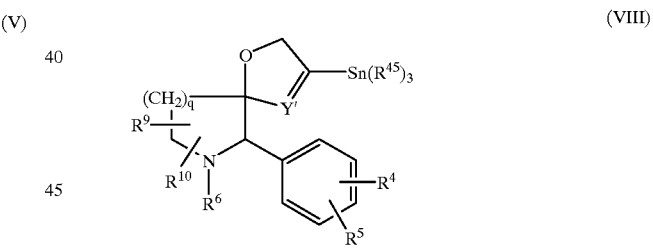
(VIII)

wherein each $R^{45}$ is a $C_{1-4}$alkyl group, preferably methyl or n-butyl groups, with a compound of formula (IX)

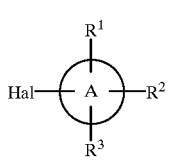
(IX)

wherein Hal is a halogen atom, for example, chlorine, bromine or iodine, especially bromine.

The reaction is conveniently effected in the presence of lithium chloride and a transition metal catalyst such as triphenylphosphine palladium (0). Suitable solvents for the reaction include aromatic hydrocarbons, for example, toluene, the reaction being effected at a temperature between 80° C. and the reflux temperature of the solvent.

According to another general process (F), compounds of formula (I) may be prepared by the reaction of a compound of formula (XVI)

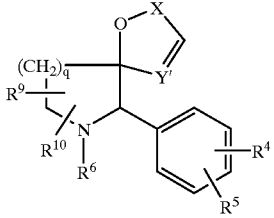

(XVI)

with a compound of formula (IX) under the conditions of a reductive Heck reaction using a palladium catalyst such as palladium acetate with, for example, tri-o-tolylphosphine, dimethylformamide and tributylamine, and a reducing agent, preferably formic acid or a salt thereof, such as potassium formate.

According to another general process (G), compounds of formula (I), in which $R^1$ is a cyclopropoxy group, may be prepared from a compound of formula (XXVII)

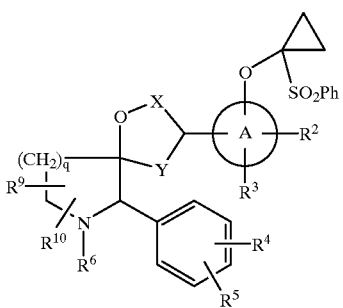

(XXVII)

wherein Ph is a phenyl group, by reaction with sodium amalgam, preferably in the presence of a buffer such as sodium hydrogen phosphate. The reaction is conveniently effected in a suitable solvent, for example, an alcohol such as methanol, conveniently at room temperature.

According to another general process (H), compounds of formula (I), in which X is —CH$_2$— and Y is —CH$_2$—, may be prepared by a two step reaction comprising a) reduction of a compound of formula (XXIV)

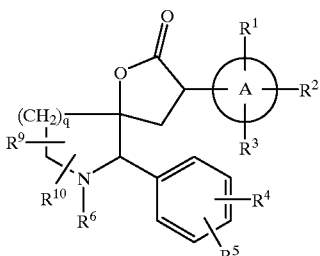

(XXIV)

to give a compound of the formula (XXIVa)

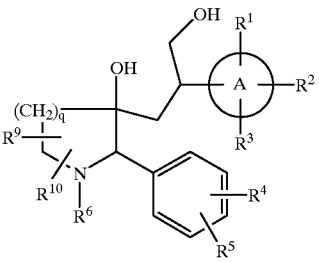

(XXIVa)

b) reaction of a compound of formula (XXIVa) with diethyl azodicarboxylate to effect cyclisation to give a compound of formula (I).

Suitable reducing agents of use in step (a) include for example, a borohydride such as lithium borohydride or lithium triethylborohydride in tetrahydrofuran or, more preferably, a hydride such as lithium aluminium hydride or diisobutylaluminium hydride.

This reaction is effected in a suitable solvent, for example an ether such as tetrahydrofuran, at a reduced temperature, for example, at 0° C.

Preparation of a diazo derivative in step (b) is conveniently effect using diethyl azodicarboxylate and cyclisation is effect in the presence of a suitable activator such as triphenylphosphine. The reaction is conveniently effected in a solvent, for example, an ether such as tetrahydrofuran, conveniently at room temperature.

Intermediates of formula (XXIV) are particularly preferred for controlling the stereochemistry of the 3-position of compounds of formula (I). In particular, reaction of a compound of formula (XXIV) with a base such as 1,8-diazabicyclo[5.4.0]undec-7-ene (DBU) in dichloromethane or using sodium methoxide in methanol may be used to improve the ratio of 3R epimer over the 3S epimer. The epimerisation step is conveniently effected at room temperature.

In a further preferred aspect, reaction of a compound of formula (XXIV), in which $R^6$ is a tert-butyloxycarbonyl group, with trifluoroacetic acid, conveniently in dichloromethane, results not only in deprotection of the azacyclic moiety, but also in an improvement in the ratio of the 3R epimer over the 3S epimer.

Further details of suitable procedures will be found in the accompanying Examples.

Intermediates of formula (III) may be prepared in a similar manner to general process (E), preferably with an amino protecting group on the pyrrolidine/piperidine nitrogen in the compound of formula (VIII). Suitable amino protecting groups include alkoxycarbonyl groups such as tert-butoxycarbonyl and trichloroethoxycarbonyl, aralkyloxycarbonyl groups such as benzyloxycarbonyl, or aralkyl groups such as benzyl. Removal of the protecting group is effected by conventional procedures thus, for example, tert-butoxycarbonyl groups may be removed under acidic conditions using, for example, trifluoroacetic acid; tert-butoxycarbonyl groups, together with benzyloxycarbonyl and benzyl groups, may also be removed by hydrogenolysis in the presence of a catalyst, for example, palladium; and trichloroethoxycarbonyl groups may be removed with zinc dust.

Compounds of formula (VIII) may be prepared from a compound of formula (X)

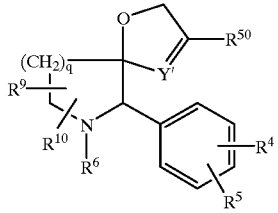

wherein $R^{50}$ is a triflate (—$OSO_2CF_3$) group or a bromine or iodine atom, by reaction with a compound of the formula $(R^{45})_3Sn$—$Sn(R^{45})_3$, for example, hexamethyl distannane. The reaction is conveniently effected in the presence of a base, for example, lithium carbonate, and a catalyst such as triphenylphosphine palladium(0). Suitable solvents for the reaction include ethers such as tetrahydrofuran, the reaction being effected at a temperature between room temperature and 100° C., for example, at about 60° C.

Compounds of formula (X) may be prepared from a compound of formula (XI):

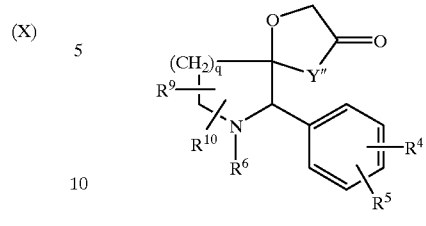

by enolisation of the ketone in the presence of a base, for example, sodium hexamethyldisilazide, followed by reaction with a reagent capable of introducing a suitable leaving group, for instance, where $R^{50}$ is —$OSO_2CF_3$, using 2-[N, N-bis(trifluoromethylsulphonyl)amino]-5-chloropyridine or triflic anhydride. The reaction is conveniently effected in a suitable solvent such as an ether, for example, tetrahydrofuran at a reduced temperature, for instance, −80° C.

Compounds of formula (XI) may be prepared from a compound of formula (XII) by the following reaction sequences (Scheme A or Scheme B) or by methods analogous thereto (with the proviso that $R^9$ and $R^{10}$ are not oxo):

Scheme A

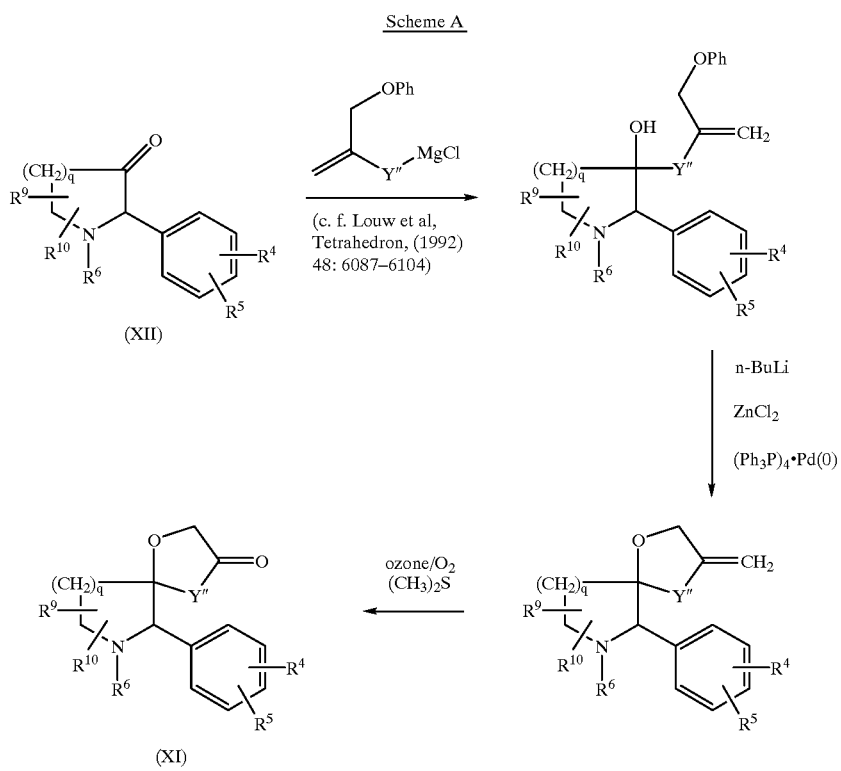

Scheme B
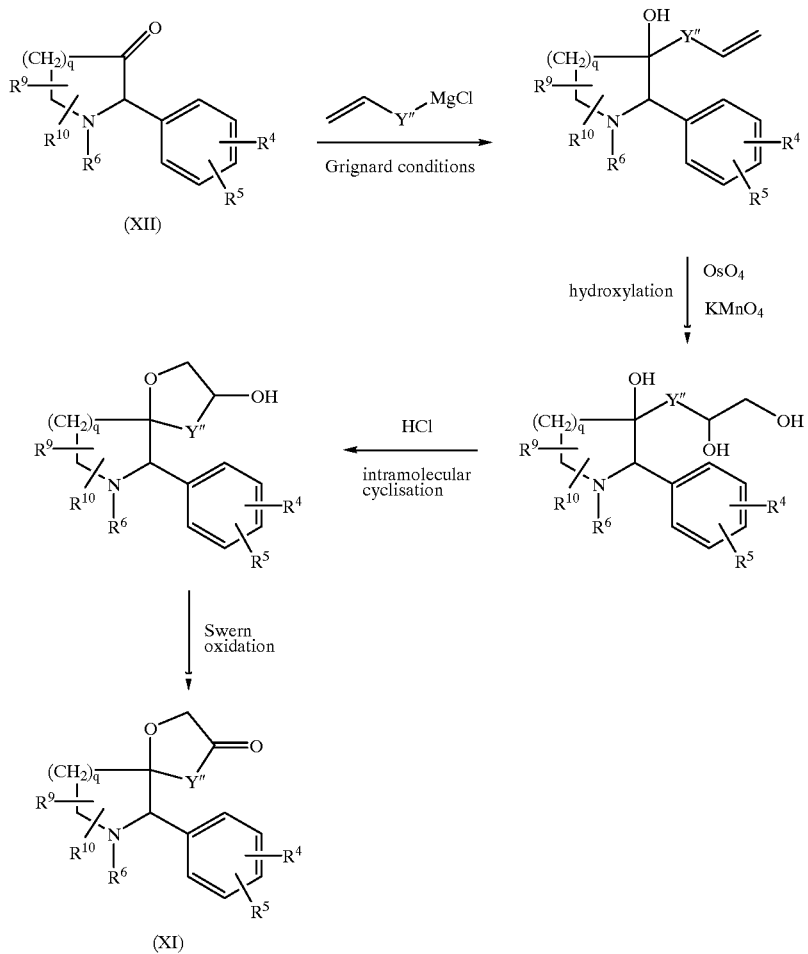
In an alternative method, compounds of formula (VII) may be prepared by the following reaction sequence (Scheme C) or by methods analogous thereto:
Scheme C
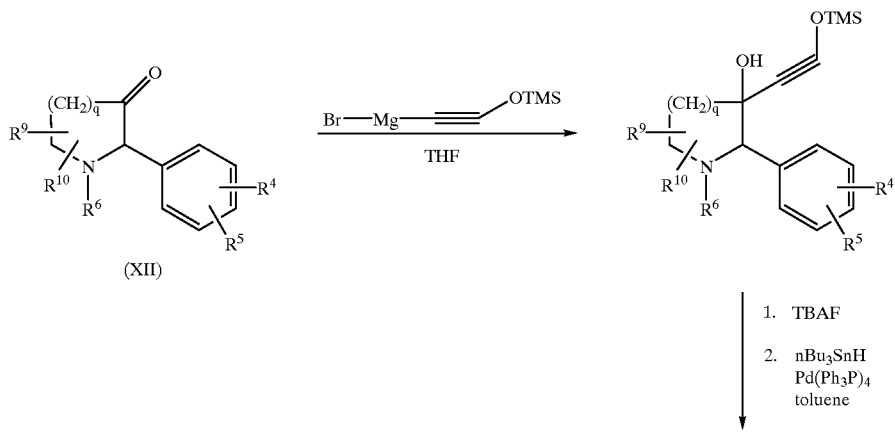

-continued

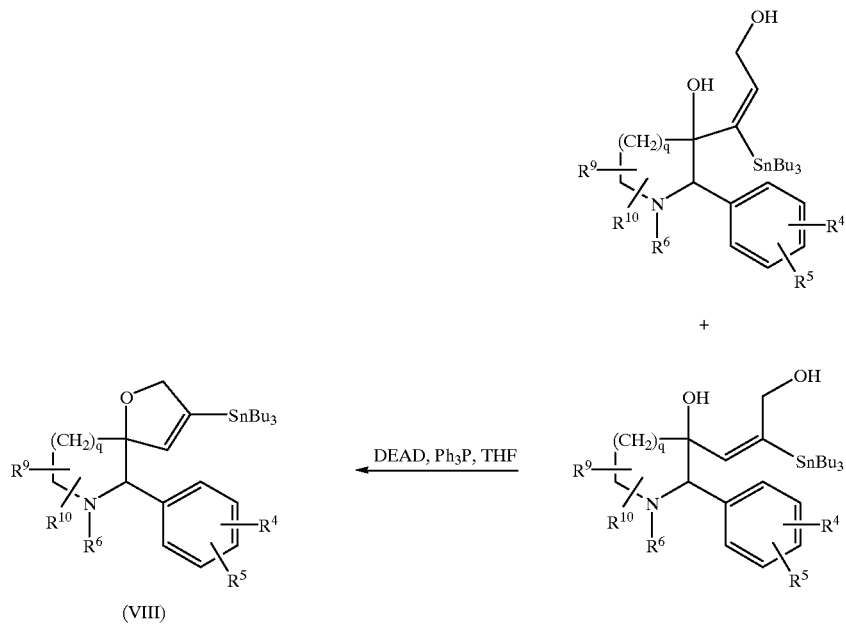

(VIII)

In a preferred embodiment of the aforementioned processes, $R^6$ is replaced with an amino protecting group, in particular tert-butyloxycarbonyl which is conveniently removed prior to reduction of the 7-aza-spiro[4.5]dec-3-ene structure (general process (A)).

In another preferred embodiment of the aforementioned processes, $R^6$ is a benzyl group. The reduction reaction described as process (A) above for the preparation of compounds of formula (I) may conveniently replace the benzyl group with a hydrogen atom. It will be appreciated from the discussion above that compounds of formula (I) wherein $R^6$ is a hydrogen atom are particularly preferred precursors to other compounds of formula (I).

Compounds of formula (IX) in which $R^3$ is an N-linked heterocyclic group may be prepared by conventional methodology, for example, from a compound of formula (XIII)

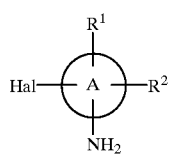

(XIII)

by reaction with a suitable anhydride of the formula $(R^{60}CO)_2O$, where $R^{60}$ is hydrogen or a desired substituent for the heterocycle, followed by reaction with triphenylphosphine in carbon tetrachloride, followed by the further step of (i) reaction with an azide such as sodium azide to effect the formation of a tetrazole ring; or (ii) reaction with hydrazine hydrate to effect the formation of a 1,2,4-triazole ring; or (iii) reaction with aminoacetaldehyde diethyl acetal to effect the formation of an imidazole ring.

Compounds of formula (XIII) may be prepared from the corresponding nitro compound by reduction using, for example, iron powder, or Raney nickel in a conventional manner.

The compounds of formula (XIII) or their nitro precursors are either known compounds or may be prepared using conventional methodology.

Intermediates of formula (VII) wherein Y" is —$CH_2CH_2$— may be prepared by the reduction of a compound of formula (XIV)

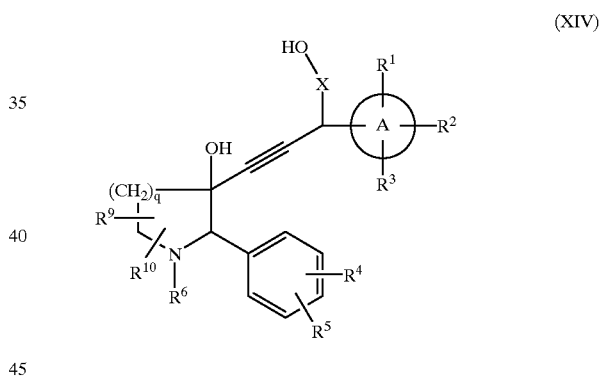

(XIV)

or a protected derivative thereof, using conventional methodology, for instance, by catalytic hydrogenation using a metal catalyst such as palladium or platinum or oxides thereof, preferably in a solvent such as an alcohol, e.g. ethanol, or an ester, e.g. ethyl acetate.

Compounds of formula (XIV) may be prepared by the reaction of a compound of formula (XII) with a compound of formula (XV)

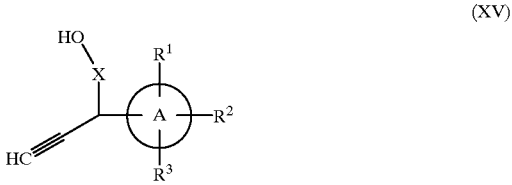

(XV)

or a protected derivative thereof, by lithiation using n-butyl lithium followed by quenching with, for example, sodium dihydrogen orthophosphate. The reaction is conveniently effected in a solvent such as an ether, e.g. tetrahydrofuran, at a reduced temperature, for example, at −78° C.

Compounds of formula (XII) may be prepared by methods described in European Patent Specification No. 0 577 394-A, or by analogous methods.

Compounds of formula (XV) are known compounds (see *Chemische Berichte*, (1988) 121, 1315–1320) or may be prepared by methods analogous to those described therein.

Compounds of formula (VI) are known compounds or may be prepared by conventional methods or using techniques analogous to those taught herein.

Compounds of formula (VII) may be prepared by the reaction of a compound of formula (XII) with a Grignard reagent of formula (XVII)

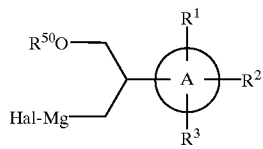

(XVII)

wherein $R^{50}$ is a suitable hydroxy protecting group, preferably benzyl, and Hal is a halogen atom, preferably chlorine, followed by removal of the protecting group $R^{50}$. Utilisation of a chiral intermediate of formula (XVII) is particularly suitable for controlling the stereochemistry of the 3-position in compounds of formula (I).

Compounds of formula (XVII) may be prepared by conventional methods well known in the art or based upon the methods described in the Examples herein.

In a further alternative method, compounds of formula (VII) may be prepared by the reduction of a compound of formula (XX)

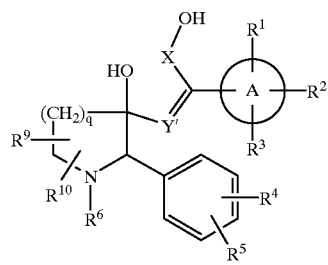

(XX)

using, for example, catalytic hydrogenation in the presence of a metal catalyst such as palladium or platinum or hydroxides or oxides thereof, preferably in a suitable solvent such as an alcohol, e.g. methanol, an ester, e.g. ethyl acetate, or an organic acid, e.g. acetic acid, or a mixture thereof.

Compounds of formula (XX) wherein Y' is —CH= may be prepared from a compound of formula (XXI)

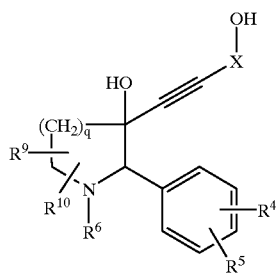

(XXI)

by reaction with a compound of formula (IX) using reductive Heck conditions as described in general process (F), above.

Compounds of formula (XXI) may be prepared from compounds of formula (XII) and, for example, a Grignard reagent prepared from O-trimethylsilylpropargyl alcohol using conventional methodology, followed by removal of the hydroxy protecting group.

According to another method, compounds of formula (VII) may be prepared from a compound of formula (XXII)

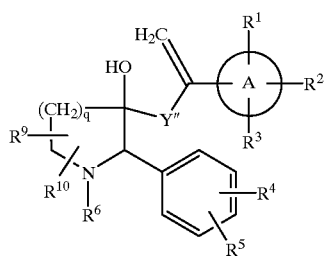

(XXII)

by reaction with borane in tetrahydrofuran, followed by an oxidative work-up using, for example, hydrogen peroxide and sodium hydroxide.

Compounds of formula (XXII) may be prepared from a compound of formula (XII) and, for example, a Grignard reagent prepared from a 2-aryl-3-bromo-1-propene using conventional methodology.

Compounds of formula (XVI) may be prepared, for example, by the conversion of a stannane of formula (VIII) to the corresponding iodide by treatment with iodine at reduced temperature, for example, at about −78° C., in a suitable solvent such as dichloromethane. The iodine may then be displaced to give the compound of formula (XVI) by treatment with, for example, α,α'-azo-isobutyronitrile and tributyltin hydride in a suitable solvent, for example, toluene, at an elevated temperature, for example, at about 100° C.

Alternatively, compounds of formula (XVI) may be prepared by the cyclisation of a compound of formula (XXIII)

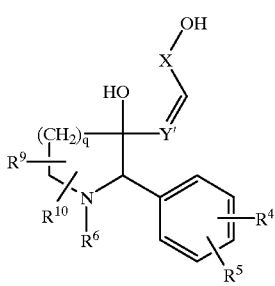

(XXIII)

using the cyclisation or dehydrating conditions described above for general process (D) above, or using diethyl azodicarboxylate and triphenylphosphine in a suitable solvent such as tetrahydrofuran.

Compounds of formula (XXIII) wherein Y' is —CH= may be prepared by the partial reduction of an acetylene compound of formula (XXI). The reaction is conveniently effected by catalytic hydrogenation using a metal catalyst such as palladium on calcium carbonate in the presence of a lead poison (e.g. Lindlar catalyst). Other suitable methods will be readily apparent to a person of ordinary skill in the art.

Compounds of formula (XXIV) may be prepared by the reaction of a compound of formula (XXV)

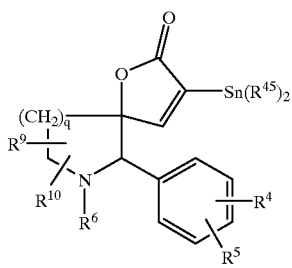

(XXV)

with a compound of formula (IX) according to general process (E), above, followed by reduction of only the C=C bond of the conjugated —C=C—C=O system using a reducing agent suitable for such a selective reduction. Suitable reducing agents are well known in the art (see, for instance, J. March, *Advanced Organic Chemistry*, 4th Edition, John Wiley & Sons, New York, 1992, pages 774–775). A particularly preferred reducing agent is sodium borohydride and nickel chloride in methanol.

Compounds of formula (XXV) may be prepared from a compound of formula (XXVI)

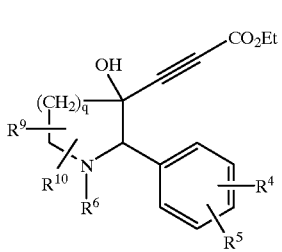

(XXVI)

by reaction with, for example, a trialkyltin hydride, such as tri-n-butyltin hydride, in the presence of a catalyst such as tetrakis(triphenylphosphine)palladium(0). Suitable solvents for this reaction include aromatic hydrocarbons, for example, toluene, conveniently at room temperature.

Compounds of formula (XXVI) may be prepared by the reaction of a compound of formula (XII) with ethyl propiolate in a suitable solvent, for example, an ether such as tetrahydrofuran, at a reduced temperature, for example, between −78° C. and −55° C.

Compounds of formula (XXVII) may be prepared by the oxidation of a compound of formula (XXVII)

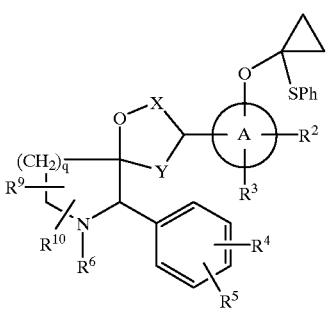

(XXVIII)

using a suitable oxidising agent such as oxone™ (potassium peroxymonosulfate) or sodium periodate. Most conveniently, where oxone™ is used, the reaction is effected on using a suspension with alumina in a suitable solvent such as a halogenated hydrocarbon, for example, chloroform. The reaction is effected at an elevated temperature, for example, at reflux.

Compounds of formula (XXVII) may be prepared from a compound of formula (I) in which $R^1$ is hydroxy by reaction with (1-iodo-cycloprop-1-yl)phenylsulfide (also known as 1-iodo-1-phenylthiocyclopropane).

It will be appreciated that compounds of the formula (I) wherein $R^6$ contains an =O or =S substituent can exist in tautomeric forms. All such tautomeric forms and mixtures thereof are included within this invention. Most aptly the =O or =S substituent in $R^6$ is the =O substituent.

Where they are not commercially available, the intermediates of formula (IV) above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 1 μM on said test method.

For the avoidance of doubt, the nomenclature adhered to throughout this specification follows the general principle illustrated below:

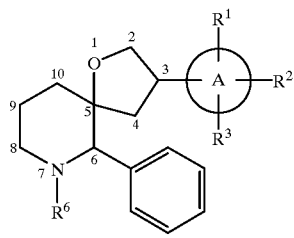

The following non-limiting Examples serve to illustrate the preparation of compounds of the present invention:

Description 1

(3S)-1-tert-Butyloxycarbonyl-2-phenylpiperidin-3-one

To a cooled (−60° C.) solution of oxalyl chloride (0.68 ml, 7.8 mmol) in dicloromethane (17 ml) was added dimethyl sulphoxide (0.69 ml, 9.8 mmol) for 10 minutes before addition of (2S,3S)1-tert-butyloxycarbonyl-3-hydroxy-2-phenylpiperidine (1.8 g, 6.5 mmol; prepared by the method described in European Patent Specification number 0 528 495-A) in dicloromethane (7 ml). The solution was stirred at −60° C. for 20 minutes, warmed to −30° C. and triethylamine (2.5 ml) added. The solution was warmed to room temperature then was washed with ice cold 10% aqueous citric acid solution (40 ml, twice), water and dried MgSO$_4$). This material was used without purification on silica (enantiomeric excess >90%, chiral hplc).

Description 2

(2S,3R)-1-tert-Butyloxycarbonyl-3-(3-hydroxypropyn-1yl)-2-phenylpiperidin-3-ol

To a cooled (−5° C.) solution of ethylmagnesium bromide (1M in tetrahydrofuran, 130 ml, 130 mmol) in tetrahydrofuran was added O-trimethylsilylpropargyl alcohol slowly. The reaction was stirred at 0° C. for 20 minutes and then at room temperature for 2 hours, before cooling to −10° C. To this was then added a solution of (2S)-1-tert-butyloxycarbonyl-2-phenylpiperidin-3-one (Desc. 1; 30 g, 108 mmol) in tetrahydrofuran keeping the temperature below 5° C. The reaction was stirred at room temperature overnight, quenched by addition of water/saturated aqueous ammonium chloride (200 ml/200 ml) and extracted with ethyl acetate (2×200 ml). The combined organic phases were dried (MgSO$_4$) and evaporated to an oil. This oil was dissolved in ethyl acetate (400 ml) and a solution of tetrabutylammonium fluoride (1M in tetrahydrofuran, 130 ml, 130 mmol) added. After stirring at room temperature for 2 hours, water (200 ml) was added, and the two layers separated. The aqueous phase was further extracted with ethyl acetate (200 ml), the organic layers dried (MgSO$_4$) and evaporated to give the product as an oil (50 g) which was used crude for Description 3. $^1$H NMR (CDCl$^3$) δ7.53–7.55 (2H, m), 7.19–7.35 (3H, m) 5.56 (1H, s), 4.27 (2H, s), 3.99–4.03 (1H, m) 3.25 (1H, bs), 2.77–2.81 (1H, m) 2.77 (1H, bs), 2.12–2.20 (1H, m) 1.91–1.99 (2H, m), 1.77–1.83 (1H, m), 1.39 (9H, s).

Description 3

(5R,6S)-3-Tributylstannyl-6-phenyl-1-oxa-7-(tert-butyloxycarbonyl)-7-aza-spiro[4.5]dec-3-ene To a solution of (2S,3R)-1-t-butyloxycarbonyl-3-(3-hydroxypropyn-1-yl)-2-phenylpiperidin-3-ol (Desc. 2; 50 g) and tetrakis(triphenylphosphine)palladium (0) (2 g, 1.7 mmol) in toluene (600 ml) was added tributyltin hydride (29 ml, 108 mmol) dropwise. The reaction was stirred at room temperature for 2 hours, after which the solvent was evaporated to give a mixture of the two regioisomeric stannanes, (2S,3R)-1-t-butyloxycarbonyl-3-(3-hydroxy-2-tributylstannylpropen-1yl)-2-phenylpiperidin-3-ol and (2S,3R)-1-t-butyloxycarbonyl-3-(3-hydroxy-1-tributylstannylpropen-1yl)-2-phenylpiperidin-3-ol, as an oil. This oil was dissolved in tetrahydrofuran (600 ml), triphenylphosphine (26.2 g, 100 mmol) added, and a solution of diethyl azodicarboxylate (15.7 ml, 100 mmol) in tetrahydrofuran (50 ml) added dropwise. The reaction was stirred at room temperature for 1 hour, the solvent evaporated, the residue dissolved in acetonitrile (500 ml) and extracted with hexane (6×100 ml). The combined hexane layers were evaporated and the residue chromatographed on silica, eluting with 2% ethyl acetate in dichloromethane, to yield first the title compound, (5R,6S)-3-trylibutylstannyl-6-phenyl-1-oxa-7-(tert-butyloxycarbonyl)-7-aza-spiro[4.5]dec-3-ene as an oil (25 g) $^1$H NMR (CDCl$_3$) δ7.38–7.40 (2H, m) 7.15–7.25 (3H, m), 5.96 (1H, t, J=2.3 Hz), 4.93 (1H, s), 4.63 (1H, dd, J=2.23 and 12.9 Hz), 4.22 (1H, dd, J=2.23 and 12.9 Hz), 4.09–4.14 (1H, m), 3.09–3.17 (1H, m), 1.95–1.99 (1H, m), 1.83–1.86 (1H, m), 1.72–1.76 (2H, m), 1.40–1.51 (6H, m) 1.38 (9H, s), 1.25–1.32 (6H, m), 0.86–0.99 (15H, m), followed by some mixed fractions (6 g) and lastly the other regioisomer (5R,6S)-4-tributylstannyl-6-phenyl-1-oxa-7-(tert-butyloylxcarbonyl)-7-aza-spiro[4.5]dec-3-ene (3 g).

Description 4

2-Bromo-3-methoxypyridine

2-Bromo-2-pyridinol (15 g, 86 mmol) in acetone (500 ml) was treated with potassium carbonate (23.8 g, 172 mmol) and iodomethane (8.1 ml, 130 mmol) and the suspension was refluxed at 70° C. for 16 hours. Once cooled, the mixture was filtered and the filtrate concentrated in vacuo. The residue was then purified by silica wet flash chromatography to give the product as yellow crystals (12.4 g, 66 mmol, 77% yield).

$^1$H NMR (250 MHz, CDCl$_3$) δ7.99 (1H, dd, J=1.57 Hz and 4.57 Hz), 7.23 (1H, dd, J=4.57 Hz and 8.25 Hz), 7.15 (1H, dd, J=1.57 Hz and 8.25 Hz), 3.93 (3H, s).

Description 5

2-Bromo-3-methoxy-6-nitropyridine

2-Bromo-3-methoxypyridine (Desc. 4; 12.4 g, 66 mmol) in concentrated sulphuric acid (30 ml) was treated dropwise with fuming nitric acid (5.5 ml), and the solution heated at 60° C. for 2 hours. After cooling the solution was poured onto ice (500 ml). The solid formed was recovered by filtration, washed with water (500 ml) and sodium bicarbonate solution (500 ml) to give the title product as a yellow solid (10.0 g, 43 mmol, 65% yield).

$^1$H NMR (250 MHz, CDCl$_3$) δ8.27 (1H, d, J=8.26 Hz), 7.32 (1H, d, J=8.26 Hz), 4.07 (3H, s).

Description 6

2-Bromo-3-methoxy-6aminopyridine

2-Bromo-3-methoxy-6-nitropyridine (Desc. 5; 9.0 g, 38.6 mmol) and platinum (IV) oxide hydrate (250 mg) in ethyl acetate (250 ml) was hydrogenated at 20 psi hydrogen for 1 hour. The catalyst was removed by filtration and the filtrate concentrated to give the product as a yellow solid (7.73 g, 38.1 mmol, 99% yield).

$^1$H NMR (250 MHz, CDCl$_3$) δ7.27 (1H, d, J=8.68 Hz), 6.42 (1H, d, J=8.68 Hz), 5.89 (2H, br s), 3.36 (3H, s).

Description 7

2-Bromo-3-methoxy-6-trifluoroacetamidopyridine

2-Bromo-3-methoxy-6-aminopyridine (Desc. 6; 1.0 g, 4.9 mmol) in dichloromethane (25 ml) was treated with N,N-diisopropylethylamine (2.2 ml, 12.3 mmol) and the solution cooled to 0° C. Trifluoroacetic acetic anhydride (770 μl, 5.4 mmol) was then added dropwise and the solution stirred to 22° C. over 2 hours. The mixture was then poured into saturated sodium bicarbonate solution (25 ml) and extracted with dichloromethane (25 ml). The extracts were dried (MgSO$_4$) and concentrated in vacuo. The residue was purified by flash silica chromatography to give the product as a white solid (890 mg, 3.0 mmol, 61% yield).

$^1$H NMR (250 MHz, DMSO-d$_6$) δ12.14 (1H, br s), 7.92 (1H, d, J=8.75 Hz), 7.67 (1H, d, J=8.75 Hz), 3.91 (3H, s).

Description 8

2-Bromo-3-methoxy-6-N-methylaminopyridine

2-Bromo-3-methoxy-6trifluoroacetamidopyridine (Desc. 7; 1.0 g, 3.3 mmol) and potassium carbonate (910 mg, 6.6 mmol) were taken up in N,N-dimethylformamide (20 ml) and treated with iodomethane (410μl, 6.6 mmol). The suspension formed was stirred at 22° C. for 16 hours then poured into water (100 ml). This solution was extracted with ethyl acetate (2×100 ml) and the extracts dried (MgSO$_4$) and concentrated in vacuo. The residue was then taken up in 5% methanolic potassium carbonate solution (50 ml) and stirred for 15 minutes at 22° C. The solvent was removed in vacuo and the residue partitioned between water (50 ml) and ethyl acetate (50 ml). The organic layer was dried (MgSO$_4$) and concentrated to give the product as a yellow solid (680 mg, 3.13 mmol, 95% yield).

$^1$H NMR (250 MHz, DMSO-d$_6$) δ7.32 (1H, d, J=8.71 Hz), 6.43 (1H, br s), 6.41 (1H, d, J=8.75 Hz), 3.71 (3H, s), 2.68 (3H, d, J=4.90 Hz).

Description 9

2-Bromo-3-methoxy-6-N-methyltrifluoromethanesulfonamidopyridine

2-Bromo-3-methoxy-6-N-methylaminopyridine (Desc. 8; 680 mg, 3.1 mmol) in dichloromethane (50 ml) was treated with N,N-diisopropylethylamine (1.08 ml, 6.2 mmol) and the solution cooled to 0° C. Trifluoromethane sulfonic anhydride (622 μl, 3.7 mmol) was then slowly added and the resultant mixture stirred at 0° C. for 1 hour, then at 22° C. for 1 hour. The solution was washed with saturated sodium bicarbonate solution (50 ml), dried (MgSO$_4$) and concentrated in vacuo. The residue was purified by flash silica chromatography to give the product as a yellow gum (838 mg, 2.4 mmol, 77% yield).

$^1$H NMR (250 MHz, CDCl$_3$) δ7.40 (1H, d, J=8.54 Hz), 7.18 (1H, d, J=8.54 Hz), 3.94 (3H, s), 3.53 (3H, quartet, J=1.14 Hz).

Description 10

2-Bromo-3-methoxy-6-(5-trifluoromethyl-1,2,3,4-tetrazol-1-yl)pyridine

2-Bromo-3-methoxy-6-trifluoroacetamidopyridine (Desc. 7; 890 mg, 3.0 mmol) and triphenylphosphine (2.4 g, 9.0 mmol) were refluxed in tetrachloromethane (24 ml) for 4 hours. The solvent was removed in vacuo, and the chloroimidate formed taken up in N,N'-dimethylformamide (6 ml) and treated with sodium azide (325 mg, 5.0 mmol). This mixture was heated at 70° C. for 3 hours, then cooled and concentrated in vacuo. The residue was taken up in saturated sodium bicarbonate solution (50 ml) and extracted with ethyl acetate (2×50 ml). The extracts were dried (MgSO$_4$) and concentrated, and the residue purified by silica chromatography to give the product as a brown solid (187 mg, 0.58 mmol, 19% yield).

$^1$H NMR (250 MHz, CDCl$_3$) δ7.81 (1H, d, J=8.55 Hz), 7.40 (1H, d, J=8.55 Hz), 4.05 (3H, s).

Description 11

2-Bromo-3-methoxy-6-(2-trifluoromethylimidazol-1-yl)pyridine

2-Bromo-3-methoxy-6trifluoroacetamidopyridine (Desc. 7; 1.78 g, 6.0 mmol) and triphenylphosphine (3.2 g, 12.0 mmol) were refluxed in tetrachloromethane (24 ml) for 4 hours. The solvent was removed in vacuo, and the chloroimidate formed taken up in tetrahydrofuran (50 ml) and cooled to 0° C. Aminoacetaldehyde diethyl acetal (2.6 ml, 18.0 mmol) was added dropwise and the mixture stirred to 22° C. over 2 hours. The solvent was removed in vacuo and the residue taken up in acetic acid (50 ml). This mixture was refluxed for 1 hour and then concentrated. The residue was basified with saturated sodium bicarbonate solution (250 ml) and extracted with ethyl acetate (2×250 ml). The extracts were dried (Na$_2$SO$_4$) and concentrated, and the crude product purified by silica flash chromatography, followed by recrystallisation from ethyl acetate, to give the imidazole as white crystals (923 mg, 2.9 mmol, 48% yield).

$^1$H NMR (250 MHz, CDCl$_3$) δ7.22–7.40 (4H, 4 doublet signals), 4.01 (3H, s).

Description 12a

2-Methoxy-5-trifluoromethylpyridine

To methanol (40 ml) was added sodium (0.74 g, 32.1 mmol) followed by a solution of 2-chloro-5-trifluoromethoxypyridine (5.0 g, 27.5 mmol), and the mixture formed refluxed for 12 hrs. More sodium (0.74 g, 32.1 mmol) was added and again the mixture was refluxed for 3 hrs. After concentration the residue was partitioned between water (20 ml) and ethyl acetate (40 ml), and the organic phase washed with brine (20 ml). After drying (Na$_2$SO$_4$) the solution was concentrated to give the product (2.68 g).

H$^1$ NMR δ(250 MHz, CDCl$_3$): 8.45 (1H, d, J 2.3 Hz), 7.76 (1H, dd, J 2.3 Hz and 8.4 Hz), 6.82 (1H, d, J 8.4 Hz), 3.98 (3H, s).

Description 12b

2-Methoxy-3-trimethylsilyl-5-trifluoromethylpyridine

To butyl lithium (7.2 ml, 1.6M in hexanes, 11.5 mmol) in tetrahydrofuran (12.0 ml) at −78° C. was slowly added diisopropylamine (1.14 g, 11.3 mmol) in tetrahydrofuran (4.0 ml), and the resulting solution allowed to warm to 0° C. over 45 mins. A mixture of 2-methoxy-5-trifluoromethylpyridine (2.00 g, 11.3 mmol) and trimethylsilyl chloride (3.2 ml, 25.2 mmol) in tetrahydrofuran (8.0 ml) was then slowly added and the mixture stirred for 30 mins. at 0° C., before being quenched with water (50 ml).

The mixture formed was extracted with ethyl acetate (2×70 ml), and the extracts washed with brine (50 ml), dried (Na$_2$SO$_4$) and concentrated to give the product as an orange oil (1.36 g, 48% yield).

H$^1$ NMR δ(360 MHz, CDCl$_3$): 8.26 (1H, d, J 2.6 Hz), 7.62 (1H, d, J 2.6 Hz), 3.97 (3H, s).

Description 12c

3-Iodo-2-methoxy-5-trifluoromethylpyridine

2-Methoxy-3-trimethylsilyl-5-trifluoromethylpyridine (1.30 g, 5.21 mmol) in methanol (15 ml) was treated with silver tetrafluoroborate (1.22 g, 6.27 mmol), cooled to 0° C. and then iodine (1.32 g, 5.20 mmol) in methanol (25 ml) was slowly added. The solution was stirred at 0° C. for 4 hrs then at 22° C. for 16 hrs, before being refluxed for 8 hrs. After cooling, dichloromethane (50 ml) was added and the solution was washed with sodium thiosulphate solution (30 ml), brine (50 ml), then dried (Na$_2$SO$_4$) and concentrated to give a 1:1 mixture of the product and starting material as an oil (1.23 g).

H$^1$ NMR δ(250 MHz, CDCl$_3$): 8.10–8.11 (2H, m), 7.92 (1H, d, J 1.9 Hz), 7.49 (1H, d, J 2.3 Hz), 3.75 (3H, s), 3.69 (3H, s).

Description 13

3-Bromo-2-dimethylamino-5-trifluoromethylpyridine

2-Chloro-3-bromo-5-trifluoromethylpyridine (509 mg, 1.95 mmol) was treated with ethanolic dimethylamine solution (10 ml) and heated at reflux for 2 hrs before being concentrated. The residue was partitioned between water (10 ml) and ethyl acetate (10 ml), and the organic phase washed with brine (10 ml) and dried (Na$_2$SO$_4$). The solution was then concentrated to give the product as a yellow oil (430 mg, 82% yield).

H$^1$ NMR δ(250 MHz, CDCl$_3$): 8.37 (1H, d, J 2.1 Hz), 7.90 (1H, d, J 2.1 Hz), 3.11 (6H, s).

Description 14

3-Bromo-2-hydroxy-5-trifluoromethylpyridine

5-Trifluoromethyl-2(1H)-pyridone (10.0 g) and sodium acetate (5.25 g, 64 mmol) in acetic acid (100 ml) was treated with bromine (3.3 ml, 63 mmol) and heated at 80° C. for 2 hrs, before being cooled and concentrated. The residue was basified with sodium hydrogen carbonate solution (250 ml) and extracted with ethyl acetate (2×250 ml). The extracts were dried (MgSO$_4$) and concentrated to give the product as a tan solid (14.22 g, 96% yield).

H$^1$ NMR δ(250 MHz, d$_6$-DMSO): 12.60 (1H, br s), 8.23 (1H, d, J 2.4 Hz), 8.05 (1H, d, J 2.4 Hz).

Description 15

2-Chloro-3-bromo-5-trifluoromethylpyridine

To phosphorous oxychloride (2.02 ml, 21.6 mmol) was added quinoline (1.34 ml, 11.2 mmol) followed by 3-bromo-2-hydroxy-5-trifluoromethylpyridine (5.0 g, 20.7 mmol), and the mixture formed heated at 120° C. for 3 hrs. It was then cooled to 100° C. and water (10 ml) added. After cooling to 22° C., sodium hydrogen carbonate solution (100 ml) was added and the mixture extracted with ethyl acetate (2×100 ml). The extracts were dried (MgSO$_4$) and concentrated, and the residue purified by silica chromatography to give the product as an oil (4.05 g, 75% yield).

H$^1$ NMR δ(250 MHz, CDCl$_3$): 8.63 (1H, d, J 2.2 Hz), 8.17 (1H, d, J 2.2 Hz).

Description 16

3-Bromo-2-(2',2',2'-trifluoroethoxy)-5-trifluoromethylpyridine

To 2,2,2-trifluoroethanol (1.4 ml 19.2 mmol) in tetrahydrofuran (3 ml) was added sodium hydride (760 mg, 60% suspension in oil, 19.0 mmol) and the suspension was stirred at 22° C. for 20 mins. 2-Chloro-3-bromo-5-trifluoromethylpyridine (1.0 g, 3.84 mmol) in tetrahydrofuran (2 ml) was then added and the mixture stirred for 16 hrs at 22° C., before being poured into water (100 ml) and extracted with ethyl acetate (2×100 ml). The extracts were dried (MgSO$_4$) and concentrated to give the product as an oil (776 mg, 62% yield).

H$^1$ NMR δ(250 MHz, CDCl$_3$): 8.38 (1H, d, J 2.1Hz), 8.10 (1H, d, J 2.1 Hz), 4.86 (2H, q, J 8.3 Hz).

Description 17

3-Bromo-2-hydroxy-5-nitropyridine

2-Hydroxy-5-nitropyridine (10.0 g, 71 mmol) in chloroform (200 ml) and acetic acid (10 ml) was treated with bromine (3.7 ml, 72 mmol) and then refluxed for 24 hrs. More bromine (3.7 ml, 72 mmol) was added and the mixture refluxed for a further 48 hrs, then cooled. Ethyl acetate (150 ml) was added and the solid formed removed by filtration, washed with ethyl acetate (50 ml) and dried to give the product as an off-white powder (8.5 g).

H$^1$ NMR δ(250 MHz, CDCl$_3$); 8.58 (2H, 2d, J 2.4 Hz).

Description 18

3-Bromo-2-chloro-5-nitropyridine

3-Bromo-2-hydroxy-5-nitropyridine (8.5 g, 39 mmol) and N,N'-dimethylformamide (0.5 ml) in chloroform (75 ml) were treated dropwise with phosphorous oxychloride (7.3 ml, 80.2 mmol) and heated at reflux for 24 hrs. The mixture was then cooled and concentrated, before being partitioned between ethyl acetate (80 ml) and sodium hydrogen carbonate solution (50 ml). The organic phase was washed with brine (100 ml), dried Na$_2$SO$_4$) and concentrated to give the product as a yellow solid (8.88 g).

H$^1$ NMR δ(360 MHz, CDCl$_3$); 9.17 (1H, d, J 2.5 Hz), 8.72 (1H, d, J 2.5 Hz).

Description 19

3-Bromo-2-chloro-5-trifluoroacetamidopyridine

3-Bromo-2-chloro-5-nitropyridine (0.51 g, 2.15 mmol) and trifluoroacetic anhydride (0.25 ml) in ethyl acetate (5.0 ml) were hydrogenated over platinum oxide (101 mg) at 10 psi hydrogen for 30 mins, then filtered. The filtrate was treated with N,N'-diisopropylethylamine (0.25 ml) and stirred for 30 mins., before being concentrated. The residue was purified by silica chromatography to give the product as an orange solid (0.53 g).

H$^1$ NMR δ(250 MHz, CDCl$_3$); 8.56 (1H, d, J 2.5 Hz), 8.46 (1H, d, J 2.5 Hz), 8.15 (1H, br s).

Description 20

3-Bromo-2-chloro-5-(2-trifluoromethylimidazol-1-yl)pyridine

3-Bromo-2-chloro-5-trifluoroacetamidopyridine (0.53 g, 1.75 mmol) and triphenylphosphine (550 mg, 2.10 mmol) in carbon tetrachloride (50 ml) was refluxed for 16 hrs and then cooled to 0° C. Aminoacetaldehyde diethyl acetal (0.25 ml, 1.72 mmol) was added and the mixture stirred at 0° C. for 1 hr, then at 22° C. for 2 hrs. After concentration in vacuo, acetic acid (4 ml) was added and the mixture refluxed for 7 hrs, then cooled. Ethyl acetate (20 ml) was added and the resulting solution was washed with sodium hydroxide solution (50 ml, 2M) and brine (50 ml) before being dried ($MgSO_4$) and concentrated. The residue was purified by silica chromatography to give the product as yellow solid (104 mg).

H[1] NMR δ(250 MHz, $CDCl_3$); 8.43 (1H, d, J 2.4 Hz), 8.01 (1H, d, J 2.4 Hz), 7.30 (1H, d, J 1.2 Hz), 7.17 (1H, d, J 1.2 Hz).

Description 21

3-Bromo-2-(2',2',2'-trifluoroethoxyly)-5-(2-trifluoromethylimidazol-1-yl)pyridine 3-Bromo-2-chloro-5-(2-trifluoromethylimidazol-1-yl) pyridine (490 mg, 1.50 mmol) in 2,2,2-trifluoroethanol (10 ml) was treated with sodium hydride (300 mg, 60% dispersion in oil, 7.83 mmol) and refluxed for 30 hrs. Another portion of sodium hydride was added (300 mg, 60% dispersion in oil, 7.83 mmol) and the mixture refluxed for a further 48 hrs, then cooled. Aqueous ammonium chloride solution (20 ml) was added and the mixture extracted with ethyl acetate (2×20 ml). The extracts were washed with brine (40 ml), dried (Na2SO4) and concentrated, before the residue was purified by silica chromatography, to give the product as a pale yellow solid (344 mg, 59% yield).

H[1] NMR δ(250 MHz, $CDCl_3$): 8.16 (1H, d, J 2.4 Hz), 7.94 (1H, d, J 2.4 Hz), 7.27 (1H, d, J 1.2 Hz), 7.14 (1H, d, J 1.2 Hz), 4.86 (2H, q, J 8.2 Hz).

Description 22

3-Bromo-2-methoxy-5-(2-trifluoromethylimidazol-1-yl)pyridine

3-Bromo-2-chloro-5-(2-trifluoromethylimidazol-1-yl) pyridine (318 mg, 0.97 mmol) in methanol (12 ml) was treated with sodium hydride (54 mg, 60% dispersion in oil, 1.41 mmol) and refluxed for 3 hrs. After cooling and concentration, the residue was purified by silica chromatography, to give the product as a yellow solid (252 mg, 80% yield).

H[1] NMR δ(250 MHz, $CDCl_3$); 8.16 (1H, d, J 2.4 Hz), 7.84 (1H, d, J 2.4 Hz), 7.25 (1H, d, J 1.2 Hz), 7.12 (1H, d, J 1.2 Hz), 4.08 (3H, s).

Description 23

3-Bromo-2-(2propyl)oxy-5-trifluoromethylpyridine

2-Bromopropane (0.78 ml, 8.3 mmol) was added to a stirred suspension of 3-bromo-5-trifluoromethyl-2(1H)-pyridone (2.0 g, 8.3 mmol) and silver carbonate (1.16 g, 4.2 mmol) in hexane (40 ml) and the mixture stirred at 50° C. for 14 h, then at reflux for 3 h. More 2-bromopropane (0.78 ml) was added and reflux resumed for a further 3 h. On cooling, the mixture was filtered, the filtrate diluted with hexane (100 ml) and washed with water (50 ml). The organic layer was dried ($Na_2SO_4$), evaporated, and the residual oil subjected to column chromatography over silica gel, eluting with ethyl acetate/hexane (5:95) to leave the product as a colourless oil (1.68 g).

H[1] NMR δ(250 MHz, $CDCl_3$): 8.34–8.35 (1H, m), 7.99–8.00 (1H, m), 5.39 (1H, heptet, J 6.2 Hz), 1.41 (6H, d, 6.2 Hz).

Description 24

3-Bromo-2-ethoxy-5-trifluoromethylpyridine

Iodoethane (1.33 ml, 16.6 mmol) was added to a suspension of 3-bromo-5-trifluoromethyl-2(1H)-pyridone (2.0 g, 8.3 mmol) and silver carbonate (1.16 g, 4.2 mmol) in hexane (50 ml) and the mixture stirred for 64 h at room temperature. The resulting suspension was filtered, the filtrate evaporated and the residue purified by chromatography on silica gel to give the product as a colourless oil (1.34 g).

H[1] NMR δ(250 MHz, $CDCl_3$): 8.36 (1H, dd, J 1.0 Hz and 2.1 Hz), 8.00 (1H, d, J 2.1 Hz), 4.50 (2H, q, J 7.1 Hz), 1.45 (3H, t, J 7.1 Hz).

Description 25

3-Bromo-2-(2-methoxy)ethoxy-5-trifluoromethylpyridine

To a stirred suspension of sodium hydride (60% dispersion in oil; 1.0 g, 25 mmol) in tetrahydrofuran (5 ml) was added 2-methoxyethanol (2.17 ml, 27.6 mmol). Once effervesence had subsided, a solution of 3-bromo-2-chloro-5-trifluoromethylpyridine in tetrahydrofuran was added dropwise and the mixture stirred for 2 h. The residue remaining on removal of solvent was partitioned between water (20 ml) and diethyl ether (20 ml), the organic layer washed with brine, dried ($Na_2SO_4$), evaporated, and the remianing oil purified by silica gel chromatography, eluting with hexane/ EtOAc (9:1), to afford the product as a pale yellow oil (1.51 g).

H[1] NMR δ(250 MHz, $CDCl_3$): 8.35 (1H, dd, J 1.0 Hz and 2.1 Hz), 8.02 (1H, d, J 2.1 Hz), 4.57–4.61 (2H, m) 3.78–3.82 (2H, m), 3.46 (3H, s).

Description 26

3-Bromo-5-trifluoromethyl-2(1H)-pyridone

To 5-trifluoromethyl-2(1H)-pyridone (10.0 g, 61.3 mmol) and sodium acetate (5.25 g, 64 mmol) in acetic acid (100 ml) was added bromine (3.3 ml, 63 mmol) and the solution stirred at 80° C. for 2 hrs. After concentration in vacuo, the residue was suspended in saturated sodium bicarbonate solution (500 ml) and extracted with ethyl acetate (2×50 ml). The extracts were dried ($MgSO_4$) and concentrated to give the product as a tan solid (14.22 g, 58.8 mmol, 96% yield).

H[1] NMR δ(250 MHz, $d_6$-DMSO): 12.74 (1H, br s), 8.23 (1H, d, J 2.3 Hz), 8.05 (1H, d, J 2.3 Hz)

Description 27

3-Bromo-2-chloro-5-trifluoromethylpyridine

To phosphorous oxychloride (2.02 mL, 21.6 mmol) was added quinoline (1.34 mL, 11.2 mmol) followed by 3-bromo-5-trifluoromethyl-2(1H)-pyridone (5.0 g, 20.07 mmol). The mixture was heated at 120° C. for 3 hrs, then cooled to 100° C., whn water (10 mL) was carefully added. After cooling to room temperature, saturated sodium bicarbonate was added (100 mL) and the mixture extracted with ethyl acetate (2×100 mL). The extracts were dried ($MgSO_4$) and concentrated, and the residue purified by silica chromatography to give the product as a liquid (4.05 g, 15.5 mmol, 75% yield).

H[1] NMR δ(250 MHz, $CDCl_3$): 8.34 (1H, d, J 2.1 Hz) 8.17 (1H, d, J 2.1 Hz)

Description 28

3-Bromo-2-(2',2',2'-trifluoroethoxy)-5-trifluoromethylpyridine

To 2,2,2-trifluoroethanol (1.4 mL, 19.2 mmol) in tetrahydrofuran (3 mL) was added sodium hydride (60% suspension in oil, 760 mg, 19.0 mmol) and the suspension formed was stirred for 20 minutes. 3-Bromo-2-chloro-5-trifluoromethylpyridine (1.0 g, 3.84 mmol) was then added and the solution stirred at room temperature for 16 hrs. Water (100 mL) was added and the mixture formed was extracted with ethyl acetate (2×100 mL). The extracts were dried (MgSO$_4$) and concentrated to give the product as an oil (776 mg, 2.4 mmol, 62% yield).

H$^1$ NMR δ(250 MHz, CDCl$_3$): 8.38 (1H, d, J 2.1 Hz), 8.17 (1H, d, J 2.1 Hz), 486 (2H, q, J 8.2 Hz)

Description 29

3-Bromo-2-methoxy-5-trifluoromethylpyridine

To a suspension of 3-bromo-5-trifluoromethyl-2(1H)-pyridone (2.0 g, 8.26 mmol) and silver carbonate (2.32 g, 8.4 mmol) in hexane (50 mL) was added iodomethane (1.05 mL, 16.8 mmol) and the resulting mixture heated at reflux for 16 hrs. The suspension was cooled, and filtered, and the filtrate concentrated in vacuo. The residue was purified by silica chromatography to give the product as an oil (893 mg, 3.49 mmol, 42% yield).

H$^1$ NMR δ(250 MHz, CDCl$_3$) 7.88 (1H, d, J 2.4 Hz) 7.71 (1H, d, J 2.4 Hz) 3.66 (3H, s)

Description 30

2-Benzyloxy-3-bromo-5-trifluoromethylpyridine

3-Bromo-5-trifluoromethyl-2(1H)-pyridone (6.09 g, 25.2 mmol) and silver carbonate (7.18 g, 26.0 mmol) were suspended in hexane (200 mL) and treated with benzyl bromide (6 mL, 50.3 mmol). The mixture was stirred for 18 hrs, then filtered. The filtrate was concentrated and the residue purified by silica chromatography to give the product as a white solid (7.65 g, 23 mmol, 91% yield).

H$^1$ NMR δ(250 MHz, CDCl$_3$): 8.38 (1H, d, J 2.1 Hz), 8.03 (1H, d, J 2.1 Hz), 7.25–7.50 (5H, m), 5.51 (2H, s)

Description 31

(3R,5R,6S)-3-[2-(1-Phenylthiocyclopropyloxy)-5-trifluoromethyl pyridin-3-yl]-6-phenyl-1-oxa-7-(tert-butyloxycarbonyl)-7-azaspiro[4.5]decane (3R,5R,6S)-3-(2-Hydroxy-5-trifluoromethylpyridin-3-yl)-6-phenyl-1-oxa-7-(tert-butyloxycarbonyl)-7-azaspiro[4.5]decane (500 mg, 1.05 mmol) and silver carbonate (521 mg, 1.89 mmol) in toluene (20 mL) was treated with 1-iodo-1-phenylthiocyclopropane (526 mg, 1.89 mmol) and stirred for 18 hrs. The suspension was filtered and the filtrate concentrated. The residue was then purified by silica chromatography to give the product as a white foam (566 mg, 0.90 mmol, 86% yield).

H$^1$ NMR δ(250 MHz, CDCl$_3$): 8.48 (1H, d, J 2.2 Hz), 7.71 (1H, d, J 2.2 Hz), 7.57–7.60 (2H, m), 7.43–7.47 (2H, m), 7.21–7.38 (4H, m), 5.32 (1H, br s) 4.24 (1H, dd, J 7.4 and 8.4 Hz), 3.93–3.98 (1H, m), 3.80 (1H, t, J 8.1 Hz), 3.60–3.70 (1H, m), 2.78 (1H, dt, J 3.4 and 12.7 Hz), 2.17–2.28 (1H, m), 1.86 (1H, dd, J 9.5 and 12.6 Hz), 1.56–1.71 (3H, m), 1.43–1.49 (13H, m)

Description 32

(3R,5R,6S)-3-[2-(1-Phenylsulfonylcyclopropyloxy)-5-trifluoromethylpyridin-3-yl]-6-phenyl-1-oxa-7-(tert-butyloxycarbonyl)-7-azaspiro[4.5]decane To (3R,5R,6S)-3-[2-(1-phenylthiocyclopropyloxy)-5-trifluoromethyl pyridin-3-yl]-6-phenyl-1-oxa-7-(tert-butyloxycarbonyl)-7-azaspiro[4.5]decane (410 mg, 0.65 mmol) in chloroform (5 mL) was added alumina (650 mg) and Oxone® (1.20 g, 1.95 mmol), and the suspension was refluxed for 24 hrs. The solid material was removed by filtration, and washed well with chloroform (50 mL). The combined filtrates were concentrated and the residue purified by silica chromatography to give the product as a gum (423 mg, 0.64 mmol, 99% yield).

H$^1$ NMR δ(250 MHz, CDCl$_3$): 8.01 (1H, d, J 2.2 Hz), 7.76–7.79 (2H, m), 7.70 (1H, d, J 2.2 Hz), 7.54–7.61 (3H, m), 7.43–7.49 (2H, m), 7.25–7.35 (3H, m), 5.27 (1H, br s), 4.21 (1H, t, J 7.3 Hz), 3.94–3.96 (1H, m), 3.77 (1H, t, J 7.9 Hz), 3.60–3.64 (1H, m), 2.78–2.82 (1H, m), 2.55 (1H, dd, J 7.9 and 12.7 Hz), 2.20–2.24 (1H, m), 1.86–1.95 (2H, m), 1.90 (1H, dd, J 9.3 and 12.6 Hz), 1.68–1.72 (3H, m), 1.48–1.52 (2H, m), 1.45 (9H, s).

Description 33

(2-Ethyloxyvinyl) trifluoromethyl ketone

To a solution of ethyl vinyl ether (22 g, 300 mmol) and pyridine (8 g, 100 mmol) in dichloromethane (150 ml) was slowly added trifluoroacetic anhydride (90 g, 430 mmol), and the mixture stirred for 18 h. The solution was washed with copper sulphate solution (150 ml) and water (150 ml), then dried (MgSO$_4$) and concentrated to give the product as an oil (35 g, 0.21 mmol 69% yield).

H$^1$ NMR δ(250 MHz, CDCl$_3$ ): 7.90 (1H, d, J 12.4 Hz), 5.85 (1H, d, J 12.4 Hz), 4.11 (2H, q, J 7.1 Hz), 1.38 (3H, t, J 7.1 Hz)

Description 34

Nitroacetamide

To ethyl nitroacetate (79.8 g, 0.6 mol) was added ammonia solution (50%, 500 ml) and the solution stirred for 4 days. The solution formed was cooled in ice and acidified to pH1 with concentrated hydrochloric acid, before being evaporated to half volume in vacuo. The suspension formed was extracted with ethyl acetate (2×500 ml), and the extracts dried (MgSO$_4$) and concentrated to give the product as an orange solid (56 g, 0.54 mol, 90% yield).

H$^1$ NMR δ(250 MHz, d$_6$-DMSO): 7.86 (1H, br s), 7.64 (1H, br s), 5.28 (2H, s)

Description 35

3-Nitro-6-trifluoromethyl-2(1H)-pyridone

To ethanol (1 L) was slowly added sodium metal (4.83 g, 0.21 mol). Once the metal had dissolved, nitroacetamide (21.8 g, 0.21 mol) and (2-ethyloxyvinyl) trifluoromethyl ketone (35 g, 0.21 mol) were added, and the suspension formed was heated at reflux for 16 hrs. The resulting mixture was acidified with aqueous hydrochloric acid (1 M) and concentrated in vacuo. The residue was taken up in ethyl acetate (1 L) and the solid formed removed by filtration. The filtrate was then concentrated and the residue purified by silica chromatography to give the product as an orange solid (25.9 g, 0.12 mol, 59% yield).

H$^1$ NMR δ(250 MHz, d$_6$-DMSO): 8.56 (1H, d, J 8.0 Hz), 7.40 (1H, d, J 8.0 Hz)

Description 36

2-Chloro-3-nitro-6-trifluoromethylpyridine

To phosphorous oxychloride (11 ml, 117 mmol) was added quinoline (8.4 ml, 70 mmol) followed by 3-nitro-6- trifluoromethyl-2(1H)-pyridone (24.0 g, 115 mmol), and the resulting solution heated at 140° C. for 18 h. The solution was then cooled to 100° C., when water (50 ml) was carefully added. After cooling to room temperature, saturated sodium bicarbonate (200 ml) was added and the mixture extracted with ethyl acetate (2×200 ml). The extracts were dried (MgSO$_4$) and concentrated, and the residue purified by silica chromatography to give the product as a brown oil (22.7 g, 0.1 mol, 87% yield).

H$^1$ NMR δ(250 MHz, CDCl$_3$): 8.37 (1H, d, J 8.2 Hz), 7.84 (1H, d, J 8.2 Hz)

Description 37

3-Amino-2-chloro-6-trifluoromethylpyridine

2-Chloro-3-nitro-6-trifluoromethylpyridine (22.7 g, 0.10 mol) and platinum(IV) oxide (500 mg) in ethyl acetate (500 ml) were hydrogenated at 20 psi hydrogen for 2 hrs, then the catalyst was removed by filtration. The filtrate was concentrated to give the product as a tan solid (19.5 g, 0.1 mol, 99% yield).

H$^1$ NMR δ(250 MHz, d$_6$-DMSO): 9.33 (1H, s), 9.18 (1H, s), 7.76 (1H, d, J 8.3 Hz), 7.52 (1H, d, J 8.3 Hz)

Description 38

3-Amino-6-trifluoromethylpyridine

3-Amino-2-chloro-6-trifluoromethylpyridine (15.0 g, 76 mmol), sodium acetate (12.53 g, 153 mmol) and 10% palladium on carbon (1.5 g) in methanol (300 ml) were hydrogenated at 50 psi hydrogen for 18 h, then the suspension was filtered. The filtrate was concentrated to give the product as a tan solid (11.38 g, 70 mmol, 92% yield).

H$^1$ NMR δ(250 MHz, CDCl$_3$): 8.12 (1H, d. J 2.7 Hz), 7.44 (1H, d, J 8.5 Hz), 7.01 (1H, dd, J 2.7 and 8.5 Hz), 4.07 (2H, br s)

Description 39

3-Hydroxy-6-trifluoromethylpyridine

3-Amino-6-trifluoromethylpyridine (9.86 g, 61 mmol) was dissolved in concentrated sulphuric acid (70 ml) and diluted with water (70 ml), then cooled to −8° C. A solution of sodium nitrite (5.18 g, 75 mmol) in water (50 ml) was slowly added, and the mixture warmed to 0° C. for 15 minutes. The solution was then poured into sulphuric acid (10 M, 250 ml) and heated to 110° C. for 1 h. After cooling, the pH was adjusted to 6 with saturated sodium bicarbonate solution, and the solution extracted with ethyl acetate (2×300 ml). The extracts were dried (MgSO$_4$) and concentrated to give the product as a yellow solid (7.15 g, 44 mmol, 72% yield).

H$^1$ NMR δ (250 MHz, d$_6$-DMSO): 10.88 (1H, s), 8.26 (1H, d, J 2.7 Hz), 7.72 (1H, d, J 8.6 Hz), 7.35 (1H, dd, J 2.7 and 8.6 Hz)

Description 40

3-Methoxy-6-trifluoromethoxypyridine

3-Hydroxy-6-trifluoromethylpyridine (3.0 g, 18.5 mmol) and potassium carbonate (2.58 g, 18.7 mmol) in N,N′-dimethylformamide (100 ml) was treated with iodomethane (1.2 ml 37.1 mmol) and stirred for 18 h. Water (500 ml) was added and the mixture extracted with ether (2×500 ml). The extracts were dried (MgSO$_4$) and concentrated to give the product as a brown oil (3.2 g, 18.1 mmol, 98% yield).

H$^1$ NMR δ(250 MHz, CDCl$_3$): 8.39 (1H, d. J 2.8 Hz), 7.63 (1H, d, J 8.7 Hz), 7.28 (1H, dd, J 2.8 and 8.7 Hz), 3.92 (3H, s)

Description 41

3-Methoxy-6-trifluoromethyl-2-trimethylstannylpyridine and 3-Methoxy-6-trifluoromethyl-4-trimethylstannylpyridine A solution of t-butyllithium (1.7M in pentane; 8.5 ml, 14.45 mmol) was added dropwise to a stirred solution of 3-methoxy-6-trifluoromethylpyridine (1.57 g, 8.87 mmol) in dry tetrahydrofuran (20 ml) at −78° C. over 5 min. After stirring for 10 min at −78° C. a solution of trimethyltin chloride in tetrahydrofuran (18 ml, 1 M in THF, 18 mmol) was added over 5 min. The reaction mixture was allowed to warm up to room temperature over 5 hour and then quenched with water (50 ml) and extraxted with hexane (3×30 ml). The combined organic extracts were dried (Na$_2$SO$_4$) and concentrated. The residue was purified by chromatography on silica gel (100 g, hexane:diethyl ether 0–10%) to afford 3-methoxy-6-trifluoromethyl-2-trimethystannylpyridine (0.7 g, 23%) H$^1$ NMR δ(250 MHz, CDCl$_3$): 7.50 (1H, d, J 8.7 Hz), 7.02 (1H, d, J 8.7 Hz), 3.85 (3H, s), 0.35 (9H, s); and afford 3-methoxy-6-trifluoromethyl-4-trimethylstannylpyridine (1.7 g, 57%) H$^1$ NMR δ(250 MHz, CDCl$_3$): 8.38 (1H, s), 7.65 (1H, s), 3.95 (3H, s) 0.35 (9H, s).

Description 42

4-Bromo-3-methoxy-6-trifluoromethylpyridine

Bromine (0.52 ml, 10 mmol) was added via syringe to a stirred solution of 3-methoxy-6-trifluoromethyl-4-trimethylstannylpyridine (1.7 g, 5 mmol) in dichloromethane (25 ml). The reaction mixture was stirred for 30 min at room temperature and treated with saturated aqueous Na$_2$SO$_3$ (15 ml). The phases were separated. The aqueous layer was extracted with dichloromethane (2×15 ml). The combined organic extracts were dried (Na$_2$SO$_4$) and concentrated. The residue was purified by chromatography on silica gel (hexane:ethyl acetate 0–15%) to afford 4-bromo-3-methoxy-6-trifluoromethylpyridine as a white solid.

H$^1$ NMR δ(250 MHz, CDCl$_3$): 8.30 (1H, s), 7.88 (1H, s), 4.08 (3H, s).

Description 43

2-Bromo-3-methoxy-6-trifluoromethylpyridine

Prepared from bromine (0.21 ml, 4 mmol) and a solution of 3-methoxy-6-trifluoromethyl-2-trimethylstannylpyridine (0.7 g, 2.0 mmol) in dichloromethane (10 ml) according to the method of Description 42 to afford 4-bromo-3-methoxy-6-trifluoromethylpyridine as a yellow solid.

H$^1$ NMR δ(250 MHz, CDCl$_3$): 7.62 (1H, d, J 8.3 Hz), 7.21 (1H, d, J 8.3 Hz), 3.98 (3H, s).

Description 44

(2S,3R)-3-(Ethoxycarbonylethynyl)-3-hydroxy-2-phenylpiperidine

A solution of dimethyl sulfoxide (4.2 ml, 59 mmol) in dichloromethane (10 ml) was added dropwise to a stirred solution of oxalyl chloride ( 4.4 ml, 51 mmol) in dichloromethane (100 ml) at −70° C. over 10 min. After 10 min a solution of (2S,3S)-3-hydroxy-2-phenylpiperidine (10.5 g, 38.5 mmol) in dichloromethane (30 ml) was added dropwise at −70° C. over 10 min. The mixture was stirred an additional 10 min and triethylamine (15 ml, 108 mmol) added dropwise over 15 min. The reaction mixture was allowed to warm to −10° C. over 90 min and poured into a 10% aqueous solution of citric acid (200 ml). The phases were separated and the aqueous layer was extracted with dichloromethane (2×50 ml). The combined organic extracts were dried ($Na_2SO_4$) and concentrated to give crude (2S)-2-phenyl-3-piperidone which was immediately used in the next step.

A solution of n-butyllithium (55.4 ml, 1.4 M in hexanes, 77.6 mmol) was added dropwise to a stirred solution of ethyl propiolate (7.9 ml, 77.7 mmol) in tetrahydrofuran (200 ml), keeping the temperature of the reaction below −65° C. The mixture was stirred for 10 min and a solution of (2S)-2-phenyl-3-piperidone in tetrahydrofuran (50 ml) added dropwise at −72° C. over 15 min. The reaction mixture was stirred at this temperature for 40 min, quenched with acetic acid (10 ml) and warm up to room temperature. Solvent was removed in vacuo. The residue was treated with saturated aqueous $NaHCO_3$ (200 ml) and extracted with ethyl acetate (3×100 ml). The combined organic extracts were dried ($Na_2SO_4$) and concentrated. The residue was purified by chromatography on silica gel (210 g, hexane:diethyl ether 5–40%) to afford the product (11.9 g, 83%, 96% ee) as a colourless oil.

$H^1$ NMR δ(250 MHz, $CDCl_3$): 7.50 (2H, dd, J 1.8 Hz and 8.2 Hz), 7.20–7.40 (3H, m), 5.51 (1H, s), 4.23 (2H, q, J 7.1 Hz), 4.11 (1H, dd, J 5.4 Hz and 13.5 Hz), 2.97 (1H, dt, J 4.7 Hz and 11.9 Hz), 2.22 (1H, m), 1.90–2.10 (2H, m), 1.65–1.82 (1H, m), 1.40 (9H, s), 1.31 (3H, t, J 7.1 Hz).

Description 45

(5R,6S)-6-Phenyl-1-oxa-2-oxo-7-(tert-butyloxycarbonyl)-7-aza-3-tributylstannylspiro[4.5]dec-3-ene A solution of (2S,3R)-3-(ethoxycarbonylethynyl)-3-hydroxy-2-phenylpiperidine (11.7 g, 31.3 mmol) in toluene (180 ml) was degassed with a stream of nitrogen for 30 minutes. Tetrakis(triphenylphosphine)palladium (1.09 g, 0.88 mmol) was added and the reaction mixture was cooled to 5° C. Then tri-n-butyltin hydride (9 ml, 34 mmol) was added dropwise. The resulting mixture was stirred at room temperature overnight and concentrated in vacuo. The residue was purified by chromatography on silica gel (180 g, hexane:diethyl ether 5–15%) to afford the product (14.8 g, 76%) as a colourless oil.

$H^1$ NMR δ(250 MHz, $CDCl_3$): 7.63 (1H, s), 7.37 (2H, dd, J 1.8 Hz and 8.2 Hz), 7.08–7.32 (3H, m), 5.12 (1H, s), 4.18 (1H, dd, J 5.6 Hz and 13.5 Hz), 3.13 (1H, m), 2.21 (1H, m), 1.70–2.05 (2H, m), 1.65–1.82 (1H, m), 1.40–1.60 (6H, m) 1.38 (9H, s), 1.20–1.40 (6H, m), 1.04 (2H, m), 0.88 (3H, t, J 7.1 Hz).

EXAMPLE 1a (5R,6S)-3-(3-Methoxy-6-N-methyltrifluoromethanesulfonamidopyridin-2-yl)-6-phenyl-1-oxa-7-(tert-butyloxycarbonyl)-7-azaspiro[4.5]dec-3-ene (5R,6S)-3-Tributylstannyl-6-phenyl-1-oxa-7-(tert-butyloxycarbonyl)-7-azaspiro[4.5]dec-3-ene (Desc. 3; 1.45 g, 2.4 mmol), 2-bromo-3-methoxy-6-N-methyl trifluorosulfonamidopyridine (Desc. 9; 838 mg, 2.4 mmol) and lithium chloride (611 mg, 14.4 mmol) in toluene (30 ml) were treated with tetrakis(triphenylphosphine)palladium (0) (100 mg) and the mixture refluxed for 24 hours. After cooling the mixture was filtered and the filtrate concentrated in vacuo. The residue was taken up in acetonitrile (100 ml) and washed with hexane (4×50 ml), before being treated with 5% methanolic potassium fluoride solution (5 ml). The resulting suspension was stirred for 15 minutes then filtered. The filtrate was concentrated and the residue partitioned between ethyl acetate (5 ml) and saturated sodium bicarbonate solution (50 ml). The organic phase was dried ($MgSO_4$) and concentrated, and the residue purified by flash silica chromatography to give the product as a gum (939 mg, 1.6 mmol, 67% yield).

$^1$H NMR (250 MHz, $CDCl_3$) δ7.49–7.51 (2H, m), 7.20–7.33 (5H, m), 7.01 (1H, t, J=2.10 Hz), 5.25 (1H, s), 5.08 (1H, dd, J=2.09 Hz and 12.95 Hz), 4.81 (1H, dd, J=2.09 Hz and 12.95 Hz), 4.09–4.11 (1H, m), 3.95 (3H, s), 3.44 (3H, quartet, J=1.19 Hz), 3.04–3.06 (1H, m), 2.13–2.15 (1H, m), 1.80–1.90 (3H, m), 1.39 (9H, s); M/z ($ES^+$) 584 (M+H).

EXAMPLE 1b (5R,6S)-3-(3-Methoxy-6-N-methyltrifluoromethanesulfonamidopyridin-2-yl)-6-phenyl-1-oxa-7H-azaspiro[4.5]dec-3-ene (5R,6S)-3-(3-Methoxy-6-N-methyltrifluorosulfonamidopyridin-2-yl)-6-phenyl-1-oxa-7-(tert-butoxycarbonyl)-7-azaspiro[4.5]dec-3-ene (Ex. 1a; 939 mg, 1.6 mmol) in dichloromethane (10 ml) was treated dropwise with trifluoroacetic acid (1 ml) and stirred for hour at 22° C. The solution was concentrated in vacuo and the residue poured into saturated sodium bicarbonate solution (20 ml). This was extracted with dichloromethane (2×20 ml) and the extracts dried ($MgSO_4$) and concentrated. The residue was purified by flash silica chromatography and the product taken up in ether (20 ml), then treated with oxalic acid in ether. The salt formed was recovered by filtration and recrystallised from methanol/tert-butylmethyl ether to give product as the hydrogen oxalate salt (89 mg, 0.15 mmol).

M.p. 226–228° C. (methanol/tert-butylmethyl ether);

Analysis Found: C, 50.36; H, 4.57; N, 7.33.

$C_{22}H_{24}F_3N_3O_4S.C_2H_2O_4$ requires: C, 50.36; H, 4.39; N, 7.25%.

$^1$H NMR (360 MHz, DMSO-$d_6$) δ7.59 (1H, d, J=6.15 Hz), 7.43–7.45 (2H, m), 7.37 (1H, d J=6.15 Hz), 7.26–7.32 (3H, m), 6.66 (1H, s), 4.90 (1H, d, J=12.54 Hz), 4.59 (1H, s), 4.45(1H, d, J=12.54 Hz), 3.91 (3H, s), 3.34 (3H, s) 3.05–3.09 (2H, m), 2.03–2.07 (2H, m), 1.85–1.87 (2H, m); M/z ($ES^+$) 484 (M+H).

EXAMPLE 2

(3S,5R,6S)-3-(3-Methoxy-6-N-methyltrifluoromethanesulfonamidopyridin-2-yl)-6-phenyl-1-oxa-7H-azaspiro[4.5]decane (5R,6S)-3-(3-Methoxy-6-N-methyltrifluorosulfonamidopyridin-2-yl)-6-phenyl-1-oxa-7H-azaspiro[4.5]dec-3-ene (Ex. 1b; 400 mg, 0.83 mmol) in methanol (40 ml) was treated with acetic acid (4 ml) and palladium hydroxide on carbon (100 mg). This suspension was hydrogenated at 50 psi hydrogen for 16 hours, then filtered. The filtrate was concentrated in vacuo and the residue basified with saturated sodium bicarbonate solution (50 ml), then extracted with ethyl acetate (2×50 ml). The extracts were dried ($MgSO_4$) and concentrated, and the residue purified by flash silica chromatography. The product was dissolved in ethyl acetate (20 ml) and treated with ethereal hydrogen chloride solution (10 ml, 1M). The solid formed was recovered by filtration and recrystallised twice from methanol/tert-butyl methyl ether, to give the hydrochloride salt of the product as a white solid (50 mg, 0.1 mmol, 11% yield).

M.p. 275–276° C. (methanol/tert-butylmethyl ether);

Analysis Found: C, 50.53; H, 5.40; N, 8.03.

$C_{22}H_{26}F_3N_3O_4S.HCl$ requires: C, 50.45; H, 4.99; N, 8.05;

$^1$H NMR (360 MHz, DMSO-$d_6$) δ9.54 (1H, br s), 8.90 (1H, br s), 7.50–7.52 (2H, m), 7.45 (1H, d J=8.82 Hz), 7.40–7.42 (3H, m), 7.22 (1H, d J=8.82 Hz), 4.48 (1H, s), 4.12 (1H, t, J=7.52 Hz), 3.94–3.95 (1H, m), 3.80 (3H, s), 3.24 (1H, m), 3.10 (3H, s), 3.07–3.09 (1H, m), 2.07–2.04 (5H, m); M/z (ES$^+$) 486 (M+H).

EXAMPLE 3a (5R,6S)-3-(3-Methoxy-6-(5-trifluoromethyl-1,2,3,4-tetrazol-1-yl)-pyridin-2-yl)-6-phenyl-1-oxa-7-(tert-butyloxycarbonyl)-7-azaspiro[4.5]dec-3-ene (5R,6S)-3-Tributylstannyl-6-phenyl-1-oxa-7-(tert-butyloxycarbonyl)-7-azaspiro[4.5]dec-3-ene (Desc. 3; 707 mg, 1.17 mmol), 2-bromo-3-methoxy-5-(5-trifluoromethyl-1,2,3,4-tetrazol-1-yl)pyridine (Desc. 10; 380 mg, 1.17 mmol) and lithium chloride (297 mg, 7 mmol) in toluene (15 ml) were treated with tetrakis(triphenylphosphine)palladium (0) (50 mg) and the mixture refluxed for 24 hours. After cooling the mixture was filtered and the filtrate concentrated in vacuo. The residue was taken up in acetonitrile (100 ml) and washed with hexane (4×50 ml), before being treated with 5% methanolic potassium fluoride solution (5 ml). The resulting suspension was stirred for 15 minutes then filtered. The filtrate was concentrated and the residue partitioned between ethyl acetate (50 ml) and saturated sodium bicarbonate solution (50 ml). The organic phase was dried (MgSO$_4$) and concentrated, and the residue purified by flash silica chromatography to give the product as a gum (287 mg, 0.51 mmol, 44% yield).

$^1$H NMR (250 MHz, CDCl$_3$) δ7.80 (1H, d, J=8.75 Hz), 7.47–7.51 (3H, m), 7.18–7.32 (3H, m), 7.14 (1H, t, J=2.11 Hz), 5.25 (1H, br s), 5.07 (1H, dd, J=2.06 Hz and 13.09 Hz), 4.78 (1H, dd, J=2.06 Hz and 13.09 Hz), 4.05 (3H, s), 3.01–3.13 (1H, m), 2.12–2.19 (1H, m), 1.78–1.92 (3H, m), 1.04 (9H, s), 0.84–0.88 (1H, m).

EXAMPLE 3b (5R,6S)-3-(3-Methoxy-6-(5-trifluoromethyl-1,2,3,4-tetrazol-1-yl)-pyridin-2-yl)-6-phenyl-1-oxa-7H-azaspiro[4.5]dec-3-ene (5R,6S)-3-(3-Methoxy-6-(5-trifluoromethyl-1,2,3,4-tetrazol-1-yl)-pyridin-2-yl)-6-phenyl-1-oxa-7-(tert-butyloxycarbonyl)-7-azaspiro[4.5]dec-3-ene (Ex. 3a; 287 mg, 0.5 mmol) in dichloromethane (10 ml) was treated dropwise with trifluoroacetic acid (1 ml) and stirred for 1 hour at 22° C. The solution was concentrated in vacuo and the residue poured into saturated sodium bicarbonate solution (50 ml). This was extracted with ethyl acetate (2×50 ml) and the extracts dried (MgSO$_4$) and concentrated. The residue was purified by flash silica chromatography to give the product as a gum (220 mg, 0.48 mmol, 94% yield).

$^1$H NMR (250 MHz, CDCl$_3$) δ7.69 (1H, d, J=8.79 Hz), 7.34–7.38 (3H, m), 7.14–7.20 (3H, m), 6.63 (1H, t, J=2.10 Hz), 4.95 (1H, dd, J=2.05 Hz and 12.96 Hz), 4.52 (1H, dd, J=2.05 Hz and 12.96 Hz), 3.97 (3H, s) 3.23–3.27 (1H, m), 2.86–2.90 (1H, m), 1.78–2.18 (5H, m).

EXAMPLE 4

(3S,5R,6S)-3-(3-Methoxy-6-(5-trifluoromethyl-1,2,3,4-tetrazol-1-yl)-pyridin-2yl)-6-phenyl-1-oxa-7H-azaspiro[4.5]decane (5R,6S)-3-(3-Methoxy-6-(5-trifluoromethyl-1,2,3,4-tetrazol-1-yl)-pyridin-2-yl)-6-phenyl-1-oxa-7H-azaspiro[4.5]dec-3-ene (Ex. 3b; 120 mg, 0.26 mmol) and palladium hydroxide on carbon (100 mg) were taken up in methanol (20 ml) and acetic acid (2 ml), and hydrogenated at 50 psi hydrogen for 16 hours. The catalyst was removed by filtration and the filtrate concentrated in vacuo. The residue was basified with saturated sodium bicarbonate solution (50 ml) and extracted with ethyl acetate (2×50 ml), and the extracts dried (Na$_2$SO$_4$) and concentrated. The crude product was purified by silica chromatography, and the pure free base taken up in ethyl acetate (20 ml). This solution was treated with oxalic acid in ether and concentrated, then taken up in water (20 ml) and freeze dried, to give the oxalate salt as a white solid (33 mg, 0.055 mmol, 21% yield).

Analysis Found: C, 49.82; H, 4.55; N, 13.73.

$C_{22}H_{23}F_3N_6O_2.C_2H_2O_4$ requires: C, 49.67; H, 4.50; N, 13.90%.

$^1$H NMR (360 MHz, DMSO-$d_6$) δ7.77 (1H, d, J=6.04 Hz), 7.70 (1H, d, J=6.04 Hz), 7.41–7.44 (2H, m), 7.23–7.29 (3H, m), 4.47 (1H, br s), 4.20 (1H, t, J=7.62 Hz), 3.96–4.0 (1H, m), 3.90 (3H, s), 3.24–3.28 (2H, m), 3.02–3.06 (1H, m), 1.77–2.07 (6H, m); (ES$^+$) 461 (M+H).

EXAMPLE 5a (5R,6S)-3-(3-Methoxy-6-(2-trifluoromethylimidazol-1-yl)pyridin-2-yl)-6-phenyl-1-oxa-7-(tert-butyloxycarbonyl)-7-azaspiro[4.5]dec-3-ene 2-Bromo-3-methoxy-5-(2-trifluoromethylimidazol-1-yl) pyridine (480 mg, 1.49 mmol) was coupled to (5R,6S)-3-tributylstannyl-6-phenyl-1-oxa-7-(tert-butyloxycarbonyl)-7-azaspiro[4.5]dec-3-ene (Desc. 3; 900 mg, 1.49 mmol), as described in Example 1a to give the product as a gum (576 mg, 1.04 mmol 70% yield).

$^1$H NMR (250 MHz, CDCl$_3$) δ7.48–7.51 (2H, m), 7.40 (1H, d, J=8.73 Hz), 7.20–7.33 (6H, m), 7.09 (1H, t, J=2.09 Hz), 5.25 (1H, s), 5.08 (1H, dd, J=2.09 Hz and 13.10 Hz), 4.81 (1H, dd, J=2.09 Hz and 13.10 Hz), 4.10–4.16 (1H, m), 4.01 (3H, s), 3.00–3.12 (1H, m), 2.04–2.22 (1H, m), 1.70–1.94 (3H, m), 1.40 (9H, s).

EXAMPLE 5b (5R,6S)-3-(3-Methoxy-6-(2-trifluoromethylimidazol-1-yl)pyridin-2-yl)-6-phenyl-1-oxa-7H-azaspiro[4.5]dec-3-ene (6R,6S)-3-(3-Methoxy-6-(2-tirfluoromethylimidazol-1-yl)pyridin-2-yl)-6-phenyl-1-oxa-7-(tert-butyloxycarbonyl)-7-azaspiro[4.5]dec-3-ene (Ex. 5a; 570 mg, 1.03 mmol) in dichloromethane (10 ml) was treated dropwise with trifluoroacetic acid (1 ml) and stirred for 1 hour at 22° C. The solution was concentrated in vacuo and the residue poured into saturated sodium bicarbonate solution (50 ml). This was extracted with ethyl acetate (2×50 ml) and the extracts dried (MgSO$_4$) and concentrated. The residue was purified by flash silica chromatography and the product taken up in ethyl acetate (20 ml), then treated with ethereal hydrogen chloride solution (1 ml, 1M). The salt formed was recovered by filtration and recrystallised from methanol/tert-butylmethyl ether to give the dihydrochloride salt of the product (30 mg, 0.06 mmol, 6% yield).

M.p. 190–191° C. (methanol/tert-butylmethyl ether);

Analysis Found: C, 53.89; H, 4.67; N, 10.34.

C$_{24}$H$_{23}$F$_3$N$_4$O$_2$.2HCl requires: C, 53.54; H, 4.87; N, 10.41%.

$^1$H NMR (360 MHz, DMSO-d$_6$) δ9.67 (1H, br d), 9.08 (1H, br d), 7.79 (1H, d, J=1.22 Hz), 7.71 (1H, d, J=8.84 Hz), 7.54 (1H, d, J=84 Hz), 7.44–7.46 (2H, m), 7.27–7.33 (3H, m), 7.23 (1H, d, J=1.22 Hz), 6.71 (1H, br s), 4.87 (1H, d, J=14.70Hz), 4.61 (1H, d, J=10.37 Hz), 4.47 (1H, d, J=10.37 Hz), 3.96 (3H, s), 3.16–3.40 (1H, m), 3.04–3.10 (1H, m), 2.04–2.07 (2H,m), 1.85–1.88 (2H, m); M/z (ES$^+$) 457 (M+H).

EXAMPLE 6

(3S,5R,6S)-3-(3-Methoxy-6-(2-trifluoromethylimidazol-1-yl)pyridin-2-yl)-6-phenyl-1-oxa-7H-azaspiro[4.5]decane (5R,6S)-3-(3-Methoxy-6-(2-trifluoromethylimidazol-1-yl)pyridin-2-yl)-6-phenyl-1-oxa-7H-azaspiro[4.5]dec-3-ene (Ex. 5b; 250 mg, 0.55 mmol) and palladium hydroxide on carbon (100 mg) were taken up in methanol (20 ml) and acetic acid (2 ml), and hydrogenated at 50 psi hydrogen for 16 hours. The catalyst was removed by filtration and the filtrate concentrated in vacuo. The residue was basified with saturated sodium bicarbonate solution (50 ml) and extracted with ethyl acetate (2×50 ml), and the extracts dried (Na$_2$SO$_4$) and concentrated. The crude product was purified by silica chromatography, and the pure free base taken up in ethyl acetate (20 ml). This solution was treated with ethereal hydrogen chloride solution (2 ml, 1M) and the solid formed removed by filtration and washed with ethyl acetate. Finally the hydrochloride salt was recrystallised in isopropyl alcohol/tert-butyl methyl ether to give the hydrochloride salt as a white crystalline solid (43 mg, 0.087 mmol, 16% yield).

M.p. 251–252° C. (isopropyl alcohol/tert-butyl methyl ether);

Analysis Found: C, 58.18; H, 5.29; N, 11.25.

C$_{24}$H$_{25}$F$_3$N$_4$O$_2$.HCl requires: C, 58.24; H, 5.29; N, 11.32%.

$^1$H NMR (360 MHz, DMSO-d$_6$) δ9.57 (1H, br d), 8.91 (1H, br d), 7.54–7.57 (2H, m), 7.45–7.47 (2H, m), 7.41 (1H, d, J=8.62 Hz), 7.23–7.29 (4H, m), 4.46 (1H, br d, J=11.09 Hz),4.15 (1H, t, J=7.71 Hz), 3.88–3.93 (1H, m), 3.83 (3H, s), 3.45 (1H, dd, J=7.95 Hz and 9.90 Hz), 3.21–3.24 (1H, m), 3.03–3.07 (1H, m), 1.89–2.04 (4H, m), 1.75–1.82 (2H, m); M/z (ES$^+$) 459 M+H).

EXAMPLE 7

(3S,5R,6S)-3-(3-Methoxy-6-aminopyridin-2-yl)-6-phenyl-1-oxa-7-(tert-butyloxycarbonyl)-7-azaspiro[4.5]decane (5R,6S)-3-(3-Methoxy-6-nitropyridin-2-yl)-6-phenyl-1-oxa-7-(tert-butyloxycarbonyl)-7-azaspiro[4.5]dec-3-ene (840 mg, 1.8 mmol; prepared from the compounds of Description 3 and Description 5 according to the method of Example 1a) in methanol (40 ml) was treated with acetic acid (4 ml) and palladium hydroxide on carbon (100 mg), and the suspension hydrogenated at 50 psi hydrogen for 72 hours. The catalyst was removed by filtration and the filtrate concentrated in vacuo. The residue was taken up in saturated sodium bicarbonate solution (50 ml) and extratced with ethyl acetate (2'50 ml). The extracts were dried (MgSO$_4$) and concentrated, and the crude product purified by flash silica chromatography to give a yellow gum (346 mg, 0.79 mmol, 44% yield).

$^1$H NMR (250 MHz, CDCl$_3$) δ7.56–7.59 (2H, m), 7.21–7.33 (3H, m), 7.03 (1H, br d), 7.39 (1H, br d), 5.64 (1H, br s), 4.21 (1H, t, J=7.38 Hz), 3.81–3.99 (3H, m), 3.74 (3H, s), 2.82–2.98 (1H, m), 2.54–2.66 (1H, m), 2.04–2.28 (2H, m), 1.70–1.76 (3H, m), 1.42 (9H, s).

EXAMPLE 8

(3S,5R,6S)-3-(3-Methoxy-6-dimethylaminopyridin-2-yl)-6-phenyl-1-oxa-7H-azaspiro[4.51]decane (5R,6S)-3-(3-Methoxy-6-aminopyridin-2-yl)-6-phenyl-1-oxa-7-(tert-butyloxycarbonyl)-7-azaspiro[4.5]decane (Ex. 7; 280 mg, 0.64 mmol) in 1,2-dichloroethane (50 ml) was treated with paraformaldehyde (192 mg, 6.4 mmol) and acetic acid (6 ml). The resulting solution was stirred at 22° C. for 1 hour, when sodium triacetoxyborohydride (679 mg, 3.2 mmol) was added, and the suspension formed was stirred for a further 16 hours. More acetic acid (6 ml) and sodium triacetoxyborohydride (679 mg, 3.2 mmol) were added and the suspension stirred for 2 hours, after which it was poured into ice/sodium hydroxide mixture (200 ml, 2M) and extracted with dichloromethane (2×200 ml). The extracts were dried (MgSO$_4$) and concentrated to give the crude dimethylated amine. This was taken up in dichloromethane (10 ml) and treated dropwise with trifluoroacetic acid (1 ml). The solution formed was stirred for 30 minutes at 22° C. and then concentrated in vacuo. The residue was basified with saturated sodium bicarbonate solution (50 ml) and extracted with ethyl acetate (2×50 ml). The extracts were dried (Na$_2$SO$_4$) and concentrated, and the residue purified by flash silica chromatography. The amine was then dissolved in methanol (20 ml) and treated with ethereal hydrogen chloride solution (2 ml, 1M), and the solvent removed to give the salt. This was recrystallised in isopropanol/ethyl acetate to give the dihydrochloride salt as white crystals (130 mg, 0.30 mmol, 47% yield).

M.p. 265–267° C. (isopropanol/ethyl acetate);

$^1$H NMR (360 MHz, DMSO-d$_6$) δ9.65 (1H, br d), 8.91 (1H, br d), 7.53–7.57 (2H, m), 7.39–7.45 (4H, m), 7.27 (1H, d, J=8.89 Hz), 4.45–4.49 (1H, m), 3.86–4.05 (2H, m), 3.63 (3H, s), 3.33–3.39 (1H, m), 3.24–3.27 (1H, m), 3.00–3.07 (1H, m), 2.68 (6H, s), 2.01–2.14 (3H, m), 1.77–1.86 (3H, m); M/z (ES$^+$) 368 (M+H).

EXAMPLE 9a

(5R,6S)-3-(2-Methoxy-5-trifluoromethylpyridin-3-yl)-6-phenyl-1-oxa-7-(tert-butyloxycarbonyl)-7-azaspiro[4.5]dec-3-ene 3-Iodo-2-methoxy-5-trifluoromethylpyridin (266 mg) was coupled to (5R,6S)-3-tributylstannyl-6-phenyl-1-oxa-7-(tert-butyloxycarbonyl)-7-azaspiro[4.5]dec-3-ene (500 mg) as described in Example 1a to give the product as an oil (479 mg).

$^1$H NMR δ(250 MHz, CDCl$_3$): 8.33 (1H, d, J 2.3 Hz), 7.66–7.72 (2H, m), 7.38 (1H, d, J 2.3 Hz), 7.17–7.29 (3H, m), 6.79 (1H, t, J 2.0 Hz), 5.16 (1H, s), 4.95 (1H, dd, J 2.0

Hz and 12.0 Hz), 4.60 (1H, dd, J 2.0 Hz and 12.0 Hz), 4.12–4.15 (1H, m), 4.06 (3H, s), 3.05–3.15 (1H, m), 2.08–2.13 (1H, m), 1.77–1.87 (3H, m) 1.36 (9H, s).

EXAMPLE 9b (5R,6S)-3-(2-Methoxy-5-trifluoromethylpyridin-3-yl)-6-phenyl-1-oxa-7H-azaspiro[4.5]dec-3-ene (5R,6S)-3-(2-Methoxy-5-trifluoromethylpyridin-3-yl)-6-phenyl-1-oxa-7-(tert-butoxycarbonyl)-7-azaspiro[4.5]dec-3-ene (670 mg, 1.37 mmol) in dichloromethane (15 ml) was treated with trifluoroacetic acid (2 ml) and stirred for 2 hrs, before being washed with potassium carbonate solution (6 ml). The organic phase was dried ($Na_2SO_4$) and concentrated, and the residue purified by silica chromatography to give a white solid. This was taken up in methanol (4 ml), and oxalic acid (23 mg) in methanol (3 ml) added. After concentration the residue was triturated with tert-butyl methyl ether to give the product salt as a white powder (81 mg).

M.p. 83–86° C. $H^1$H NMR δ(250 MHz, $d_4$-MeOH): 8.32 (1H, d, J 2.3 Hz), 7.43–7.49 (3H, m), 7.33–7.36 (3H, m), 6.47 (1H, t, J 2.0 Hz), 4.98 (1H, dd, J 2.0 Hz and 12.4 Hz), 4.57 (1H, dd, J 2.0 Hz and 12.4 Hz), 4.52 (1H, s), 3.99 (3H, s), 3.44–3.49 (1H, m), 3.20–3.24 (1H, m), 1.96–2.27 (4H, m); m/z ($ES^+$) 391 (M+H).

EXAMPLE 9c (3S,5R,6S)-3-(2-Methoxy-5-trifluoromethylpyridin-3-yl)-6-phenyl-1-oxa-7H-azaspiro[4.5]decane (5R,6S)-3-(2-Methoxy-5-trifluoromethylpyridin-3-yl)-6-phenyl-1-oxa-7H-azaspiro[4.5]dec-3-ene (43 mg, 0.29 mmol) and palladium hydroxide (110 mg) in methanol (10 ml) and acetic acid (1 ml) was hydrogenated for 48 hrs at 42 psi. After removal of the catalyst by filtration, the filtrate was concentrated and the residue purified by silica chromatography. The product gum was taken up in propan-2-ol (2 ml) and treated with ethanolic hydrogen chloride solution (1 ml, 5M), then concentrated and triturated with tert-butyl methyl ether to give the monohydrochloride salt as a white powder (24 mg).

m.p. 264–266° C.; Found: C, 58.56; H, 5.65; N, 6.37; $C_{21}H_{23}F_3N_2O_2$.HCl requires C, 58.81; H, 5.64; N, 6.53%. $H^1$NMR δ(360 MHz, $D_2O$): 7.85 (1H, d, J 2.4 Hz), 7.12–7.17 (5H, m), 6.86 (1H, d, J 2.4 Hz), 4.10 (1H, s), 3.84 (1H, t, J 11.0 Hz), 3.48 (3H, s), 3.18–3.40 (3H, m), 2.88–2.95 (1H, m), 1.84–1.89 (3H, m), 1.55–1.70 (3H, m); m/z ($ES^+$) 393 (M+H).

EXAMPLE 10a (5R,6S)-3-[2-Dimethylamino-5-trifluoromethylpyridin-3-yl]-6-phenyl-1-oxa-7-(tert-butyloxycarbonyl-7-azaspiro[4.5]dec-3-ene 3-Bromo-2-dimethylamino-5-trifluoromethylpyridin (420 mg) was coupled to (5R,6S)-3-tributylstannyl-6-phenyl-1-oxa-7-(tert-butyloxycarbonyl)-7-azaspiro [4.5]dec-3-ene (856 mg) as described in Example 1a to give the product (733 mg).

$^1$H NMR δ(360 MHz, $CDCl_3$): 8.28 (1H, d, J 2.1 Hz), 7.38–7.40 (2H, m), 7.35 (1H, d, J 2.1 Hz), 7.13–7.24 (3H, m), 6.11 (1H, t, J 2.1 Hz), 5.05 (1H, s), 4.70 (1H, dd, 2.1 Hz), 5.05 (1H, s), 4.70 (1H, dd, J 2.0 Hz and 12.7 Hz), 4.41 (1H, dd, J 2.0 Hz and 12.7 Hz), 4.05–4.09 (1H, m), 3.07–3.12 (1H, m), 2.79 (6H, s), 1.73–1.81 (3H, m), 1.53–1.61 (3H, m), 1.29 (9H, s).

EXAMPLE 10b (5R,6S)-3-[2-Dimethylamino-5-trifluoromethylpyridin-3-yl]-6-phenyl-1-oxa-7H-azaspiro[4.5]dec-3-ene (5R,6S)-3-[2-Dimethylamino-6-trifluoromethylpyridin-3-yl]-6-phenyl-1-oxa-7-(tert-butyloxycarbonyl)-7-azaspiro[4.5]dec-3-ene (720 mg, 1.43 mmol) in dichloromethane (10 ml) was treated with trifluoroacetic acid (2 ml) and stirred at 22° C. for 2 hrs, before being washed with potassium carbonate solution (10 ml) and brine (15 ml). The organic phase was then dried ($MgSO_4$) and concentrated, and the residue purified by silica chromatography to give the product as an oil (324 mg, 56% yield). A portion of the gum (75 mg) was dissolved in methanol (8 ml) and treated with ethereal hydrogen chloride solution (1 ml, 1M), then concentrated. The residue was triturated with ethyl acetate to give the product as a white solid (58 mg, 65% yield).

Found: C, 58.73; H, 5.66; N, 9.30; $C_{22}H_{24}F_3N_3O$.HCl.0.5$H_2O$ requires: C, 58.86; H, 5.84; N, 9.36%. $H^1$NMR δ(250 MHz, $d_4$-MeOH): 8.42 (1H, d, J 2.4 Hz)<7.58–7.73 (5H, m)<7.40 (1H, d, J 2.4 Hz), 6.20 (1H, t, J 2.1 Hz), 4.90 (1H, dd, J 12.8 Hz and 2.1 Hz), 4.75 (1H, s), 4.68 (1H, dd, J 12.8 Hz and 2.1 Hz), 3.63–3.68 (2H, m), 2.40–2.46 (1H, m), 2.19–2.32 (3H, m); m/z ($ES^+$) 404 (M+H).

EXAMPLE 11

(3S,5R,6S)-3-[2-Dimethylamino-5-trifluoromethylpyridin-3-yl]-6phenyl-1-oxa-7H-azaspiro[4.5]decane (5R,6S)-3-yl[2-Dimethylamino-5-trifluoromethylpyridin-3-yl]-6-phenyl-1-oxa-7H-azaspiro[4.5]dec-3-ene (239 mg, 0.59 mmol) and palladium hydroxide (200 mg) in methanol (10 ml) and acetic acid (1 ml) was hydrogenated for 96 h at 50 psi. After removal of the catalyst by filtration, the filtrate was concentrated and the residue purified by silica chromatography. The product gum was taken up in methanol (1 ml) and treated with ethanolic hydrogen chloride solution (1 ml, 5M), then concentrated and triturated with tert-butyl methyl ether to give the monohydrochloride salt as a white powder (19 mg).

Found: C, 54.6; H, 6.44; N, 8.41; $C_{22}H_{26}F_3N_3O$.2HCl0.25$H_2O$ requires: C, 54.7; H, 5.95; N, 8.70%. $H^1$ NMR δ(360 MHz, $d_4$-MeOH): 8.18 (1H, d, J 2.1 Hz), 7.55–7.62 (5H, m), 6.55 (1H, d, J 2.1 Hz), 4.47 (1H, s), 4.27 (1H, t, J 8.1 Hz), 3.86 (1H, quintet, J 9.7 Hz), 3.20–3.47 (3H, m), 2.20–2.34 (3H, m), 1.74–1.94 (3H, m); m/z ($ES^+$) 406 (M+H).

EXAMPLE 12a (5R,6S)-3-[2-(2',2',2'-Trifluoroethoxy)-5-trifluoromethylpyridin-3-yl]-6-phenyl-1-oxa-7-(tert-butyloxycarbonyl)-7-azaspiro[4.5]dec-3-ene 3-Bromo-2-(2',2',2'-trifluoroethoxy)-5-trifluoromethylpyridine (280 mg) was coupled to (5R,6S)-3-tributylstannyl-6-phenyl-1-oxa-7-(tert-butyloxycarbonyl)-7-azaspiro [4.5]dec-3-ene (653 mg) as described in Example 1a to give the desired product (376 mg).

$H^1$ NMR δ(250 MHz, $CDCl_3$); 8.33 (1H, d, J 2.3 Hz), 7.51 (1H, d, J 2.3 Hz), 7.42–7.44 (2H, m), 7.11–7.29 (3H, m), 6.79 (1H, t, J 2.0 Hz), 5.14 (1H, s), 4.59 (1H, dd, J 2.0 Hz and 12.1 Hz), 4.86 (2H, q, J 8.3 Hz), 4.60 (1H, dd, J 2.0 Hz and 12.1 Hz), 4.10–4.16 (1H, m), 3.16–3.22 (1H, m), 2.10–2.12 (1H, m), 1.80–189 (3H, m), 1.35 (9H, s).

EXAMPLE 12b (5R,6S)-3-[2-(2',2',2'Ttrifluoroethoxy)-5-trifluoromethylpyridin-3-yl]-6phenyl-1-oxa-7H-azaspiro[4.5]dec-3-ene (5R,6S)-3-(2-(2',2',2'-Trifluoroethoxy)-5-trifluoromethylpyridin-3-yl)-6-phenyl-1-oxa-7-(tert-butyloxycarbonyl)-7-azaspiro[4.5]dec-3-ene (320 mg, 0.57 mmol) in dichloromethane (10 ml) was treated with trifluoroacetic acid (1.5 ml) and stirred at 22° C. for 1.5 hrs, before being washed with potassium carbonate solution (10 ml) and brine (15 ml). The organic phase was then dried ($MgSO_4$) and concentrated, and the residue purified by silica chromatography to give the product as an oil (197 mg, 75% yield).

$H^1$ NMR δ(250 MHz, $CDCl_3$); 8.22 (1H, d, J 2.3 Hz), 7.32–7.36 (2H, m), 7.24 (1H, d, J 2.3 Hz), 7.12–7.21 (3H, m), 6.39 (1H, t, J 2.0 Hz), 4.65–4.95 (3H, m) 4.34 (1H, dd, J 2.1 Hz and 11.7 Hz), 3.28 (1H, td, J 12.1 Hz and 2.0 Hz), 2.84 (1H, dt, J 2.8 Hz and 12.1 Hz), 1.64–2.04 (4H, m).

EXAMPLE 13

(3S,5R,6S)-3-[2-(2',2',2'-Trifluoroethoxy)-5-trifluoromethylpyridin-3-yl]-6-phenyl-1-oxa-7H-azaspiro[4.5]decane (5R,6S)-3-[2-(2',2',2'Trifluoroethoxy)-5-trifluoromethylpyridin-3-yl]-6-phenyl-1-oxa-7H-azaspiro[4.5]dec-3-ene (188 mg, 0.41 mmol) and palladium hydroxide (107 mg) in methanol (10 ml) and acetic acid (1 ml) was hydrogenated for 15 hrs at 50 psi. After removal of the catalyst by filtration, the filtrate was concentrated and the residue purified by silica chromatography. The product gum was taken up in tert-butyl methyl ether (4 ml) and treated with ethereal hydrogen chloride solution (1 ml, 1M), then concentrated and triturated with tert-butyl methyl ether to give the monohydrochloride salt as a white powder (75 mg).

Found: C, 52.51; H, 4.72; N, 5.36; $C_{22}H_{22}F_6N_2O_2.HCl.0.5H_2O$ requires: C, 52.23; H, 4.78; N, 5.54%. $H^1$ NMR δ(360 MHz, $d_4$-MeOH): 8.21 (1H, d, J 2.2 Hz), 7.49–7.55 (2H, m), 7.44–7.47 (3H, m), 7.09 (1H, d, J 2.2 Hz), 6.36–6.45 (2H, m) 5.94 (1H s), 5.78 (1H, t, J 8.0 Hz), 5.32 (1H, quintet, J 9.3 Hz), 4.90–4.96 (2H, m), 4.71 (1H, dt, 3.2 Hz and 12.8 Hz), 3.68–3.78 (3H, m), 3.33–3.44 (3H, m); m/z ($ES^+$) 461 (M+H).

EXAMPLE 14a (5R,6S)-3-[2-(2',2',2'-Trifluoroethoxy)-5-(2-trifluoromethylimidazol-1-yl)pyridin-3-yl]-6-phenyl-1-oxa-7-(tert-butyloxycarbonyl)-7-azaspiro[4.5]dec-3-ene 3-Bromo-2-(2',2',2'-trifluoroethoxy)-5-(2-trifluoromethylimidazol-1-yl)pyridine was coupled to (5R,6S)-3-tributylstannyl-6-phenyl-1-oxa-7-(tert-butyloxycarbonyl)-7-azaspiro [4.5]dec-3-ene as described in Example 1a to give the product (482 mg).

$H^1$ NMR δ(250 MHz, $CDCl_3$): 8.09 (1H, d, J 2.5 Hz), 7.41–7.44 (2H, m), 7.23–7.34 (5H, m), 7.12 (1H, d, J 1.2 Hz), 6.84 (1H, br t), 5.16 (1H, br s), 4.88 (2H, q, J 12.0 Hz), 4.54–4.59 (1H, m), 4.10–4.16 (1H, m), 3.10–3.14 (1H, m), 2.11–2.17 (1H, m), 1.80–1.90 (3H, m), 1.61–1.64 (2H, m), 1.35 (9H, s).

EXAMPLE 14b (5R,6S)-3-[2-(2',2',2'-Trifluoroethoxy)-5-(2-trifluoromethylimidazol-1-yl)pyridin-3-yl]-6-phenyl-1-oxa-7H-azaspiro[4.5]dec-3-ene (5R,6S)-3-[2-(2',2',2'-Trifluoroethoxy)-5-(2-trifluoromethylimidazol-1-yl)pyridin-3-yl]-6-phenyl-1-oxa-7-(tert-butyloxycarbonyl)-7-azaspiro[4.5]dec-3-ene (470 mg, 0.75 mmol) in dichloromethane (10 ml) was treated with trifluoroacetic acid (1 ml) and stirred at 22° C. for 6 hrs, before being quenched with sodium carbonate solution (20 ml). The organic phase was dried ($Na_2SO_4$) and concentrated to give an oil. This was taken up in methanol (4 ml) and treated with ethereal hydrogen chloride solution (1 ml, 1M), then concentrated. The residue was triturated with tert-butyl methyl ether (5 ml) to give the product as a fine white powder (96 mg).

m.p. 154–158° C.; Found: C, 51.51; H, 4.31; N, 9.49; $C_{25}H_{22}F_6N_4O_2.HCl.H_2O$ requires: C, 51.87; H, 4.35; N, 9.68%. $H^1$ NMR δ(360 MHz, $d_4$-MeOH): 8.17 (1H, d, J 2.3 Hz), 7.56 (1H, d, J 2.3 Hz), 7.44–7.46 (3H, m), 7.32–7.34 (3H, m), 7.24 (1H, d, J 1.2 Hz), 6.48 (1H, br s), 4.88–5.02 (3H, m), 4.56–4.59 (2H, m), 3.45–3.48 (1H, m), 3.25–3.29 (1H, m), 2.07–2.10 (1H, m), 2.02–2.06 (3H, m); m/z ($ES^+$) 525 (M+H).

EXAMPLE 15

(3S,5R,6S)-3-[2-(2',2',2'-Trifluoroethoxy)-5-(2-trifluoromethylimidazol-1-yl)pyridin-3-yl]-6-phenyl-1-oxa-7H-azaspiro[4.5]decane (5R,6S)-3-[2-(2',2',2'-Trifluoroethoxy)-5-(2-trifluoromethylimidazol-1-yl)pyridin-3-yl]-6-phenyl-1-oxa-7H-azaspiro[4.5]dec-3-ene (150 mg, 0.29 mmol) and palladium hydroxide (75 mg) in methanol (10 ml) and acetic acid (1.5 ml) was hydrogenated for 48 hrs at 50 psi. After removal of the catalyst by filtration, the filtrate was concentrated and the residue purified by silica chromatography. The product gum was taken up in tert-butyl methyl ether (5 ml) and treated with ethereal hydrogen chloride solution (1 ml, 1M), then concentrated to give the monohydrochloride salt as a white powder (80 mg).

M.p. 144–146° C.; Found: C, 52.54; H, 4.55; N, 9.80; $C_{25}H_{24}F_6N_4O_2.HCl.0.5H_2O$ requires: C, 52.50; H, 4.58; N, 9.80%. $H^1$ NMR δ(360 MHz, $D_2O$): 7.98 (1H, d, J 2.3 Hz), 7.46–7.48 (2H, m), 7.26–7.32 (4H, m), 7.08 (1H, t, J 7.5 Hz), 6.36 (1H, d, J 2.3 Hz), 4.74–4.83 (2H, m), 4.41 (1H, s), 4.26 (1H, t, J 8.5 Hz), 3.91 (1H, t, J 8.5 Hz), 3.42–3.52 (2H, m), 3.22 (1H, dt, J 2.5 Hz and 10.6 Hz), 2.08–2.32 (3H, m), 1.81–1.95 (3H, m); m/z ($ES^+$) 527 (M+H).

EXAMPLE 16a (5R,6S)-3-(2-Methoxy-5-(2-trifluoromethylimidazol-1-yl)pyridin-3-yl)-6-phenyl-1-oxa-7-(tert-butyloxycarbonyl)-7-azaspiro[4.5]dec-3-ene 3-Bromo-2-methoxy-5-(2-trifluoromethylimidazol-1-yl)pyridine was coupled to (5R,6S)-3-tributylstannyl-6-phenyl-1-oxa-7-(tert-butyloxycarbonyl)-7-azaspiro[4.5]dec-3-ene as described in Example 1a to give the product (313 mg).

$H^1$ NMR δ(250 MHz, $CDCl_3$): 8.09 (1H, d, J 2.4 Hz), 7.43–7.46 (2H, m), 7.20–7.30 (4H, m), 7.19 (1H, d, J 2.4 Hz), 7.11 (1H, d, J 1.2 Hz), 6.84 (1H, br t), 5.17 (1H, br s), 4.88 (1H, dd, J 1.9 Hz and 11.9 Hz), 4.55 (1H, dd, J 1.9 Hz and 11.9 Hz), 4.10–4.16 (1H, m), 4.09 (3H, s), 3.09–3.14 (1H, m), 1.73–1.90 (2H, m), 1.57–1.66 (2H, m), 1.37 (9H, s).

EXAMPLE 16b (5R,6S)-3-(2-Methoxy-5-(2-trifluoromethylimidazol-1-yl)pyridin-3-yl)-6-phenyl-1-oxa-7H-azaspiro[4.5]dec-3-ene (5R,6S)-3-(2-Methoxy-5-(2-trifluoromethylimidazol-1-yl)pyridin-3-yl)-6-phenyl-1-oxa-7-(tert-butyloxycarbonyl)-7-azaspiro[4.5]dec-3-ene (305 mg, 0.55 mmol) in dichloromethane (10 ml) was treated with trifluoroacetic acid (1 ml) and stirred at 22° C. for 2 hrs, before being quenched with sodium hydrogen carbonate solution (20 ml). The organic phase was dried ($Na_2SO_4$) and concentrated to give a gum, which was purified by silica chromatography to give the product (160 mg).

$H^1$ NMR δ(250 MHz, $CDCl_3$): 7.98 (1H, d, J 2.5 Hz), 7.33–7.36 (2H, m), 7.13–7.21 (4H, m), 7.03 (1H, d, J 1.2 Hz), 6.96 (1H, d, J 2.5 Hz), 6.36 (1H, t, J 2.0 Hz), 4.80 (1H, dd, J 1.9 Hz and 11.7 Hz), 4.27 (1H, dd, J 1.9 Hz and 11.7 Hz), 4.02 (3H, s), 3.78 (1H, s), 3.21–3.30 (1H, m), 2.82 (1H, dt, J 2.8 Hz and 12.0 Hz), 1.64–2.03 (4H, m).

EXAMPLE 16c (3S,5R,6S)-3-(2-Methoxy-5-(2-trifluoromethylimidazol-1-yl)pyridin-3-yl)-6-phenyl-1-oxa-7H-azaspiro[4.5]decane (5R,6S)-3-(2-Methoxy-5-(2-trifluoromethylimidazol-1-yl)pyridin-3-yl)-6-phenyl-1-oxa-7H-azaspiro[4.5]dec-3-ene (100 mg, 0.22 mmol) and palladium hydroxide (28 mg) in methanol (10 ml) and acetic acid (10 ml) was hydrogenated for 24 hrs at 45 psi. After removal of the catalyst by filtration, the filtrate was concentrated and partitioned between sodium hydrogen carbonate solution (20 ml) and ethyl acetate (20 ml). The organic phase was dried ($Na_2SO_4$), concentrated and the residue purified by silica chromatography. The product gum was taken up in methanol (4 ml) and treated with oxalic acid (5.9 mg, 0.066 mmol) in methanol (2 ml), then heated at reflux for 10 mins. The methanol was removed in vacuo and the residue triturated with tert-butyl methyl ether to give a white solid (27 mg).

Found: C, 54.0; H, 5.1; N, 9.2; $C_{24}H_{25}F_3N_4O_2 \cdot C_2H_2O_4 \cdot 1.8H_2O$ requires: C, 53.75; H, 5.31; N, 9.64%. $H^1$ NMR δ(360 MHz, $d_4$-MeOH): 7.95 (1H, d, J 2.4 Hz), 7.45–7.47 (2H, m), 7.29–7.32 (4H, m), 7.06–7.10 (1H, m), 6.29 (1H, d, J 2.4 Hz), 4.84–4.88 (1H, m), 4.40 (1H, br s), 4.16–4.24 (1H, m), 3.85–3.88 (1H, m), 3.84 (3H, s), 3.42–3.48 (2H, m), 2.10–2.22 (3H, m), 1.80–2.00 (3H, m); m/z ($ES^+$) 459 (M+H).

EXAMPLE 17a (5R,6S)-3-(2-(2-Propyl)oxy-5-trifluoromethylpyridin-3-yl)-6-phenyl-1-oxa-7-(tert-butyloxcarbonyl)-7-azaspiro[4.5]dec-3-ene 3-Bromo-2-(2-propyl)oxy-5-trifluoromethylpyridine (355 mg) was coupled to (5R,6S)-3-tributylstannyl-6-phenyl-1-oxa-7-(tert-butyloxycarbonyl)-7-azaspiro [4.5]dec-3-ene (630 mg) as described in Example 1a to give the product as a gum (92 mg).

$H^1$ NMR δ(250 MHz, $CDCl_3$): 8.31 (1H, d, J 1.2 Hz), 7.43–7.46 (3H, m), 7.21–7.30 (3H, m), 6.74 (1H, t, J 2.0 Hz), 5.44 (1H, heptet, J 6.2 Hz), 5.14 (1H, s), 4.95 (1H, dd, J 2.0 Hz and 12.0 Hz), 4.58 (1H, dd, J 2.0 Hz and 12.0 Hz), 4.11–4.20, (1H, m), 3.07–3.23 (1H, m), 2.05–2.10 (1H, m), 1.65–1.94 (3H, m), 1.42 (3H, d, J 6.2 Hz), 1.39 (3H, d, J 6.2 Hz), 1.37 (9H, s); m/z ($ES^+$) 519 (M+H).

EXAMPLE 17b (5R,6S)-3-(2-(2-Propyl)oxy-5-trifluoromethylpyridin-3-yl)-6-phenyl-1-oxa-7H-azaspiro[4.5]dec-3-ene A sample (91 mg) of the preceeding compound was deprotected with trifluoroacetic acid as described in Example 16b and the product isolated by chromatography on silica gel, eluting with dichloromethane/methanol/aqueous ammonia (95:5:1), to afford a colourless oil (49 mg).

$H^1$ NMR δ(250 MHz, $CDCl_3$): 8.21 (1H, s), 7.35–7.38 (2H, m), 7.16–7.19 (3H, m), 6.30 (1H, s), 5.37 (1H, heptet, J 6.2 Hz), 4.87 (1H, dd, J 2.1 Hz and 11.9 Hz), 4.33 (1H, dd, J 2.1 Hz and 11.9 Hz), 3.83 (1H, s), 3.26–3.38 (1H, m), 2.78–2.93 (1H, m), 1.62–2.18 (4H, m), 1.35 (6H, d, J 6.2 Hz); m/z ($ES^+$) 419 (M+H).

EXAMPLE 18

(3S, 5R, 6S)-3-(2-(2-Propyl)oxy-5-trifluoromethylpyridin-3-yl)-6-phenyl-1-oxa-7H-azaspiro[4.5]decane A solution of the preceeding compound (43 mg) in methanol (10 ml) and acetic acid (1 ml) was shaken over palladium hydroxide on carbon (33 mg) under an atmosphere of hydrogen at 50 psi for 18 h. More catalyst (30 mg) was then added, and hydrogenation resumed for a further 5 h. The suspension was filtered, the filtrate evaporated, and the residual gum chromatographed on silica, eluting with dichloromethane/methanol/aqueous ammonia (95:5:1), to afford a gum, which was converted to the hydrogen oxalate salt. Recrystallisation from EtOAc/hexane afforded the desired product as a colourless solid (17 mg).

$H^1$ NMR δ(500 MHz, $d_6$-DMSO): 9.36–9.47 (1H, m), 8.84–8.99 (1H, m), 8.33 (1H, s), 7.51–7.52 (2H, m), 7.40–7.45 (3H, m), 6.97 (1H, s), 5.26 (1H, heptet, J 6.2 Hz), 4.51 (1H, s), 4.17 (1H, app. t, J 8.0 Hz), 3.68 (1H, dd, J 8.2 Hz and 9.7 Hz), 3.27–3.30 (2H, m), 3.10 (1H, br s), 2.07–2.18 (2H, m), 1.96–2.05 (1H, m), 1.70–1.85 (3H, m), 1.25 (3H, d, J 6.2 Hz), 1.21 (3H, d, J 6.2 Hz); m/z ($ES^+$) 421 (M+H).

EXAMPLE 19a (5R,6S)-3-(2-Ethoxy-5-trifluoromethylpyridin-3-yl)-6-phenyl-1-oxa-7-(tert-butyloxycarbonyl)-7-azaspiro [4.5]dec-3-ene A mixture of 3-bromo-2-ethoxy-5-trifluoromethylpyridine (338 mg, 1.25 mmol), (5R,6S)-3-tributylstannyl-6-phenyl-1-oxa-7-(tert-butyloxycarbonyl)-7-azaspiro [4.5]dec-3-ene (627 mg, 1.04 mmol), lithium chloride (264 mg, 6.24 mmol) and tetrakis (triphenylphosphine)palladium (60 mg, 0.052 mmol) in degassed toluene (20 ml) was stirred at reflux for 18 h, after which time a second portion (60 mg) of tetrakis (triphenylphosphine)palladium was added and reflux resumed for 8 h. A further portion of catalyst was subsequently added and stirring at reflux continued for 14 h. the mixture was then evaporated, the residue redissolved in dichloromethane (20 ml) and methanolic potassium fluoride added. After standing for 0.5 h, the resulting suspension was filtered, the filtrate evaporated residue chromatographed on silica, eluting with hexane/EtOAc (9:1), to give the desired product as a colourless oil (290 mg).

$H^1$ NMR δ(250 MHz, $CDCl_3$): 8.32 (1H, br s), 7.42–7.48 (3H, m), 7.20–7.32 (3H, m), 6.78 (1H, t, J 2.0 Hz), 5.16 (1H, s), 4.96 (1H, dd, J 2.0 Hz and 12.1 Hz), 4.61 (1H, dd, J 2.0 Hz and 12.1 Hz), 4.53 (2H, q, J 7.1 Hz), 4.11–4.20 (1H, m), 3.04–3.21 (1H, m), 2.03–2.21 (1H, m), 1.73–196 (3H, m), 1.46 (3H, t, J 7.1 Hz), 1.37 (9H, s).

EXAMPLE 19b (5R,6S)-3-(2-Ethoxy-5-trifluoromethylpyridin-3-yl)-6-phenyl-1-oxa-7H-azaspiro[4.5]dec-3-ene A sample (280 mg) of the preceeding compound was deprotected with trifluoroacetic acid as described in Example 16b and the product isolated by chromatography on silica gel, eluting with dichloromethane/methanol/aqueous ammonia (95:5:1), to afford a colourless oil (20 mg).

$H^1$ NMR δ(360 MHz, CDCl$_3$): 8.21 (1H, s), 7.35 (2H, d, J 6.6 Hz), 7.13–7.20 (4H, m), 6.32 (1H, t, J 2.1 Hz), 4.86 (1H, dd, J 2.1 Hz and 11.9 Hz), 4.38–4.48 (2H, m) 4.32 (1H, dd, J 2.1 Hz and 11.9 Hz), 3.79 (1H, s), 3.27–3.30 (1H, m), 2.84 (1H, dt, J 2.8 Hz and 12.4 Hz), 1.62–2.05 (4H, m), 1.42 (3H, t, J 7.1 Hz); m/z (ES$^+$) 405 (M+H).

EXAMPLE 20

(3S, 5R, 6S)-3-(2-Ethoxy-5-trifluoromethylpyridin-3-yl)-6-phenyl-1-oxa-7H-azaspiro[4.5]decane The preceeding compound (150 mg) was hydrogenated over palladium hydroxide as described in Example 16c and the product isolated as the hydrogen oxalate salt. Recrystallisation from EtOAc/hexane gave a colourless solid (79 mg).

$H^1$ NMR δ(360 MHz, d$_6$-DMSO): 8.35 (1H, s), 7.54–7.56 (2H, m), 7.40–7.50 (3H, m), 7.10 (1H, s), 4.50 (1H, s), 4.24–4.28 (2H, m), 4.15 (1H, app. t, J 8.1 Hz), 3.67–3.78 (1H, m), 3.29–3.34 (2H, m), 3.04–3.16 (1H, m), 2.01–2.17 (3H, m), 1.77–1.89 (3H, m), 1.22 (3H, t, J 7.0 Hz); m/z (ES$^+$) 407 (M+H).

EXAMPLE 21a (5R,6S)-3-(2-(2-Methoxy)ethoxy-5-trifluoromethylpyridin-3-yl)-6-phenyl-1-oxa-7-(tert-butyloxycarbonyl)-7-azaspiro[4.5]dec-3-ene Coupling of the above bromide (0.75 g, 2.5 mmol) with (5R,6S)-3-tributylstannyl-6-phenyl-1-oxa-7-(tert-butyloxycarbonyl)-7-azaspiro [4.5]dec-3-ene (1.52 g, 2.5 mmol) under the conditions described in Example 1a afforded the product as a pale yellow oil (87 mg).

$H^1$ NMR δ(250 MHz, CDCl$_3$): 8.32 (1H, br s), 7.42–7.51 (3H, m), 7.20–7.30 (3H, m), 6.89 (1H, t, J 2.0 Hz), 5.15 (1H, s), 4.96 (1H, dd, J 2.0 Hz and 12.1 Hz), 4.63 (1H, dd, J 2.0 Hz and 12.1 Hz), 4.57–4.60 (2H, m), 4.10–4.21 (1H, m), 3.76–3.80 (2H, m), 3.46 (3H, s), 3.07–3.20 (1H, m), 2.03–2.18 (1H, m), 1.74–1.98 (3H, m), 1.36 (9H, s).

EXAMPLE 21b (5R,6S)-3-(2-(2-Methoxy)ethoxy-5-trifluoromethylpyridin-3-yl)-6-phenyl-1-oxa-7H-azaspiro[4.5]dec-3-ene Prepared in an analogous fashion to that described in Example 16b.

$H^1$ NMR δ(250 MHz, CDCl$_3$): 8.21 (1H, br s), 7.36 (2H, dd, J 1.9 Hz and 8.0 Hz), 7.10–7.22 (4H, m), 6.42 (1H, t, J 2.1 Hz), 4.86 (1H, dd, J 2.1 Hz and 11.8 Hz), 4.46–4.61 (2H, m), 4.32 (1H, dd, J 2.1 Hz and 11.8 Hz), 3.78 (1H, s), 3.76 (3H, t, J 4.8 Hz), 3.47 (3H, s), 3.23–3.34 (1H, m), 2.84 (1H, dt, J 2.7 Hz and 11.9 Hz), 1.60–2.07 (4H, m); m/z (ES$^+$) 435 (M+H).

EXAMPLE 22

(3S, 5R, 6S)-3-(2-(2-Methoxy)ethoxy-5-trifluoromethylpyridin-3-yl)-6-phenyl-1-oxa-7H-azaspiro[4.5]decane The compound of Example 21b (148 mg) was hydrogenated over palladium hydroxide as described in Example 16c and the product isolated as the free base in the form of a colourless foam (55 mg).

$H^1$ NMR δ(360 MHz, CDCl$_3$): 8.14 (1H, br s), 7.46 (2H, dd, J 1.8 Hz and 7.9 Hz), 7.24–7.33 (3H, m), 6.77 (1H, d, J 2.3 Hz), 4.44–4.468 (2H, m), 4.13 (1H, t, J 8.0 Hz), 3.73–3.78 (1H, m), 3.68–3.70 (2H, m), 3.65 (1H, s), 3.40 (3H, s), 3.24 (1H, dt, J 2.4 Hz and 11.9 Hz), 3.13 (1H, dd, J 8.4 Hz and 9.7 Hz), 8.21 (1H, dt, J 2.5 Hz and 12.4 Hz), 1.82–2.15 (4H, m), 1.55–1.63 (2H, m); m/z (ES$^+$) 437 (M+H).

EXAMPLE 23

(3R,5R,6S)-3-[2-(2-propyloxy)-5-trifluoromethylpyridin-3-yl]-6-phenyl-1-oxa-7-(tert-butyloxycarbonyl)-7-azaspiro[4.5]decane A solution of (5R,6S)-6-phenyl-1-oxa-7-(tert-butyloxycarbonyl)-7-azaspiro[4.5]dec-3-ene (100 mg, 0.32 mmol), 3-bromo-2-isopropyloxy-5-trifluoromethyl pyridine (273 mg, 0.96 mmol), lithium chloride (136 mg, 3.2 mmol), tetra-n-butylammonium chloride (88 mg, 0.32 mmol) and potassium formate (81 mg, 0.96 mmol) in N,N'-dimethylformamide (2 mL) was degassed with nitrogen at 60° C. for 45 minutes. Palladium acetate (14 mg) was then added and the solution stirred at 65° C. for 48 hrs.

After cooling, water (25 mL) was added, and the solution extracted with ethyl acetate (2×25 mL). The extracts were dried (MgSO$_4$) and concentrated, and the residue purified by silica chromatography to give the product as a gum (45 mg, 0.09 mmol, 27% yield).

$H^1$ NMR δ(250 MHz, CDCl$_3$): 8.30 (1H, d, J 1.2 Hz), 7.62–7.65 (3H, m), 7.24–7.37 (3H, m), 5.41 (1H, sept., J 6.2 Hz), 5.35 (1H, s) 4.33 (1H, t, J 7.6 Hz), 3.95–4.00 (1H, m), 3.83 (1H, t, J 8.4 Hz), 3.64–3.70 (1H, m), 2.77 (1H, dt, J 3.9 and 11.7 Hz), 2.57 (1H, dd, J 7.6 and 18.1 Hz), 2.17–2.30 (1H, m), 1.95 (1H, dd, J 10.1 and 12.5 Hz), 1.70–1.78 (3H, m), 1.46 (9H, s), 1.41 (6H, d, J 6.2 Hz)

EXAMPLE 24

(3R,5R,6S)-3-[2-(2-propyloxy)-5-trifluoromethylpyridin-3-yl]-6-phenyl-1-oxa-7H-azaspiro[4.5]decane hydrochloride (3R,5R,6S)-3-(2-Isopropoxy-5-trifluoromethylpyridin-3-yl)-6-phenyl-1-oxa-7-(tert-butyloxycarbonyl)-7-azaspiro [4.5]decane (100 mg, 0.19 mmol) in dichloromethane (5 mL) was added trifluoroacetic acid (5 mL) and the solution was stirred for 3 hrs. After concentration, saturated sodium bicarbonate solution (20 mL) was added to the residue, and the suspension formed was extracted with dichloromethane (2×20 mL). The extracts were dried (MgSO$_4$) and concentrated, and the residue taken up in ethyl acetate (10 mL). Ethereal hydrogen chloride solution (1M, 1 mL) was added and the solution formed concentrated. The residue was recrystallised from ethyl acetate/tert-butyl methyl ether to give the salt as a grey solid (20.5 mg, 0.05 mmol, 24% yield).

Melting point 270–272° C.; H$^1$ NMR δ(360 MHz, d$_6$-DMSO): 8.23 (1H, br s), 7.59–7.61 (2H, m), 7.52–7.54 (4H, m), 5.29 (1H, septet, J 6.1 Hz), 4.31 (1H, s), 4.13 (1H, t, J 7.7 Hz), 3.77 (1H, dd, J 8.2 and 10.6 Hz), 3.38–3.42 (1H, m), 3.18–3.21 (1H, m), 2.22–2.36 (3H, m), 2.08–2.09 (1H, m), 1.87–1.99 (3H, m), 1.25 (6H, dd, J 1.0 and 6.1 Hz); m/z (ES$^+$) 421 (M+H).

EXAMPLE 25

(3R,5R,6S)-3-(2-Ethoxy-5-trifluoromethylpyridin-3-yl)-6-phenyl-1-oxa-7-(tert-butoxycarbonyl)-7-azaspiro[4.5]decane A solution of (5R,6S)-6-phenyl-1-oxa-7-(tert-butoxycarbonyl)-7-azaspiro[4.5]dec-3-ene (200 mg, 0.64 mmol), 3-bromo-2-ethoxy-5-trifluoromethyl pyridine (520 mg, 1.92 mmol), lithium chloride (272 mg, 6.4 mmol), tetra-n-butylammonium chloride (176 mg, 0.64 mmol) and potassium formate (162 mg, 1.92 mmol) in N,N'-dimethylformamide (4 mL) was degassed with nitrogen at 60° C. for 45 minutes. Palladium acetate (14 mg) was then added and the solution stirred at 65° C. for 48 hrs.

After cooling, water (50 mL) was added, and the solution extracted with ethyl acetate (2×50 mL). The extracts were dried (MgSO$_4$) and concentrated, and the residue purified by silica chromatography to give the product as a gum (143 mg, 0.28 mmol, 44% yield).

H$^1$ NMR δ(250 MHz, CDCl$_3$): 8.30 (1H, d, J 2.3 Hz), 7.67 (1H, d, J 2.3 Hz), 7.59–7.62 (2H, m), 7.25–7.36 (3H, m), 5.35 (1H, s), 4.45 (2H, q, J 5.8 Hz), 4.33 (1H, t, J 7.4 Hz), 3.95–4.00 (1H, m), 3.84 (1H, t, J 8.4 Hz), 3.71–3.78 (1H, m), 2.78 (1H, td, J 11.8 and 4.7 Hz), 2.59 (1H, dd, J 7.5 and 12.8 Hz), 2.20–2.26 (1H, m), 1.94 (1H, dd, J 9.8 and 12.5 Hz), 1.70–1.76 (3H, m), 1.44 (9H, s), 1.41 (3H, t, J 5.8 Hz)

EXAMPLE 26

(3R,5R,6S)-3-(2-Ethoxy-5-trifluoromethylpyrid-3-yl)-6-phenyl-1-oxa-7H-azaspiro[4.5]decane hydrochloride (3R,5R,6S)-3-(2-Ethoxy-5-trifluoromethylpyrid-3-yl)-6-phenyl-1-oxa-7-(tert-butoxycarbonyl)-7-azaspiro[4.5]decane (143 mg, 0.28 mmol) in dichloromethane (5 mL) was added trifluoroacetic acid (1 mL) and the solution was stirred for 1 hr. After concentration, saturated sodium bicarbonate solution (10 mL) was added to the residue, and the suspension formed was extracted with ethyl acetate (2×20 mL). The extracts were dried (MgSO$_4$) and concentrated, and the residue taken up in ethyl acetate (10 mL). Ethereal hydrogen chloride solution (1M, 1 mL) was added and the solution formed concentrated. The residue was recrystallised from ethyl acetate/tert-butyl methyl ether to give the salt as a white solid (42.3 mg, 0.10 mmol, 34% yield).

Melting point 242–244° C.; H$^1$ NMR δ(360 MHz, d$_6$-DMSO), 9.56 (1H, br s), 8.90 (1H, br s), 8.35 (1H, s), 7.77 (1H, s), 7.56–7.58 (2H, m), 7.48–7.50 (3H, m), 4.38 (1H, s), 4.21 (2H, q, J 4.8 Hz), 3.97 (1H, t, J 5.2 Hz), 3.70 (1H, dd, J 7.3 and 5.6 Hz), 3.24–3.26 (1H, m), 3.03–3.05 (1H, m), 2.27 (1H, dd, J 5.3 and 8.6 Hz), 2.04–2.07 (3H, m), 1.82–1.84 (3H, m), 1.23 (3H, t, J 4.8 Hz); m/z (ES$^+$) 407 (M+H).

EXAMPLE 27

(3R,5R,6S)-3-[2-(2',2',2'-Trifluoroethoxy)-5-trifluoromethyl pyridin-3-yl]-6-phenyl-1-oxa-7-(tert-butyloxycarbonyl)-7-azaspiro[4.5]decane A solution of (5R,6S)-6-phenyl-1-oxa-7-(tert-butyloxycarbonyl)-7-azaspiro[4.5]dec-3-ene (554 mg, 1.6 mmol), 3-bromo-2-(2',2',2'-trifluoroethoxy)-5-trifluoromethyl pyridine (776 mg, 2.4 mmol), lithium chloride (680 mg, 16 mmol), tetra-n-butylammonium chloride (440 mg, 1.6 mmol) and potassium formate (407 mg, 4.8 mmol) in N,N'-dimethylformamide (10 mL) was degassed with nitrogen at 60° C. for 45 minutes. Palladium acetate (40 mg) was then added and the solution stirred at 60° C. for 16 hrs.

After cooling, water (100 mL) was added, and the solution extracted with ethyl acetate (2×100 mL). The extracts were dried (MgSO$_4$) and concentrated, and the residue purified by silica chromatography to give the product as a gum (95 mg, 0.17 mmol, 11% yield).

H$^1$ NMR δ(250 MHz, CDCl$_3$): 8.32 (1H, d, J 2.1 Hz), 7.79 (1H, d, J 2.1 Hz), 7.57–7.60 (2H, m), 7.26–7.36 (3H, m), 5.32 (1H, s), 4.80–4.87 (2H, m), 4.31 (1H, t, J 7.6 Hz), 3.96–4.04 (1H, m), 3.90 (1H, t, J 8.2 Hz), 3.70–3.76 (1H, m), 2.74–2.82 (1H, m), 2.58–2.66 (1H, m), 2.20–2.26 (1H, m), 1.93–2.02 (1H, m), 1.70–1.74 (3H, m), 1.45 (9H, s).

EXAMPLE 28

(3R,5R,6S)-3-[2-(2'2'2'-Trifluoroethoxy)-5-trifluoromethyl pyridin-3-yl]-6-phenyl-1-oxa-7H-azaspiro[4.5]decane hydrochloride (3R,5R,6S)-3-[2-(2',2',2'-Trifluoroethoxy)-5-trifluoromethylpyridin-3-yl]-6-phenyl-1-oxa-7-(tert-butyloxycarbonyl)-7-azaspiro[4.5]decane (95 mg, 0.1 mmol) in dichloromethane (10 mL) was added trifluoroacetic acid (1 mL) and the solution was stirred for 1 hr. After concentration, saturated sodium bicarbonate solution (20 mL) was added to the residue, and the suspension formed was extracted with ethyl acetate (2×20 mL). The extracts were dried (MgSO$_4$) and concentrated, and the residue taken up in ether (10 mL). Ethereal hydrogen chloride solution (1M, 1 mL) was added, and the solution triturated with cyclohexane, until the salt precipitated. This was removed by filtration and dried, to give the product as a white solid (58.6 mg, 0.12 mmol, 70% yield).

Melting point 245–246° C.; Found: C, 52.91; H, 4.69; N, 5.50; Calculated: C, 53.18; H, 4.67; N, 5.64; H$^1$ NMR δ(360 MHz, d$_6$-DMSO): 9.52 (1H, br s), 8.90 (1H, br s), 8.44 (1H, d, J 2.1 Hz), 7.89 (1H, d, J 2.1 Hz), 7.53–7.55(2H, m), 7.45–7.46 (3H, m), 4.89–4.94 (2H, m), 4.40 (1H, m), 4.02 (1H, t, J 7.5 Hz), 3.70 (1H, dd, J 10.4 and 8.2 Hz), 3.22–3.24 (1H, m), 2.26–2.29 (1H, m), 1.96–2.04 (3H, m), 1.85–1.94 (3H, m); M/z (ES$^+$) 461 (M+H).

EXAMPLE 29

(3R,5R,6S)-3-(2-Methoxy-5-trifluoromethylpyridin-3-yl)-6-phenyl-1-oxa-7H-azaspiro[4.51]decane A solution of (5R,6S)-6-phenyl-1-oxa-7-(tert-butyloxycarbonyl)-7-azaspiro[4.5]dec-3-ene (567 mg, 1.8 mmol), 3-bromo-2-methoxy-5-trifluoromethyl pyridine (893 mg, 3.49 mmol), lithium chloride (765 mg, 18 mmol), tetra-n-butylammonium chloride (495 mg, 1.8 mmol) and potassium formate (458 mg, 5.4 mmol) in N,N'-dimethylformamide (10 mL) was degassed with nitrogen at 60° C. for 45 minutes. Palladium acetate (45 mg) was then added and the solution stirred at 65° C. for 72 hrs. After cooling, water (100 mL) was added, and the solution extracted with ethyl acetate (2×100 mL). The extracts were dried (MgSO$_4$) and concentrated, and the residue purified by silica chromatography to give the crude product as a gum.

To a solution of this crude product in dichloromethane (10 mL) was added trifluoroacetic acid (1 mL) and the solution was stirred for 1 hr. After concentration, saturated sodium bicarbonate solution (50 mL) was added to the residue, and the suspension formed was extracted with dichloromethane (2×50 mL). The extracts were dried MgSO$_4$) and concentrated, and the residue purified by silica chromatography. The pure free base was taken up in ethyl acetate (10 mL) and ethereal hydrogen chloride solution (1M, 1 mL) added. After concentration, the residue was recrystallised from ethyl acetate/cyclohexane to give the salt as white crystals (56 mg, 0.13 mmol).

H$^1$ NMR δ(360 MHz, DMSO): 8.64 (1H, br s), 8.02 (1H, br s), 7.80–7.81 (2H, m), 7.74–7.76 (3H, m), 4.31 (1H, s), 4.62 (1H, br s), 4.18 (1H, t, J 7.8 Hz), 4.03 (3H, s), 3.96 (1H, dd, J 10.4 and 8.2 Hz), 3.50–3.54 (1H, m), 3.28–3.30 (1H, m), 2.48–2.50 (1H, m), 2.27–2.31 (3H, m), 2.02–2.08 (3H, m); m/z (ES$^+$) 393 (M+H).

EXAMPLE 30

(3R,5R,6S)-3-(2-Benzyloxy-5-trifluoromethylpyridin-3-yl)-6-phenyl-1-oxa-7-(tert-butyloxycarbonyl)-7-azaspiro[4.5]decane A solution of (5R,6S)-6-phenyl-1-oxa-7-(tert-butyloxycarbonyl)-7-azaspiro[4.5]dec-3-ene (500 mg, 1.59 mmol), 2-benzyloxy-3-bromo-5-trifluoromethylpyridine (80 mg, 2.41 mmol), lithium chloride (680 mg, 16 mmol), tetra-n-butylammonium chloride (440 mg, 1.6 mmol) and potassium formate (407 mg, 4.8 mmol) in N,N'-dimethylformamide (10 mL) was degassed with nitrogen at 60° C. for 45 minutes. Palladium acetate (40 mg) was then added and the solution stirred at 60° C. for 24 hrs.

After cooling, water (100 mL) was added, and the solution extracted with ethyl yl-acetate (2×100 mL). The extracts were dried (MgSO$_4$) and concentrated, and the residue purified by silica chromatography to give the product as a gum (212 mg, 0.37 mmol, 23% yield).

H$^1$ NMR δ(250 MHz, CDCl$_3$): 8.33 (1H, d, J 2.1 Hz), 7.70 (1H, d, J 2.1 Hz), 7.54–7.57 (2H, m), 7.23–7.44 (8H, m), 5.46 (2H, dd, J 12.2 and 18.7 Hz), 5.30 (1H, s), 4.29 (1H, t, J 7.6 Hz), 3.96–3.98 (1H, m), 3.87 (1H, t, J 8.2 Hz), 3.71–3.78 (1H, m), 2.72–2.82 (1H, m), 2.56 (1H, dd, J 7.8 and 12.7 Hz), 2.12–2.17 (1H, m), 198 (1H, dd, J 9.6 and 12.6 Hz), 1.55–1.65 (3H, m), 1.42 (9H, s)

EXAMPLE 31

(3R,5R,6S)-3-(2-Hydroxy-5-trifluoromethylpyridin-3-yl)-6-phenyl-1-oxa-7-(tert-butyloxycarbonyl)-7-azaspiro[14.51]decane (3R,5R,6S)-3-(2-Benzyloxy-5-trifluoromethylpyridin-3-yl)-6-phenyl-1-oxa-7-(tert-butyloxycarbonyl)-7-azaspiro[4.5]decane (212 mg, 0.37 mmol) and 10% palladium on carbon (20 mg) in methanol (20 mL) were hydrogenated at 50 psi hydrogen for 7 hrs. The catalyst was removed by filtration, and the filtrate concentrated to give the product as a foam (151 mg, 0.32 mmol, 85% yield).

H$^1$ NMR δ(250 MHz, CDCl$_3$): 7.65 (1H, d, J 2.3 Hz), 7.57–7.60 (2H, m), 7.49 (1H, d, J 2.3 Hz), 7.24–7.35 (3H, m), 5.33 (1H, s), 4.34 (1H, t, J 7.3 Hz), 3.96–4.01 (1H, m), 3.86 (1H, t, J 8.1 Hz), 3.70–3.77 (1H, m), 2.75–2.80 (1H, m), 260 (1H, dd, J 7.6 and 12.6 Hz), 2.18–2.23 (1H, m), 1.90 (1H, dd, J 9.6 and 12.6 Hz), 1.70–1.76 (3H, m), 1.47 (9H, s)

EXAMPLE 32

(3R,5R,6S)-3-(2-Difluoromethoxy-5-trifluoromethylpyridin-3-yl)-6-phenyl-1-oxa-7-(tert-butyloxycarbonyl)-7-azaspiro[4.51]decane (3R,5R,6S)-3-(2-Hydroxy-5-trifluoromethylpyridin-3-yl)-6-phenyl-1-oxa-7-(tert-butyloxycarbonyl)-7-azaspiro [4.5]decane (150 mg, 0.32 mmol) and potassium carbonate (47 mg, 0.34 mmol) in N,N'-dimethylformamide (2 mL) was treated with ethyl chlorodifluoroacetate (44 µL, 0.34 mmol) and heated at 65° C. for 18 hrs. After cooling, water (20 mL) was added and the mixture extracted with ethyl acetate (2×20 mL). The extracts were dried (MgSO$_4$) and concentrated, and the residue purified by silica chromatography to give the product (62 mg, 0.12 mmol, 37% yield).

H$^1$ NMR δ(250 MHz, CDCl$_3$): 8.35 (1H, s), 7.89 (1H, s), 7.57–7.60 (2H, m), 7.54 (1H, t, J 72.2 Hz), 7.26–7.36 (3H, m), 5.34 (1H, s), 4.33 (1H, t, J 7.3), 3.85–397 (3H, m), 2.68–2.76 (2H, m), 2.20–2.28 (1H, m), 1.70–1.93 (4H, m), 1.47 (9H, s)

EXAMPLE 33

(3R,5R,6S)-3-(2-Difluoromethoxy-5-trifluoromethylpyridin-3-yl)-6-yl-phenyl-1-oxa-7H-azaspiro[4.5]decane (3R,5R,6S)-3-(2-Difluoromethoxy-5-trifluoromethylpyridin-3-yl)-6-phenyl-1-oxa-7-(tert-butyloxycarbonyl)-7-azaspiro[4.5]decane (62 mg, 0.12 mmol) in dichloromethane (10 mL) was added trifluoroacetic acid (1 mL) and the solution was stirred for 30 minutes. After concentration, saturated sodium bicarbonate solution (10 mL) was added to the residue, and the suspension formed was extracted with ethyl acetate (2×10 mL). The extracts were dried (MgSO$_4$) and concentrated, and the residue taken up in ether (10 mL). Ethereal hydrogen chloride solution (1M, 1 mL) was added, and the solution triturated with tert-butyl methyl ether, until the salt precipitated. This was removed by filtration and dried, to give the product as a white solid (38 mg, 0.08 mmol, 68% yield).

H$^1$ NMR δ(360 MHz, d$_6$-DMSO): 8.50 (1H, br s), 8.09 (1H, br s), 7.58 (1H, t, J 72.0 Hz), 7.54–7.55 (2H, m), 7.46–7.47 (3H, m), 4.33 (1H, br s), 3.95–3.96 (1H, m), 3.76–3.77 (1H, m), 3.29–3.30 (1H, m), 3.00–3.04 (1H, m), 2.30–2.32 (1H, m), 1.98–2.06 (3H, m), 1.82–1.90 (3H, m); m/z (ES$^+$) 429 (M+H).

EXAMPLE 34

(3R,5R,6S)-3-(2-cyclopropyloxy-5-trifluoromethylpyridin-3-yl)-6-phenyl-1-oxa-7-(tert-butyloxycarbonyl)-7-azaspiro[4.51]decane To a solution of (3R,5R,6)-3-[2-(1-phenylsulfonylcyclopropyloxy)-5-trifluoromethylpyridin-3-yl]-6-phenyl-1-oxa-7-(tert-butyloxycarbonyl)-7-azaspiro [4.5]decane (423 mg, 0.64 mmol) and sodium hydrogen phosphate (363 mg, 2.56 mmol) in methanol (5mL) was added sodium mercury amalgam (576 mg, 10%) and the resulting mixture was stirred for 30 minutes. Saturated sodium bicarbonate solution (50 mL) was added, and the suspension extracted with ethyl acetate (2×50 mL). The extracts were dried (MgSO$_4$) and concentrated, and the residue purified by silica chromatography to give the product as a gum (210 mg, 0.41 mmol, 63% yield).

H$^1$ NMR δ(250 MHz, CDCl$_3$): 8.38 (1H, d, J 2.3 Hz), 7.67 (1H, d, J 2.3 Hz), 7.57–7.67 (2H, m), 7.25–7.36 (3H, m), 5.32 (1H, br s), 4.39 (1H, septet, J 2.8 Hz), 427 (1H, t, J 7.4 Hz), 3.93–3.99 (1H, m), 3.79 (1H, t, J 8.3 Hz), 3.63–3.70 (1H, m), 2.72–2.80 (1H, m), 2.57 (1H, dd, J 7.6 and 12.6 Hz) 2.19–2.24 (1H, m), 1.87 (1H, dd, J 9.9 and 12.6 Hz), 1.70–1.75 (3H, m), 1.46 (9H, s), 0.76–0.85 (4H, m)

EXAMPLE 35

(3R,5R,6S)-3-(2-cyclopropyloxy-5-trifluoromethylpyridin-3-yl)-6-phenyl-1-oxa-7H-azaspiro[4.51]decane hydrochloride (3R,5R,6S)-3-(2-cyclopropyloxy-5trifluoromethylpyridin-3-yl)-6-phenyl-1-oxa-7-(tert-butyloxycarbonyl)-7-azaspiro[4.5]decane (200 mg, 0.39 mmol) in dichloromethane (20 mL) was added trifluoroacetic acid (2 mL) and the solution was stirred for 1 hr. After concentration, saturated sodium bicarbonate solution (20 mL) was added to the residue, and the suspension formed was extracted with ethyl acetate (2×10 mL). The extracts were dried (MgSO$_4$) and concentrated, and the residue taken up in ether (10 mL). Ethereal hydrogen chloride solution (1M, 1 mL) was added, and the solution concentrated. The crude salt was recrystallised in ethyl acetate to give the product as a white solid (67 mg, 0.15 mmol, 38% yield).

Melting point: 244–246° C.; H$^1$ NMR δ(360 MHz, d$_6$-DMSO): 9.63 (1H, br s), 8.92 (1H, br s), 8.41 (1H, d, J 2.1 Hz), 7.80 (1H, d, J 2.1 Hz), 7.55–7.57 (2H, m), 7.48–7.50 (3H, m), 4.36 (1H, br s), 4.28 (1H, septet, J 3.1 Hz), 3.91 (1H, t, J 7.5 Hz), 3.66 (1H, dd, J 8.1 and 10.6 Hz), 3.23–3.27 (1H, m), 3.00–3.04 (1H, m), 2.22 (1H, dd, J 7.4 and 12.4 Hz), 1.75–2.06 (6H, m), 0.70–0.75 (2H, m), 0.46–0.57 (2H, m); m/z (ES$^+$) 419 (M+H).

EXAMPLE 36

(3R,5R,6S)-3-[3-Methoxy-6-trifluoromethylpyridin-4-yl]-6-phenyl-1-oxa-7-tert-butyloxycarbonyl)-7-azaspiro[4.5]decane A solution of (5R,6S)-6-phenyl-1-oxa-7-(tert-butyloxycarbonyl)-7-azaspiro[4.5]dec-3-ene (400 mg, 1.26 mmol), 4-bromo-3-methoxy-6-trifluoromethylpyridine (435 mg, 1.7 mmol), lithium chloride (475 mg, 11.6 mmol), tetra-n-butylammonium chloride (350 mg, 1.26 mmol) and potassium formate (412 mg, 4.9 mmol) in N,N'-dimethylformamide (8.5 ml) was degassed with a stream of nitrogen for 30 minutes. Palladium acetate (86 mg, 0.38 mmol) was then added and the solution stirred at 50° C. for 4 days.

After cooling, the reaction mixture was filtered through a pad of Celite. The cake was washed with ethyl acetate. The filtrate was washed with saturated aqueous NaHCO$_3$, water, dried (Na$_2$SO$_4$) and concentrated. The residue was purified by chromatography on silica gel (hexane:ethyl acetate 4–40%) to give 1:1 mixture of 2 and 3 substituted spirocycles (69 mg, 11%). Further purification by preparative thin layer chromatography afforded the title compound (18 mg, 3%) as a colourless oil.

H$^1$ NMR δ(360 MHz, CDCl$_3$): 8.30 (1H, s), 7.60 (2H, d, J 7.7 Hz), 7.56 (1H, s), 7.31–7.36 (2H, m), 7.23–7.28 (1H, m), 5.37 (1H, s), 4.32 (1H, dd, J 7.1 Hz and 7.8 Hz), 4.00 (3H, s), 3.85–4.00 (2H, m), 3.86 (1H, t, J 8.0 Hz), 2.77 (1H, dt, J 3.6 Hz and 12.8 Hz), 2.65 (1H, dd, J 7.4 Hz and 12.7 Hz), 2.26 (1H, dt, J 4.9 Hz and 12.5 Hz), 1.86 (1H, dd, J 9.6 Hz and 12.6 Hz), 1.65–1.80 (2H, m), 1.48 (9H, s).

EXAMPLE 37a (3R,5R,6S)-3-[3-Methoxy-6-trifluoromethylpyridin-4-yl]-6-phenyl-1-oxa-7-azaspiro[4.5]decane A mixture of (3R,5R,6S)-3-[3-methoxy-6-trifluoromethylpyridin-4-yl]-6-phenyl-1-oxa-7-(tert-butyloxycarbonyl)-7-azaspiro[4.5]decane (18 mg, 0.037 mmol), trifluoroacetic acid (0.5 ml) and dichloromethane (2 ml) was stirred at room temperature for 1 h, then concentrated and treated with a solution of aqueous ammonia in methanol. The solution was concentrated and the residue was purified by preparative thin layer chromatography to give the product (8 mg, 56%).

H$^1$ NMR δ(360 MHz, CDCl$_3$): 8.13 (1H, s), 7.45–7.50 (2H, m), 7.31–7.37 (3H, m), 7.27 (1H, s), 3.98 (1H, t, J 7.5 Hz), 3.81 (3H, s), 3.66 (1H, dd, J 8.1 Hz and 9.9 Hz), 3.54 (1H, s), 3.22 (1H, dd, J 4.3 Hz and 12.1 Hz), 2.78 (1H, dt, J 2.9 Hz and 12.4 Hz), 2.15–2.35 (4H, m), 1.95–2.10 (1H, m), 1.58–1.75 (3H, m).

EXAMPLE 37b (3R,5R,6S)-3-[3-Methoxy-6-trifluoromethylpyridin-4-yl]-6-phenyl-1-oxa-7H-7-azaspiro[4.5]decane hydrochloride A ethereal solution of hydrogen chloride (1 ml, 1M in diethyl ether, 1 mmol.) was added to a stirred solution of (3R,5R,6S)-3-[3-methoxy-6-trifluoromethylpyridin-4-yl]-6phenyl-1-oxa-7-azaspiro[4.5]decane in dichloromethane (0.2 ml) to form white solid. The reaction mixture was stirred for 2 h and concentrated. The solid residue was recrystallised from dichloromethane:ether to give the product as a white crystals.

H$^1$ NMR δ(360 MHz, d$_4$-MeOH): 8.24 (1H, s), 7.45–7.62 (5H, m), 7.44 (1H, s), 5.48 (1H, s), 4.31 (1H, s), 4.10 (1H, t, J 7.9 Hz), 3.86 (3H, s), 3.81 (1H, t, J 8.6 Hz), 3.42 (1H, dd, J 4.0 Hz and 12.1 Hz), 3.18 (1H, dt, J 4.0 Hz and 13.1 Hz), 2.20–2.40 (2H, m), 2.04–2.18 (1H, m), 1.9–2.0 (3H, m); m/z (ES$^+$) 393 (M+H).

EXAMPLE 38a (5R,6S)-3-[3-Methoxy-6-trifluoromethylpyridin-2-yl]-6-phenyl-1-oxa-2-oxo-7-(tert-butyloxycarbonyl)-7-azaspiro[4.5]dec-3-ene A solution of (5R,6S)-6-phenyl-1-oxa-2-oxo-7-(tert-butyloxycarbonyl)-7-aza-3-tributylstannylspiro[4.5]dec-3-ene (448 mg, 0.725 mmol), 2-bromo-3-methoxy-6-trifluoromethylpyridine (185 mg, 0.723 mmol), lithium chloride (200 mg, 4.7 mmol) in N,N'-dimethylformamide (7 ml) was degassed with a stream of nitrogen for 30 minutes. Then copper (I) iodide (27 mg, 0.14 mmol) and tetrakis (triphenylphosphine)palladium (87 mg, 0.07 mmol) were added. The reaction mixture was stirred at 97° C. overnight. After cooling to room temperature the reaction mixture was treated with diluted aqueous NaHCO$_3$ and extracted with ethyl acetate (3×25 ml). The combined organic extracts were dried (Na$_2$SO$_4$) and concentrated The residue was purified by chromatography on silica gel (50 g, iso-hexane:ethyl acetate 10–35%) to afford the product (370 mg) as a colourless oil.

H$^1$ NMR δ(360 MHz, CDCl$_3$): 7.96 (1H, s), 7.67 (1H, d, J 8.6 Hz), 7.48 (2H, d, J 7.7 Hz), 7.20–7.40 (4H, m), 5.37 (1H, s), 4.19 (1H, dd, J 5.4 Hz and 13.1 Hz), 3.87 (3H, s), 3.85–4.00 (2H, m), 3.86 (1H, t, J 8.0 Hz), 3.07 (1H, m), 2.45 (1H, m) 1.78–2.04 (3H, m), 1.41 (9H, s).

EXAMPLE 38b (3R,6R,6S)-3-[3-Methoxy-6-trifluoromethylpyridin-2-yl]-6-phenyl-1-oxa-2-oxo-7-(tert-butyloxycarbonyl)-7-azaspiro[4.5]decane and (3S,5R,6S)-3-[3-methoxy-6-trifluoromethyl-pyridin-2-]-6-phenyl-1-oxa-2-oxo-7-(tert-butyloxycarbonyl)-7-azaspiro[4.5]decane Sodium borohydride (420 mg, 11 mmol) was added portionwise with stirring to an ice cooled solution of (5R,6S)-3-[3-methoxy-6-trifluoromethylpyridin-2-yl]-6-phenyl-1-oxa-2-oxo-7-(tert-butyloxycarbonyl-7-azaspiro[4.5]dec-3-ene (370 mg) and nickel(II) chloride hexahydrate (15 mg, 0.063 mmol) in dry methanol (5 ml). After stirring for 70 min, the mixture was treated with aqueous NaHCO₃ and extracted with ethyl acetate (3×25 ml). The combined organic extracts were washed twice with water, brine then dried (Na₂SO₄) and concentrated. The residue was purified by chromatography on silica gel (iso-hexane:ethyl acetate 10–35%) to give the product (292 mg, 80%) as a 2.8:1 mixture of (3S,5R,6S)-3-[3-methoxy-6-trifluoromethylpyridin-2-yl]-6-phenyl-1-oxa-2-oxo-7-(tert-butyloxycarbonyl)-7-azaspiro[4.5]decane and (3R,5R,6S)-3-[3-methoxy-6-trifluoromethylpyridin-2-yl]-6-phenyl-1-oxa-2-oxo-7-(tert-butyloxycarbonyl)-7-azaspiro[4.5]decane.

H¹ NMR δ(250 MHz, CDCl₃, 2.8:1 mixture of epimers): 7.61 (1H, d, J 8.6 Hz), 7.54 (2H, d, J 7.3 Hz), 7.20–7.40 (4H, m), 5.41 (1H, s), 4.46 (0.26 H, t, J 10.7 Hz), 4.41 (0.74H, t, J 10.4 Hz), 4.05 (1H, m), 3.92 (3×0.26H, s), 3.74 (3×0.74H, s), (1H, dd, J 5.4 Hz and 13.1 Hz), 3.87 (3H, s), 3.85–4.00 (2H, m), 3.86 (1H, t, J 8.0 Hz), 3.07 (1H, m), 2.45 (1H, m), 1.78–2.04 (3H, m), 1.45 (9×0.26H, s), 1.39 (9×0.74H, s).

EXAMPLE 39

(3R,5R,6S)-3-[3-Methoxy-6-trifluoromethylpyridin-2-yl]-6-phenyl-1-oxa-2-oxo-7-azaspiro[4.5]decane and (3S,5R,6S)-3-[3-methoxy-6-trifluoromethylpyridin-2-yl]-6-phenyl-1-oxa-2-oxo-7-azaspiro[4.5]decane A solution of 2.8:1 mixture of (3S,5R,6S)-3-[3-methoxy-6-trifluoromethylpyridin-2-yl]-6-phenyl-1-oxa-7-(tert-butyloxycarbonyl)-7-azaspiro[4.5]decane and (3R,5R,6S)-3-[3-methoxy-6-trifluoromethylpyridin-2-yl]-6-phenyl-1-oxa-7-(tert-butyloxycarbonyl)-7-azaspiro[4.5]decane (292 mg, 0.576 mmol) in dichloromethane (1.5 ml) was treated with trifluoroacetic acid (0.5 ml) and stirred at room temperature overnight. The reaction mixture was concentrated in vacuo, treated with saturated aqueous NaHCO₃ and extracted with dichloromethane (3×15 ml). The combined organic extracts were dried (Na₂SO₄) and concentrated to give the crude product as a 5.5:1 mixture of (3R,5R,6S)-3-[3-methoxy-6-trifluoromethylpyridin-2-yl]-6-phenyl-1-oxa-2-oxo-7-azaspiro[4.5]decane and (3S,5R,6S)-3-[3-methoxy-6-trifluoromethylpyridin-2-yl]-6-phenyl-1-oxa-2-oxo-7-azaspiro[4.5]decane (235 mg, 100%).

The crude product was dissolved in dichloromethane (1 ml) and treated with 1,8-diazabicyclo[5.4.0]undec-7-ene (DBU) (25 μl, 0.17 mmol). The reaction mixture was stirred at room temperature for 70 min and concentrated in vacuo to give a 4:1 mixture of (3R,5R,6S)-3-[3-methoxy-6-trifluoromethylpyridin-2-yl]-6-phenyl-1-oxa-2-oxo-7-azaspiro[4.5]decane and (3S,5R,6S)-3-[3-methoxy-6-trifluoromethylpyridin-2-yl]-6phenyl-1-oxa-2-oxo-7-azaspiro[4.5]decane which was used in Example 40 without purification.

EXAMPLE 40a (3R,5R,6S)-3-[3-methoxy-6-trifluoromethylpyridin-2-yl]-6-phenyl-1-oxa-7-azaspiro[4.5]decane The preceding mixture was treated with tetrahydrofuran (5 ml) and cooled to 0° C. and a solution of lithium aluminium hydride in tetrahydrofuran (1M; 2 mL, 2 mmol) added dropwise. The reaction mixture was stirred for 2 hours and treated carefully with saturated aqueous Na₂SO₄ (5 drops). The mixture was stirred for 15 min, solid Na₂SO₄ was added and the mixture was filtered through a pad of Celite. The filtrate was concentrated to give crude (2S,3R)-3-hydroxy-3-[(2R,S)-3-hydroxy-2-(3-methoxy-6-trifluoromethylpyridin-2-yl)propyl]-2-phenylpiperidine (212 mg) which was used in next step without purification.

Diethyl azodicarboxylate (0.11 ml, 0.694 mmol) was added dropwise to a stirred solution of (2S,3R)-3-hydroxy-3-[(2R,S)-3-hydroxy-2-(3-methoxy-6-trifluoromethylpyridin-2-yl)propyl]-2-phenylpiperidine (190 mg) and triphenylphosphine (182 mg, 0.694 mmol) in tetrahydrofuran (3 ml). The reaction mixture was stirred at room temperature for 60 h and concentrated in vacuo. The residue was treated with 2M hydrochloric acid (5 ml) and toluene (30 ml). The phases were separated. The organic layer was extracted twice with water (2×5 ml). The combined aqueous layers were washed with toluene (5 ml), treated with methanol (2 ml) and 4M aqueous NaOH (5 ml). The resulting mixture was stirred at room temperature for 3 hours and extracted with dichloromethane (3×5 ml). The combined organic extracts were dried (Na₂SO₄) and concentrated. The residue was purified by chromatography on silica gel (dichloromethane:methanol 2–5% containing 0.4% of triethylamine) to afford the product as a colourless oil.

H¹ NMR δ(360 MHz, CDCl₃): 7.49 (2H, dd, J 1.8 Hz and 7.9 Hz), 7.39 (1H, d, J 8.5 Hz), 7.26–7.36 (3H, m), 6.99 (1H, d, J 8.5 Hz), 4.01 (1H, t, J 7.8 Hz), 3.81 (1H, dd, J 8.0 Hz and 10.2 Hz), 3.70 (3H, s), 3.54 (1H, s), 3.21 (1H, dd, J 4.1 Hz and 12.2 Hz), 2.78 (1H, dt, J 2.8 Hz and 12.3 Hz), 2.55 (1H, m), 1.90–2.20 (5H, m), 1.68 (1H,dd, J 3.5 Hz and 12.9 Hz), 1.60 (1H, m).

EXAMPLE 40b (3R,5R,6S)-3-[3-Methoxy-6-trifluoromethylpyridin-2-yl]-6-phenyl-1-oxa-7H-7-azaspiro[4.5]decane hydrochloride A ethereal solution of hydrogen chloride (1 ml, 1M in diethyl ether, 1 mmol.) was added to a stirred solution of (3R,5R,6S)-3-[3-methoxy-6-trifluoromethylpyridin-2-yl]-6-phenyl-1-oxa-7-azaspiro[4.5]decane (25 mg, 0.064 mmol) in dichloromethane (0.5 ml) to form white solid. the reaction mixture was stirred for 1 hour and concentrated. The solid residue was recrystallised from dichloromethane:iso-hexane to give the product as a white crystals.

H¹ NMR δ(360 MHz, d₄-MeOH): 7.50–7.62 (5H, m), 7.33 (1H, s), 5.48 (2H, s), 4.30 (1H, s), 4.11 (1H, t, J 7.5 Hz), 3.91 (1H, dd, J 7.9 Hz and 9.7 Hz), 3.75 (3H, s), 3.41 (1H, dd, J 5.3 Hz and 12.4 Hz), 3.19 (1H, dd, J 3.1 Hz and 12.4 Hz), 3.18 (1H, dt, J 4.0 Hz and 13.1 Hz), 2.67 (1H, m) 2.26 (2H, m), 2.16 (2H, m), 194 (2H, m); m/z (ES⁺) 393 (M+H).

What is claimed is:

1. A compound of the formula (I):

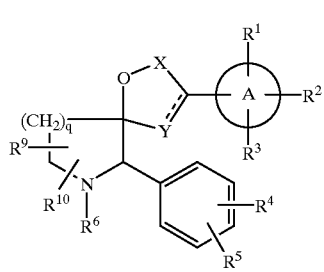

(I)

wherein
ring A is a 6-membered aromatic heterocyclic group containing one, two or three nitrogen atoms; which is pyridyl
X is —CH₂—;
Y is —CH₂—, —CH═ or;
R¹ is hydrogen, hydroxy, C₁₋₆alkyl, C₂₋₆alkenyl, C₃₋₇cycloalkyl, C₃₋₇cycloalkylC₁₋₄alkyl, C₁₋₆alkoxy, fluoroC$_{1-6}$alkoxy, C$_{1-6}$alkoxyC$_{1-4}$alkyl, C$_{1-6}$alkoxyC$_{1-4}$alkoxy, fluoroC$_{1-6}$alkoxyC$_{1-4}$alkyl, C$_{2-6}$alkenyloxy, C$_{3-7}$cycloalkoxy, C$_{3-7}$cycloalkyl C$_{1-4}$alkoxy, phenoxy, benzyloxy, cyano, halogen, NR$^a$R$^b$, SR$^a$, SOR$^a$, SO$_2$R$^a$ or OSO$_2$R$^a$, where R$^a$ and R$^b$ each independently represent hydrogen, C$_{1-4}$alkyl or fluoroC$_{1-4}$alkyl;

R$^2$ is hydrogen, halogen, C$_{1-6}$alkyl or C$_{1-6}$alkoxy;

or when R$^2$ is adjacent to R$^1$, they may be joined together such that there is formed a 5- or 6-membered saturated or unsaturated ring containing one or two atoms selected from nitrogen, oxygen and sulphur, which ring is optionally substituted by a group selected from C$_{1-4}$alkyl, CF$_3$, =O or =S;

R$^3$ is hydrogen, halogen, C$_{1-6}$alkyl, fluoroC$_{1-6}$alkyl, C$_{1-6}$alkoxy, fluoroC$_{1-6}$alkoxy, C$_{3-7}$cycloalkyl, C$_{3-7}$cycloalkylC$_{1-4}$alkyl, cyano, SR$^a$, SOR$^a$, SO$_2$R$^a$, NR$^a$R$^b$, NR$^a$COR$^{14}$, or C$_{1-4}$alkyl substituted by cyano or CO$_2$R$^a$ where R$^a$ and R$^b$ are as previously defined;

or R$^3$ is a 5- or 6-membered aromatic heterocyclic group containing 1, 2, 3 or 4 heteroatoms, selected from nitrogen, oxygen and sulphur, which group is optionally substituted by one or two groups selected from C$_{1-6}$alkyl, C$_{1-6}$alkoxy, C$_{3-7}$cycloalkyl, C$_{3-7}$cycloalkylC$_{1-4}$alkyl, trifluoromethyl, OCF$_3$, NO$_2$, CN, SR$^a$, SOR$^a$, SO$_2$R$^a$, COR$^a$, CO$_2$R$^a$, phenyl, —(CH$_2$)$_r$NR$^a$R$^b$, —(CH$_2$)$_r$NR$^a$COR$^b$, —(CH$_2$)$_r$CONR$^a$R$^b$, or CH$_2$C(O)R$^a$, where R$^a$ and R$^b$ are each independently hydrogen or C$_{1-4}$alkyl and r is zero, 1 or 2;

R$^4$ is hydrogen, halogen, C$_{1-6}$alkyl, C$_{1-6}$alkoxy, CF$_3$, OCF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ each independently represent hydrogen or C$_{1-4}$alkyl;

R$^5$ is hydrogen, halogen, C$_{1-6}$alkyl, CF$_3$ or C$_{1-6}$alkoxy substituted by C$_{1-4}$alkyl;

R$^6$ is hydrogen, COR$^a$, CO$_2$R$^a$, COCONR$^a$R$^b$, COCO$_2$R$^a$, C$_{1-6}$alkyl optionally substituted by a group selected from (CO$_2$R$^a$, CONR$^a$R$^b$, hydroxy, CN, COR$^a$, NR$^a$R$^b$, C(NOH)NR$^a$R$^b$, CONHphenyl (C$_{1-4}$alkyl), COCO$_2$R$^a$, CONHNR$^a$R$^b$, C(S)NR$^a$R$^b$, CONR$^a$C$_{1-6}$alkylR$^{12}$, CONR$^{13}$C$_{2-6}$alkenyl, CONR$^{13}$C$_{2-6}$alkynyl, COCONR$^a$R$^b$, CONR$^a$C(NR$^b$)NR$^a$R$^b$, CONR$^a$heteroaryl, and phenyl optionally substituted by one, two or three substituents selected from C$_{1-6}$alkyl, C$_{1-6}$alkoxy, halogen and trifluoromethyl);

or R$^6$ is a group of the formula —CH$_2$C≡CCH$_2$NR$^7$R$^8$ where R$^7$ and R$^8$ are as defined below;

or R$^6$ is C$_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula ZNR$^7$R$^8$ where Z is C$_{1-6}$alkylene or C$_{3-6}$cycloalkyl;

R$^7$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy or hydroxyl;

R$^8$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy, hydroxyl or a 4, 5 or 6 membered heteroaliphatic ring containing one or two heteroatoms selected from N, O and S;

or R$^7$, R$^8$ and the nitrogen atom to which they are attached form a heteroaliphatic ring of 4 to 7 ring atoms, optionally substituted by one or two groups selected from hydroxy or C$_{1-4}$alkoxy optionally substituted by a C$_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is C$_{1-4}$alkyl optionally substituted by hydroxy or C$_{1-4}$alkoxy;

or R$^7$, R$^8$ and the nitrogen atom to which they are attached form a non-aromatic azabicyclic ring system of 6 to 12 ring atoms;

or Z, R$^7$ and the nitrogen atom to which they are attached form a heteroaliphatic ring to 4 to 7 ring atoms which may optionally contain an oxygen ring atom;

R$^9$ and R$^{10}$ each independently are hydrogen, halogen, C$_{1-6}$alkyl, CH$_2$OR$^d$, oxo, CO$_2$R$^a$ or CONR$^a$R$^b$ where R$^a$ and R$^b$ are as previously defined and R$^d$ represents hydrogen, C$_{1-6}$alkyl or phenyl;

R$^{12}$ is OR$^a$, CONR$^a$R$^b$ or heteroaryl;

R$^{13}$ is H or C$_{1-6}$alkyl;

R$^{14}$ is C$_{1-4}$alkyl, C$_{1-6}$alkoxy, fluoroC$_{1-6}$alkyl or phenyl;

q is 2; and when Y is —CH= or —CH$_2$CH=, the broken line indicates a double bond; or a pharmaceutically acceptable salt thereof.

2. A compound of formula (Ia)

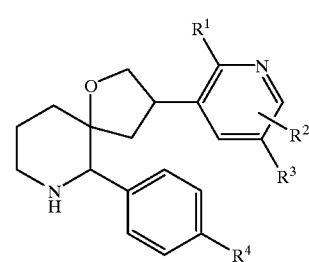

(Ia)

wherein R$^1$, R$^2$, R$^3$ and R$^4$ are as defined in claim 1; or a pharmaceutically acceptable salt thereof.

3. A compound of the formula (Ib)

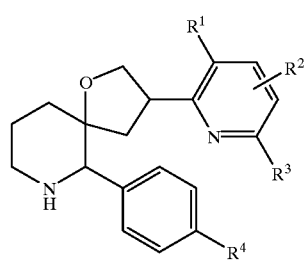

(Ib)

wherein R$^1$, R$^2$, R$^3$ and R$^4$ are as defined in claim 1; or a pharmaceutically acceptable salt thereof.

4. A compound of formula (Ic)

(Ic)

wherein $R^1$, $R^2$, $R^3$ and $R^4$ are as defined in claim 1; or a pharmaceutically acceptable salt thereof.

5. A compound as claimed in claim 1 wherein $R^1$ is hydrogen, $C_{1-6}$alkyl, $C_{1-6}$alkoxy, fluoro$C_{1-6}$alkoxy, $C_{3-7}$cycloalkoxy, halogen or $NR^aR^b$.

6. A compound as claimed in claim 1 wherein $R^2$ is a hydrogen atom.

7. A compound as claimed in claim 1 wherein $R^3$ is halogen, $C_{1-6}$alkyl, fluoro$C_{1-6}$alkyl, $C_{1-6}$alkoxy, fluoro$C_{1-6}$alkoxy, cyano or a 5-membered aromatic heterocyclic group as defined in claim 1.

8. A compound as claimed in claim 1 wherein $R^4$ is a hydrogen atom or a fluorine atom.

9. A compound as claimed in claim 1 or in claim 1 wherein $R^5$ is a hydrogen atom.

10. A compound as claimed in claim 1 or in claim 1 wherein $R^6$ is a hydrogen atom.

11. A compound as claimed in claim 1 or in claim 1 wherein X is —CH$_2$—.

12. A compound as claimed in claim 1 or in claim 1 wherein Y is —CH$_2$— or —CH=.

13. A compound as claimed in claim 1 or in claim 1 wherein q is 2.

14. A compound selected from:

(5R,6S)-3-(3-methoxy-6-N-methyltrifluoromethanesulfonamidopyridin-2-yl)-6-phenyl-1-oxa-7H-azaspiro[4.5]dec-3-ene;
(3S,5R,6S)-3-(3-methoxy-6-N-methyltrifluoromethanesulfonamidopyridin-2-yl)-6-phenyl-1-oxa-7H-azaspiro[4.5]decane;
(5R,6S)-3-(3-methoxy-6-(5-trifluoromethyl-1,2,3,4-tetrazol-1-yl)-pyridin-2-yl)-6-phenyl-1-oxa-7H-azaspiro[4.5]dec-3-ene;
(3S,5R,6S)-3-(3-methoxy-6-(5-trifluoromethyl-1,2,3,4-tetrazol-1-yl)-pyridin-2-yl) -6-phenyl-1-oxa-7H-azaspiro[4.5]decane;
(5R,6S)-3-(3-methoxy-6-(2-trifluoromethylimidazol-1-yl)pyridin-2-yl)-6-phenyl-1-oxa-7H-azaspiro[4.5]dec-3-ene;
(3S,5R,6S)-3-(3-methoxy-6-(2-trifluoromethylimidazol-1-yl)pyridin-2-yl)-6-phenyl-1-oxa-7H-azaspiro[4.5]decane;
(3S,5R,6S)-3-(3-methoxy-6-dimethylaminopyridin-2-yl)-6-phenyl-1-oxa-7H -azaspiro[4.5]decane;
(5R,6S)-3-(2-methoxy-5-trifluoromethylpyridin-3-yl)-6-phenyl-1-oxa-7H -azaspiro[4.5]dec-3-ene;
(3S,5R,6S)-3-(2-methoxy-5-trifluoromethylpyridin-3-yl)-6-phenyl-1-oxa-7H -azaspiro[4.5]decane;
(5R,6S)-3-(2-dimethylamino-5-trifluoromethylpyridin-3-yl)-6-phenyl-1-oxa-7H -azaspiro[4.5]dec-3-ene;
(3S,5R,6S)-3-(2-dimethylamino-5-trifluoromethylpyridin-3-yl)-6-phenyl-1-oxa-7H-azaspiro[4.5]decane;
(3S,5R,6S)-3-(2-(2,2,2-trifluoroethoxy)-5-trifluoromethylpyridin-3-yl)-6-phenyl-1-oxa-7H-azaspiro[4.5]decane;
(5R,6S)-3-(2-(2,2,2-trifluoroethoxy)-5-(2-trifluoromethylimidazol-1-yl)pyridin-3-yl)-6-phenyl-1-oxa-7H-azaspiro[4.5]dec-3-ene;
(3S,5R,6S)-3-(2-(2,2,2-trifluoroethoxy)-5-(2-trifluoromethylimidazol-1-yl)pyridin-3-yl)-6-phenyl-1-oxa-7H-azaspiro[4.5]decane;
(3S,5R,6S)-3-(2-methoxy-5-(2-trifluoromethylimidazol-1-yl)pyridin-3-yl)-6-phenyl-1-oxa-7H-azaspiro[4.5]decane;
(3S,5R,6S)-3-(2-isopropoxy-5-trifluoromethylpyridin-3-yl)-6-phenyl-1-oxa-7H -azaspiro[4.5]decane;
(3S,5R,6S)-3-(2-ethoxy-5-trifluoromethylpyridin-3-yl)-6-phenyl-1-oxa-7H -azaspiro[4.5]decane;
(3S,5R,6S)-3-(2-(2-methoxyethoxy-5-trifluoromethylpyridin-3-yl)-6-phenyl-1-oxa-7H-azaspiro[4.5]decane;
(3R,5R,6S)-3-(2-isopropoxy-5-trifluoromethylpyridin-3-yl)-6-phenyl-1-oxa-7H -azaspiro[4.5]decane;
(3R,5R,6S)-3-(2-ethoxy-5-trifluoromethylpyridin-3-yl)-6-phenyl-1-oxa-7H -azaspiro[4.5]decane;
(3R,5R,6S)-3-(2-(2,2,2-trifluoroethoxy)-5-trifluoromethylpyridin-3-yl)-6-phenyl-1-oxa-7H-azaspiro[4.5]decane;

or a pharmaceutically acceptable salt thereof.

15. A compound selected from:

(3R,5R,6S)-3-(2-methoxy-5-trifluoromethylpyridin-3-yl)-6-phenyl-1-oxa-7H -azaspiro[4.5]decane;
(3R,5R,6S)-3-(2-difluoromethoxy-5-trifluoromethylpyridin-3-yl)-6-phenyl-1-oxa-7H-azaspiro[4.5]decane;
(3R,5R,6S)-3-(2-cyclopropyloxy-5-trifluoromethylpyridin-3-yl)-6-phenyl-1-oxa-7H -azaspiro[4.5]decane;
(3R,5R,6S)-3-[3-methoxy-6-trifluoromethylpyridin-4-yl]-6-phenyl-1-oxa-7-azaspiro[4.5]decane;
(3R,5R,6S)-3-[3-methoxy-6-trifluoromethylpyridin-2-yl]-6-phenyl-1-oxa-7-azaspiro[4.5]decane;
or a pharmaceutically acceptable salt thereof.

16. A pharmaceutical composition comprising a compound as claimed claim 1, together with at least one pharmaceutically acceptable carrier or excipient.

17. A method for the treatment or prevention of physiological disorders associated with an excess of tachykinins, which method comprises administration to a patient in need thereof of an effective amount of a tachykinin reducing amount of a compound according to claim 1.

18. A method according to claim 17 for the treatment of pain or inflammation, migraine, emesis or postherpetic neuralgia.

19. A process for the preparation of a compound as claimed in claim 1 which comprises:

(A), where X is —CH$_2$— and Y is —CH$_2$— or reduction of a compound of formula (II)

(II)

wherein ring A, $R^1$, $R^2$, $R^3$, $R^4$, $R^5$, $R^6$, $R^9$, $R^{10}$ and q are as defined in claim 1 and Y' is —CH=

(B), interconversion of a corresponding compound of formula (I) in which $R^6$ is H, i.e. a compound of formula (III)

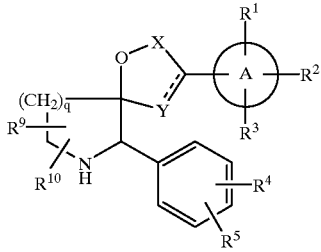
(III)

wherein ring A, $R^1$, $R^2$, $R^3$, $R^4$, $R^5$, $R^9$, $R^{10}$, X, Y, q and the broken line are as defined in claim 1, by reaction with a compound of formula (IV):

LG-$R^{6a}$ (IV)

where $R^{6a}$ is a group of the formula $R^6$ as defined in claim 1 or a precursor therefor and LG is a leaving group; and, if $R^{6a}$ is a precursor group, converting it to a group $R^6$; or (C), a coupling reaction between a compound of formula (V) and (VI)

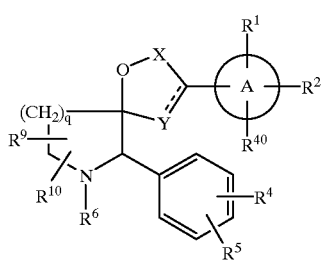
(V)

$R^{41}$—$R^3$ (VI)

wherein one of $R^{40}$ and $R^{41}$ is $B(OH)_2$ or $Sn(alkyl)_3$ or a derivative thereof, and the other is a leaving group; or (D), cyclisation of a compound of formula (VII)

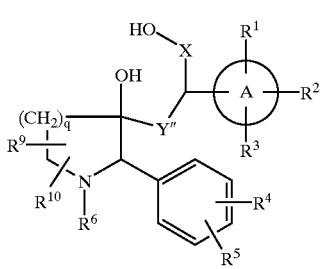
(VII)

wherein Y" is —$CH_2$— or —$CH_2CH_2$—, by an acid catalysed intramolecular cyclisation reaction, or by a dehydration reaction; or (E), where X is —$CH_2$— and Y is —$CH_2CH$=, reaction of a compound of formula (VIII)

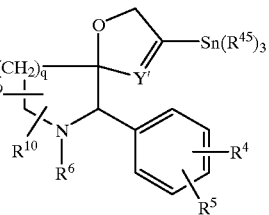
(VIII)

wherein each $R^{45}$ is a $C_{1-4}$alkyl group, with a compound of formula (IX)

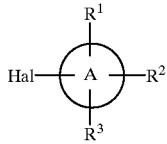
(IX)

wherein Hal is a halogen atom; or
(F), reaction of a compound of formula (XVI)

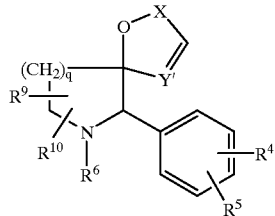
(XVI)

with a compound of formula (IX), under the conditions of a reductive Heck reaction; or
(G), where $R^1$ is a cyclopropoxy group, reacting a compound of formula (XXVII)

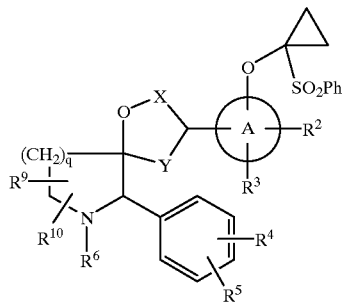
(XXVII)

wherein Ph is a phenyl group, with sodium amalgam; or
(H), where X is —$CH_2$— and Y is —$CH_2$—, may be prepared by a two step reaction comprising
a) reduction of a compound of formula (XXIV)

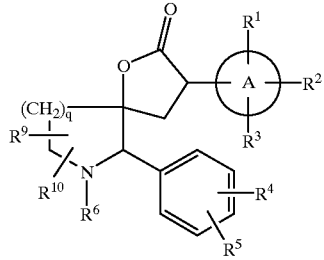
(XXIV)

to give a compound of the formula (XXIVa)

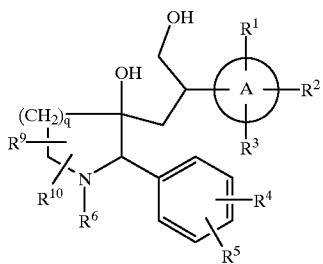

(XXIVa)

b) reaction of a compound of formula (XXIVa) with diethylazodicarboxylate to effect cyclisation to give a compound of formula (I);

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

* * * * *